US010786466B2

(12) United States Patent
Shulman et al.

(10) Patent No.: US 10,786,466 B2
(45) Date of Patent: Sep. 29, 2020

(54) 2,4-DINITROPHENOL FORMULATIONS AND METHODS USING SAME

(71) Applicant: Yale University, New Haven, CT (US)

(72) Inventors: Gerald I. Shulman, East Haven, CT (US); Rachel Jamison Perry, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/911,322

(22) PCT Filed: Aug. 29, 2014

(86) PCT No.: PCT/US2014/053406
§ 371 (c)(1),
(2) Date: Feb. 10, 2016

(87) PCT Pub. No.: WO2015/031756
PCT Pub. Date: Mar. 5, 2015

(65) Prior Publication Data
US 2016/0199310 A1 Jul. 14, 2016

Related U.S. Application Data

(60) Provisional application No. 61/919,003, filed on Dec. 20, 2013, provisional application No. 61/872,294, filed on Aug. 30, 2013.

(51) Int. Cl.
| A61K 31/06 | (2006.01) |
| A61K 9/00 | (2006.01) |
| A61K 9/50 | (2006.01) |
| A61K 45/06 | (2006.01) |

(52) U.S. Cl.
CPC ............ *A61K 31/06* (2013.01); *A61K 9/0053* (2013.01); *A61K 9/501* (2013.01); *A61K 9/5026* (2013.01); *A61K 9/5042* (2013.01); *A61K 9/5047* (2013.01); *A61K 45/06* (2013.01)

(58) Field of Classification Search
CPC ...... A61K 31/06; A61K 45/06; A61K 9/0053; A61K 9/501; A61K 9/5026; A61K 9/5042; A61K 9/5047; A61P 3/00; A61P 29/00; A61P 25/02; A61P 25/00; A61P 1/16; A61P 3/04; A61P 35/00; A61P 3/06; A61P 39/06; A61P 43/00; A61P 5/50; A61P 3/10
See application file for complete search history.

(56) References Cited

U.S. PATENT DOCUMENTS

| 2,183,589 A | 12/1939 | Reichstein |
| 3,081,224 A | 3/1963 | Thorson et al. |
| 3,419,620 A | 12/1968 | Heinz-Manfred et al. |
| 4,695,656 A | 9/1987 | Reh et al. |
| 5,851,546 A | 12/1998 | Mashelkar et al. |
| 5,866,514 A | 2/1999 | Sugisawa et al. |
| 6,664,297 B1 | 12/2003 | Ferreira et al. |
| 2008/0234352 A1* | 9/2008 | Fischer ................ A61K 9/0004 514/411 |
| 2010/0056643 A1* | 3/2010 | Bachynsky ............ A61K 31/00 514/728 |
| 2012/0022054 A1 | 1/2012 | Benarous et al. |
| 2012/0094898 A1 | 4/2012 | Asami et al. |
| 2012/0277286 A1* | 11/2012 | Youle ................. G01N 33/5079 514/44 A |

FOREIGN PATENT DOCUMENTS

| CA | 774573 A | 12/1967 |
| WO | 9955774 A1 | 11/1999 |
| WO | 2004041256 A2 | 5/2004 |

OTHER PUBLICATIONS

European Search Report for European Patent Application No. 14839060.2 dated Mar. 1, 2017.
De Felice, et al., "Novel neuroprotective, neuritogenic and anti-amyloidogenic properties of 2,4-dinitrophenol: The gentle face of Janus", IUBMB Life. 58(4), 2006, 185-191.
Gruber, et al., "Mitochondria-targeted antioxidants and metabolic modulators as pharmacological interventions", Biotechnol Adv. 31(5), 2013, 563-592.
Harper, et al., "Mitochondrial uncoupling as a target for drug development for the treatment of obesity", Obes Rev. 2(4), 2001, 255-265.
Marrache, et al., "Engineering of blended nanoparticle platform for delivery of mitochondria-acting therapeutics", Proc Natl Acad Sci U S A. 109(40), 2012, 16288-16293.
Perry, et al., "Controlled-release mitochondrial protonophore reverses diabetes and steatohepatitis in rats", Science. 347(6227), 2015, 1253-1256.
Perry, et al., "Reversal of Hypertriglyceridemia, Fatty Liver Disease, and Insulin Resistance by a Liver-Targeted Mitochondrial Uncoupler", Cell Metab. 18(5), 2013, 740-748.
Perry, et al., "Supplementary Material (pp. 1 to 29) for Controlled-release mitochondrial protonophore reverses diabetes and steatohepatitis in rats", Science 347(6227), 2015, 1253-1256.
PCT International Search Report and Written Opinion for PCT International Application No. PCT/US2014/053406 dated Nov. 24, 2014.
"Addendum to the Toxicological Profile for Dinitrophenols", Agency for Toxic Substances and Disease Registry Division of Toxicology and Environmental Medicine, Mar. 2011.
Cohen, et al., "Trace determination of phenols by gas chromatography as their 2,4-dinitrophenyl ethers", Journal of Chromatography A 44, 1969, 251-255.

(Continued)

*Primary Examiner* — Snigdha Maewall
(74) *Attorney, Agent, or Firm* — Saul Ewing Arnstein & Lehr LLP; Kathryn Doyle; Domingos J. Silva

(57) ABSTRACT

The present invention includes a low dose and sustained release formulation of 2,4-dinitrophenol (DNP). The compositions of the invention are useful for preventing or treating a disease or disorder, such as non-alcoholic fatty liver disease, non-alcoholic steatohepatitis, insulin resistance and/or diabetes, in a subject in need thereof.

37 Claims, 52 Drawing Sheets

(56) References Cited

OTHER PUBLICATIONS

Grundlingh, et al., "2,4-dinitrophenol (DNP): a weight loss agent with significant acute toxicity and risk of death", J Med Toxicol. 7(3), Sep. 2012, 205-212.
Harris, et al., "Toxicological Profile for Dinitrophenols", U.S. Department of Health and Human Services Public Health Service Agency for Toxic Substances and Disease Registry, Aug. 1995.
Samuel, et al., "Mechanism of hepatic insulin resistance in non-alcoholic fatty liver disease", J Biol Chem. 279(31), Jul. 30, 2004, 32345-32353.
"Guidance for Industry Estimating the Maximum Safe Starting Dose in Initial Clinical Trials for Therapeutics in Adult Healthy Volunteers," U.S. Department of Health and Human Services, Food and Drug Administration, Center for Drug Evaluation and Research ,2005 ,1-27.
Robert, et al.,"Plasma levels and kinetic disposition of 2,4-dinitrophenol and its metabolites 2-amino-4-nitrophenol and 4-amino-2-nitrophenol in the mouse", J Chromatogr. 344 ,Nov. 1985 ,177-186.
Office Action dated Jul. 24, 2020 issued for European Patent Application No. 14839060.2.
Blaikie , et al., "Targeting dinitrophenol to mitochondria: limitations to the development of a self-limiting mitochondrial protonophore", Biosci Rep. 26(3), Jun. 2006, 231-243.

\* cited by examiner

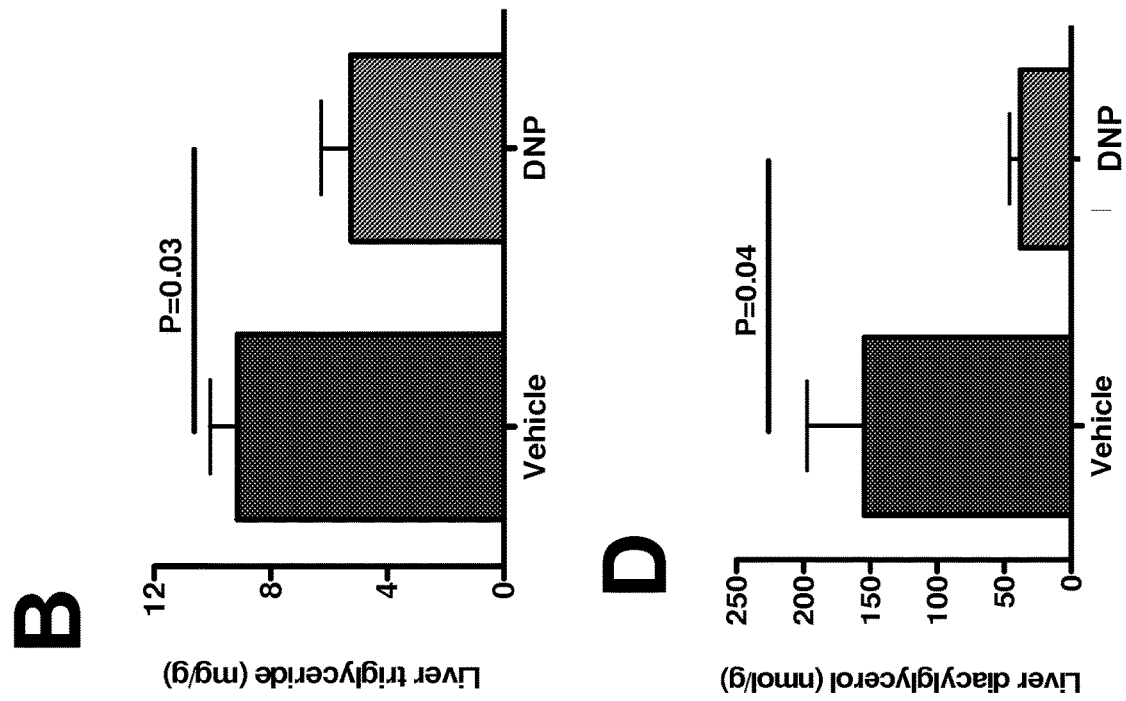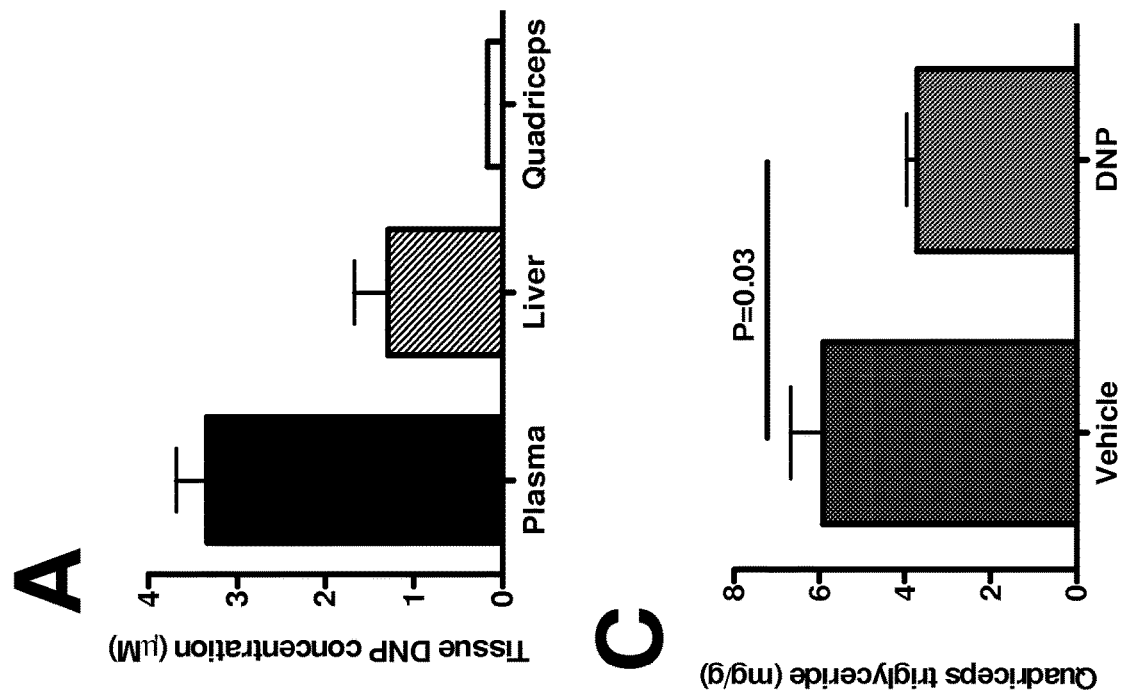
Figs. 2A-2D

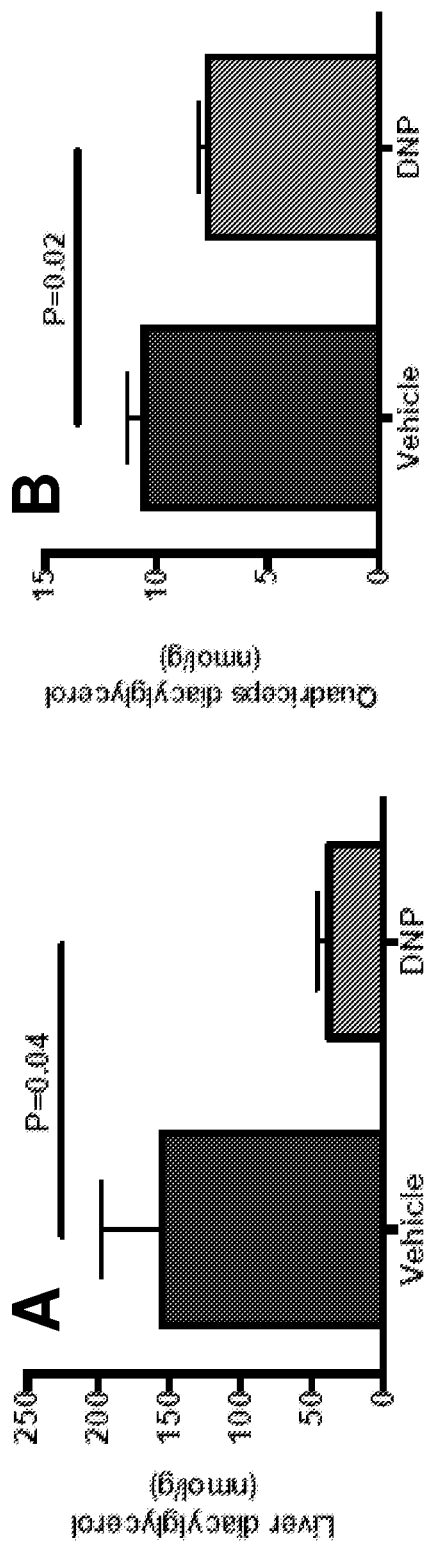
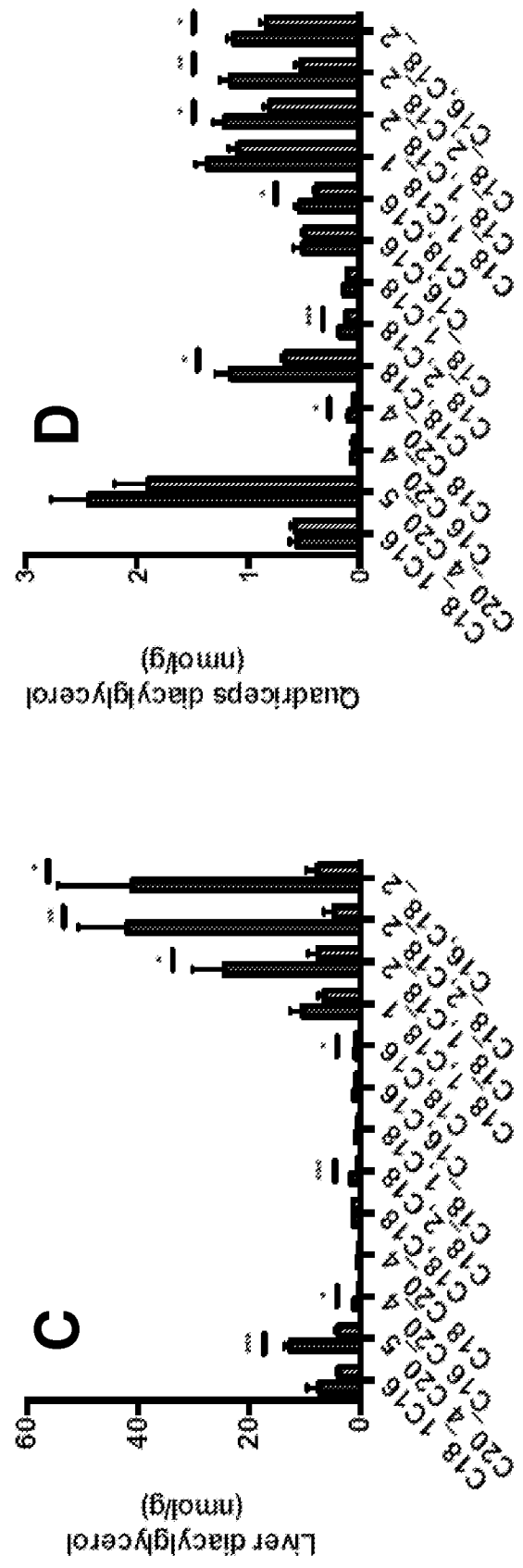
Figs. 14A-14D

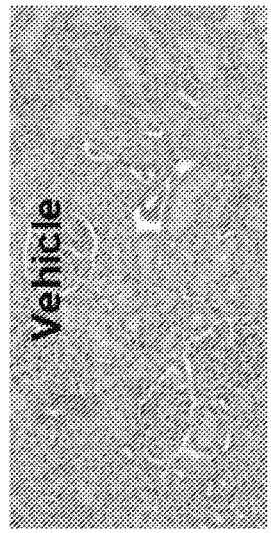
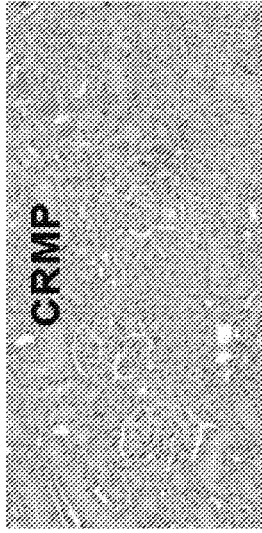
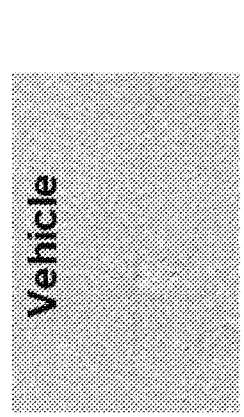
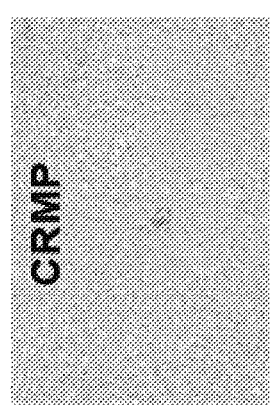
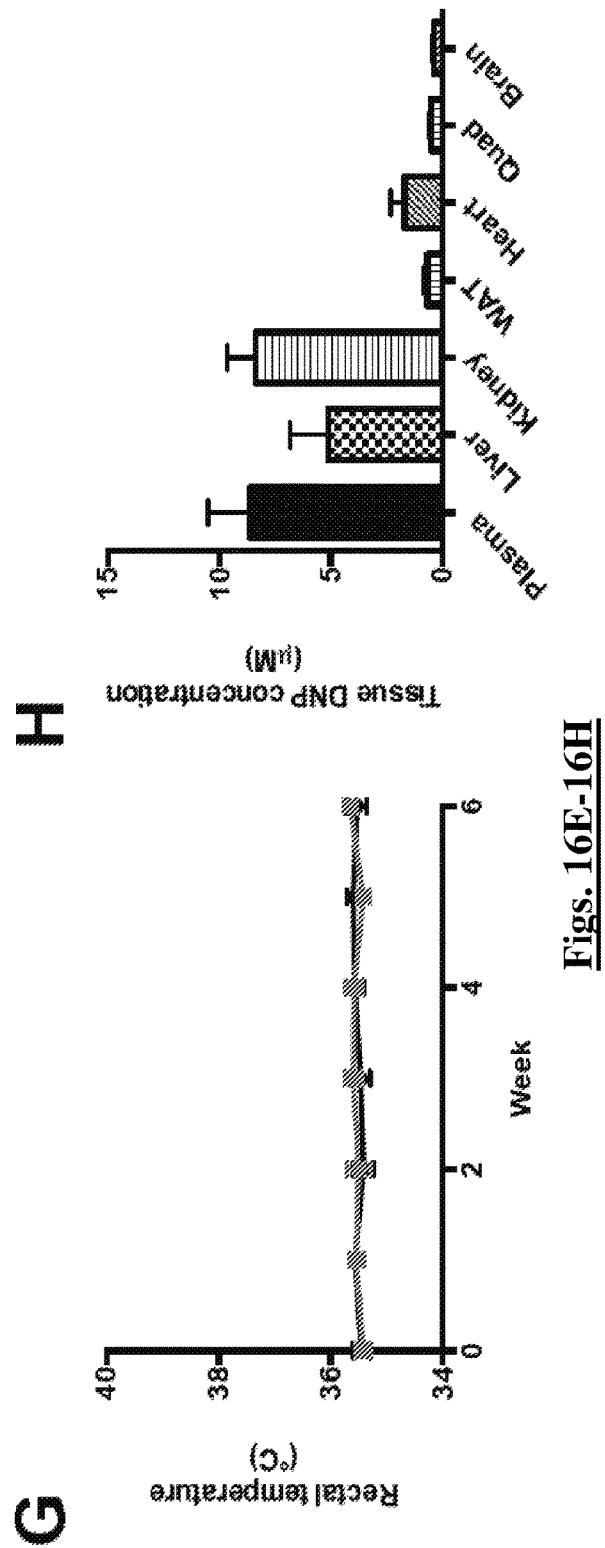
Figs. 16E-16H

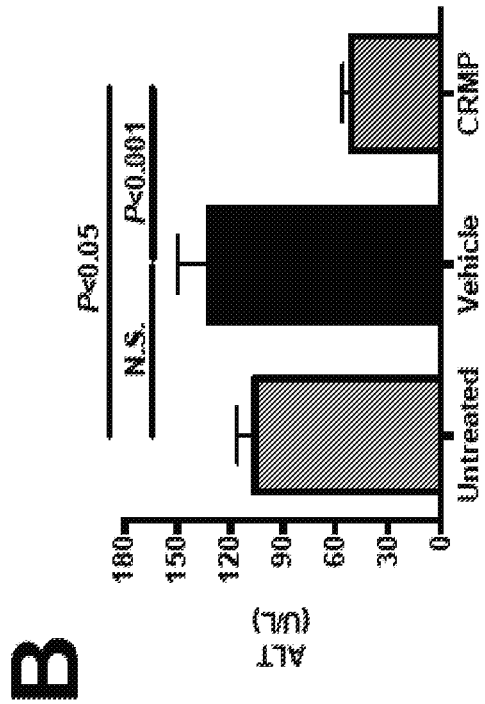
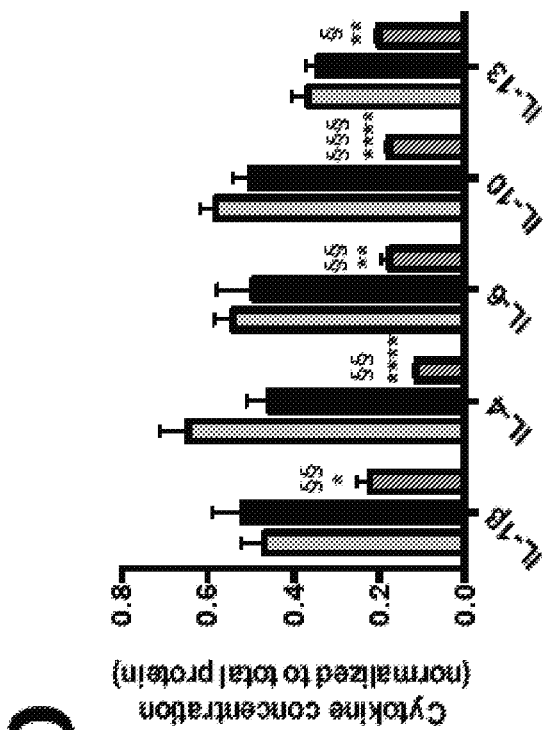
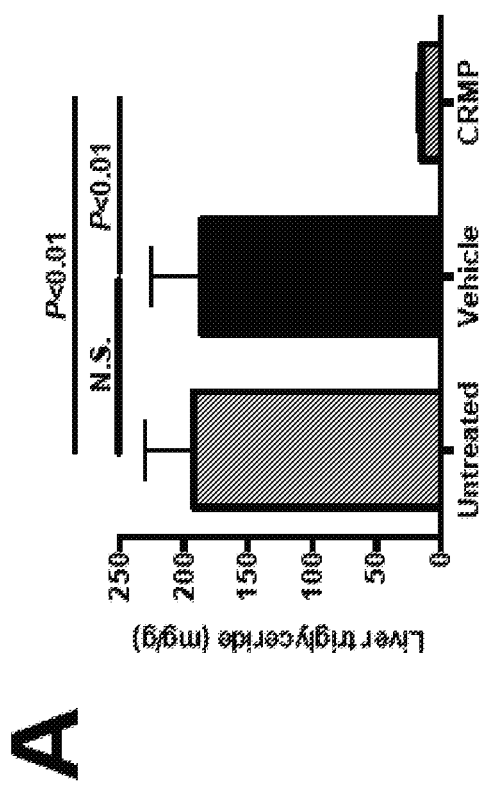
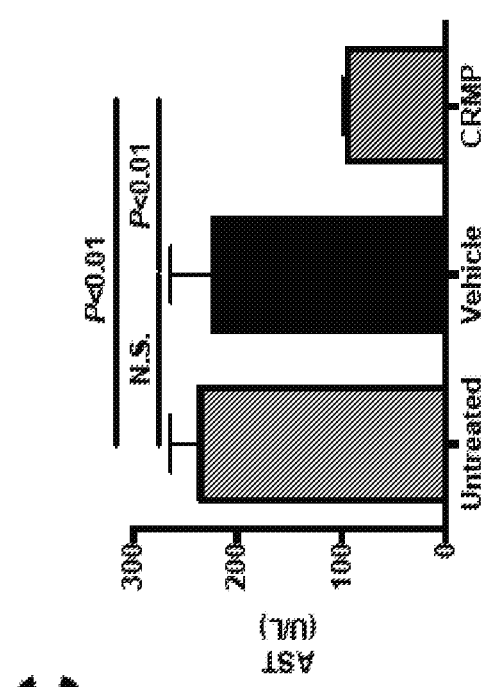
Figs. 20A-20F

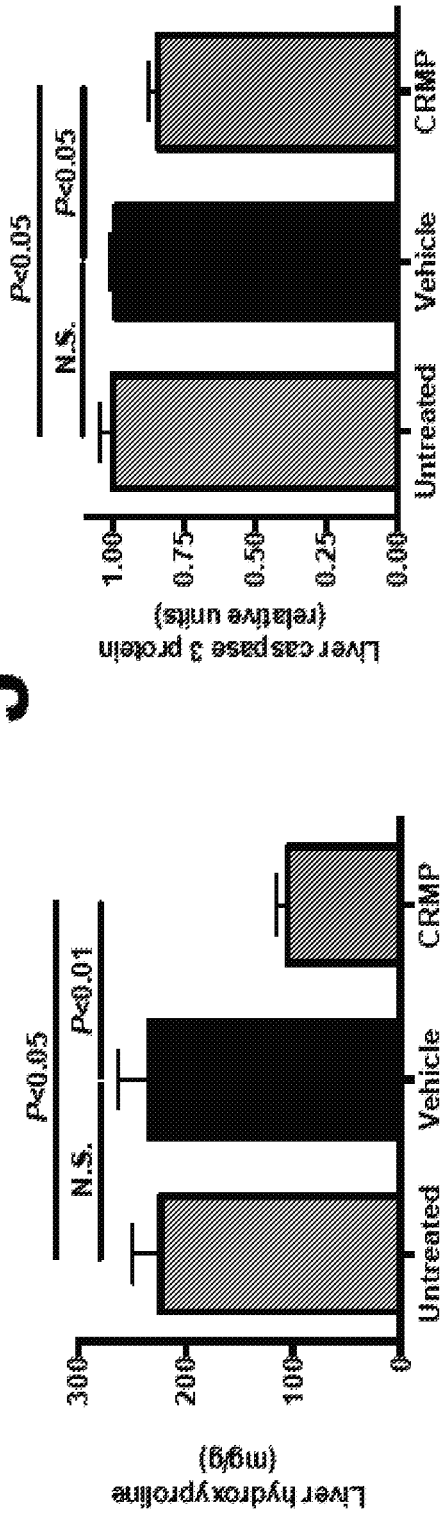
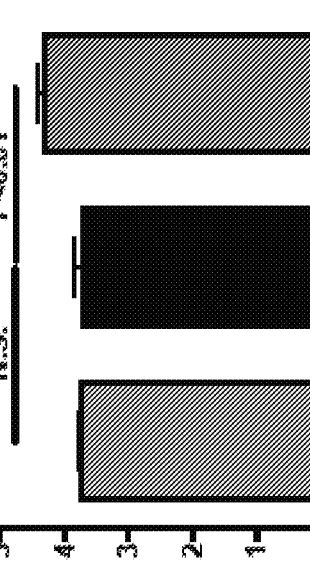
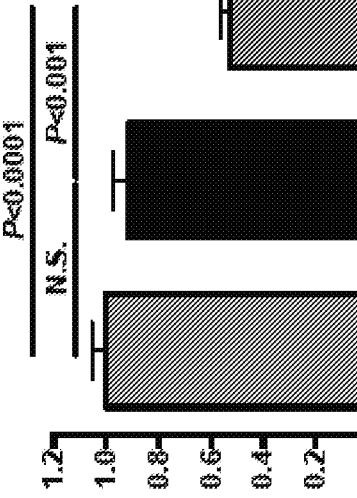
Figs. 20I-20L

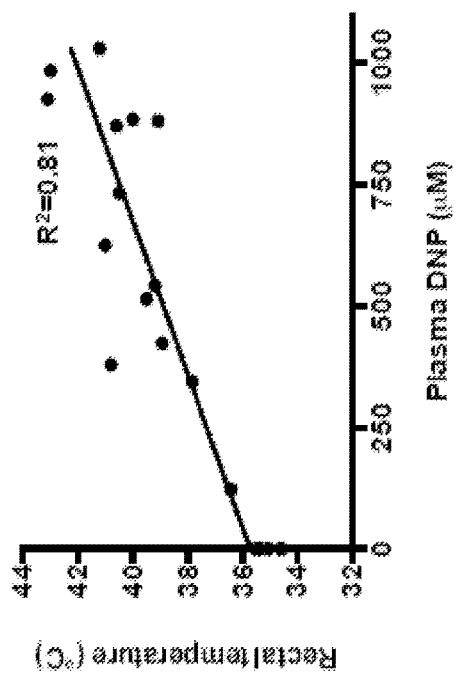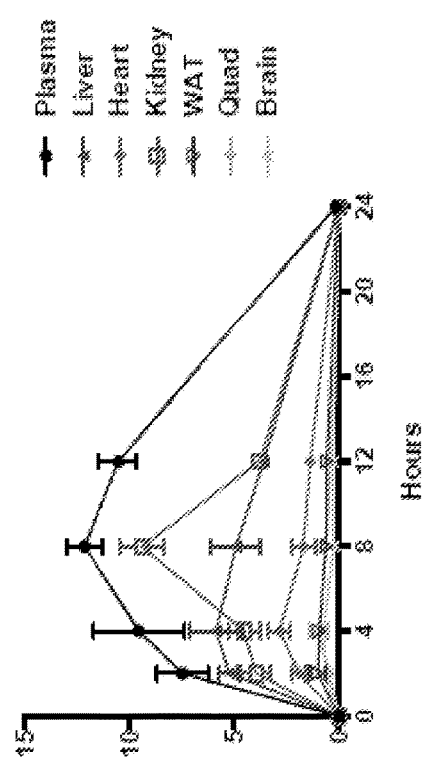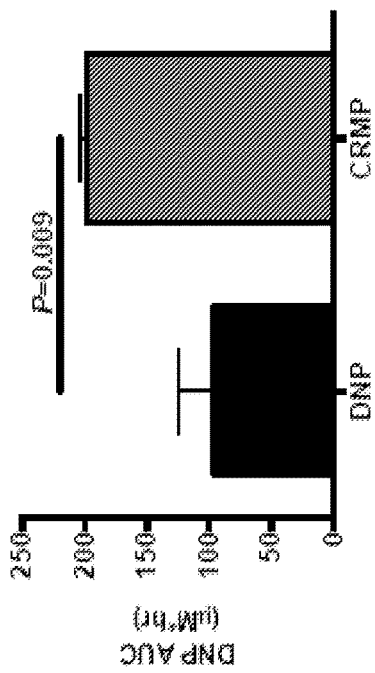
Figs. 21E-21H

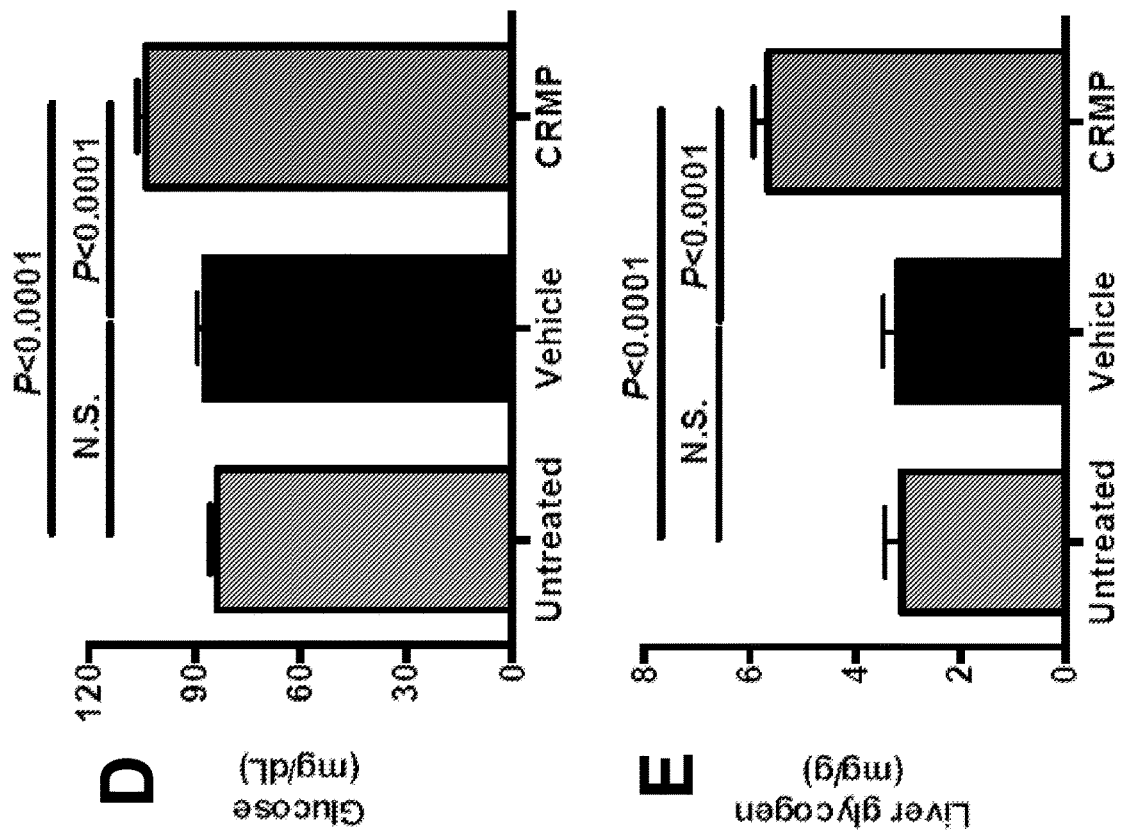
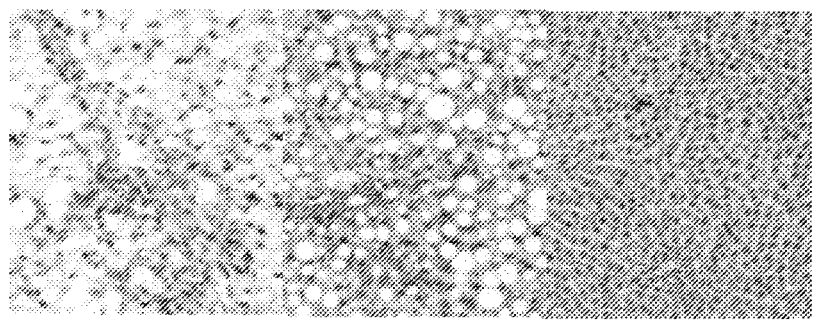
Figs. 24C-24E

2,4-DINITROPHENOL FORMULATIONS AND METHODS USING SAME

CROSS-REFERENCE TO RELATED APPLICATIONS

The present application is a 35 U.S.C. § 371 national phase application from, and claims priority to, International Application No. PCT/US2014/053406, filed Aug. 29, 2014, and published under PCT Article 21(2) in English, which claims priority under 35 U.S.C. § 119(e) to U.S. Provisional Application No. 61/872,294, filed Aug. 30, 2013 and U.S. Provisional Application No. 61/919,003, filed Dec. 20, 2013, all of which applications are incorporated herein by reference in their entireties.

STATEMENT REGARDING FEDERALLY SPONSORED RESEARCH OR DEVELOPMENT

This invention was made with government support under DK085638, DK040936 and DK049230 awarded by National Institutes of Health. The government has certain rights in the invention.

BACKGROUND OF THE INVENTION

Non-alcoholic fatty liver disease (NAFLD) is a key factor in the pathogenesis of type 2 diabetes (T2D) and affects one in three Americans (Shulman, 2000, J. Clin. Invest. 106: 171-176; Petersen, et al., 2005, Diabetes 54:603-608; Samuel & Shulman, 2012, Cell 148:852-857; Boyle, et al., 2010, Popul. Health. Metr. 8:29). NAFLD is also a key predisposing factor for the development of non-alcoholic steatohepatitis (NASH), cirrhosis and hepatocellular carcinoma. Further, NAFLD-induced NASH may soon surpass hepatitis C and alcoholic cirrhosis as the most common indication for liver transplantation in the USA (Sanyal, et al., 2010, Oncologist 15 Suppl. 4:14-22; Stickel & Hellerbrand, 2010, Gut 59:1303-1307; Barry, et al., 2010, J. Hepatol. 56:1384-1391; White, et al., 2012, Clin. Gastroenterol. Hepatol. 10:1342-1359). Thus, new and effective therapies for treatment of NAFLD are urgently needed.

One of the best characterized mitochondrial uncoupling agents is 2,4-dinitrophenol (DNP), a protonophore that shuttles protons across the mitochondrial membrane, dissipating the mitochondrial proton gradient and promoting heat dissipation of the energy derived from mitochondrial substrate oxidation. DNP was extensively used as a weight loss remedy in the 1930s but taken off the market by the U.S. Food and Drug Administration in 1938 due to the occurrence of fatal hyperthermia (Tainter, et al., 1934, Am. J. Public Health Nations Health 24:1045-1053).

There is a need in the art for compositions useful for treating NAFLD and other diseases and disorders. The present invention addresses this unmet need.

BRIEF SUMMARY OF THE INVENTION

The invention provides a method of preventing or treating a disease or disorder in a subject in need thereof. The invention further provides a method of increasing energy expenditure in a subject in need thereof. The invention further provides a therapeutically effective amount of a pharmaceutically composition comprising a compound selected from the group consisting of 2,4-dinitrophenol (DNP), a salt thereof, a solvate thereof, and any combinations thereof, wherein the compound is in a sustained release formulation.

In certain embodiments, the method comprises administering to the subject a therapeutically effective amount of a pharmaceutical composition comprising a compound selected from the group consisting of DNP, a salt thereof, a solvate thereof, and any combinations thereof.

In certain embodiments, the disease or disorder is at least one selected from the group consisting of non-alcoholic fatty liver disease (NAFLD), non-alcoholic steatohepatitis (NASH), hepatic steatosis, type 2 diabetes (T2D), acquired lipodystrophy, inherited lipodystrophy, partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma.

In certain embodiments, the subject is afflicted with at least one disease or disorder selected from the group consisting of NAFLD, NASH, hepatic steatosis, T2D, acquired lipodystrophy, inherited lipodystrophy, partial lipodystrophy, hypertriglyceridemia, obesity, metabolic syndrome, Rett's syndrome, metabolic syndrome associated with aging, metabolic diseases associated with increased ROS, Friedreich's ataxia, insulin resistance, hepatic fibrosis, liver cirrhosis and hepatocellular carcinoma.

In certain embodiments, the therapeutically effective dose of the compound ranges from about 1 mg/kg/day to about 10 mg/kg/day. In other embodiments, administration of the composition affords a steady state plasma concentration of the compound ranging from about 0.05 µM to about 200 µM in the subject. In yet other embodiments, administration of the composition affords a steady state plasma concentration of the compound ranging from about 0.5 µM to about 50 µM in the subject. In yet other embodiments, administration of the composition affords a steady state plasma concentration of the compound ranging from about 3 µM to about 5 µM in the subject.

In certain embodiments, the steady state plasma concentration of the compound in the subject is about 50 to about 100 times lower than the toxic concentration of the compound in the subject. In other embodiments, administration of the composition affords therapeutically effective levels of the compound in the subject for a period of time ranging from about 12 hours to about 24 hours.

In certain embodiments, the composition is administered once, twice or three times a day to the subject. In other embodiments, administration of the composition does not cause significant systemic toxicity or significant increase in body temperature in the subject. In yet other embodiments, the significant systemic toxicity is indicated by increase in levels of liver enzymes, blood urea nitrogen or creatinine as compared to the corresponding levels in the subject in the absence of administration of the composition. In yet other embodiments, the composition is formulated for oral administration.

In certain embodiments, the subject is further administered at least one additional therapeutic agent. In other embodiments, the composition and the at least one additional therapeutic agent are co-administered to the subject. In yet other embodiments, the composition and the at least one additional therapeutic agent are co-formulated.

In certain embodiments, the subject is a mammal. In other embodiments, the mammal is human.

In certain embodiments, administration of the amount of the composition to a subject affords a steady state plasma concentration of the compound ranging from about 0.05 µM to about 200 µM in the subject. In other embodiments, administration of the amount of the composition to a subject affords a steady state plasma concentration of the compound ranging from about 0.5 µM to about 50 µM in the subject. In yet other embodiments, administration of the amount of the composition to a subject affords a steady state plasma concentration of the compound ranging from about 3 µM to about 5 µM in the subject. In yet other embodiments, the steady state plasma concentration of the compound in the subject is about 50 to about 100 times lower than the toxic concentration of the compound in the subject. In yet other embodiments, administration of the amount of the composition affords therapeutically effective levels of the compound in the subject for a period of time ranging from about 12 hours to about 24 hours. In yet other embodiments, the amount of the composition is administered once, twice or three times a day to the subject.

In certain embodiments, administration of the amount of the composition does not cause significant systemic toxicity or significant increase in body temperature in the subject. In other embodiments, the significant systemic toxicity is indicated by increase in levels of liver enzymes, blood urea nitrogen or creatinine, as compared to the corresponding levels in the subject in the absence of administration of the composition. In yet other embodiments, the composition is formulated for oral administration. In yet other embodiments, the composition further comprises at least one additional therapeutic agent.

In certain embodiments, the compound in the composition is coated with a coating comprising at least one selected from the group consisting of hydroxypropylcellulose and ethylcellulose. In other embodiments, the coating further comprises at least one selected from the group consisting of talc and dibutyl sebacate. In yet other embodiments, the compound is in a bead or sphere form. In yet other embodiments, the bead or sphere comprising the compound further comprises at least one selected from the group consisting of mannitol, microcrystalline cellulose and hydroxypropylmethyl cellulose.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 2, comprising FIGS. 2A-2H, illustrates the finding that low-dose intragastric infusion of DNP reduces plasma glucose, triglyceride and insulin concentrations, as well as hepatic steatosis and whole body insulin resistance, in a rat model of NAFLD and whole body insulin resistance. FIG. 2A is a graph illustrating plasma, liver, and quadriceps DNP concentrations. FIG. 2B is a graph illustrating liver triglyceride content. FIG. 2C is a graph illustrating muscle triglyceride content. FIG. 2D is a graph illustrating liver diacylglycerol content. FIG. 2E is a graph illustrating muscle diacylglycerol content. FIG. 2F is a graph illustrating fasting plasma glucose concentrations. FIG. 2G is a graph illustrating fasting plasma triglyceride concentrations. FIG. 2H is a graph illustrating fasting plasma insulin concentrations. n=3-4 per group.

FIG. 4, comprising FIGS. 4A-4B: Rectal temperature of rats treated acutely with DNP or ERDNP. FIGS. 4C-4D: Liver triacylglycerol concentration in high fat fed rats treated for 5 days with DNP or ERDNP. *P<0.05, P<0.01, *P<0.001 versus vehicle-treated group. n=3 per dose, per group.

FIG. 5, comprising FIG. 5A: Plasma concentrations after a dose of DNP (25 mg/kg, toxic dose; black circles) or ERDNP (1 mg/kg; red squares). FIG. 5B: Tissue DNP concentrations 1 hour after treatment with 25 mg/kg DNP. FIG. 5C-5D: Tissue DNP concentrations after one or five daily doses of 1 mg/kg ERDNP. FIG. 5E: Tissue DNP concentrations after 6 weeks of daily treatment with 1 mg/kg ERDNP. FIG. 5F: Tissue DNP concentrations 24 hours after ERDNP treatment. In all panels, n=3 per group.

FIG. 6, comprising FIGS. 6A-6C: Fasting plasma glucose, triglyceride and insulin concentrations. FIG. 6D: Plasma cholesterol concentrations. FIGS. 6E-6F: Plasma glucose and insulin concentrations during an IP glucose tolerance test. FIG. 6G: Fasting plasma non-esterified fatty acids concentrations. *P<0.05, P<0.01, *P<0.001. In all panels, n=6-8 per group.

FIG. 7, comprising FIG. 7A: Glucose infusion rate to maintain euglycemia in a hyperinsulinemic-euglycemic clamp. FIG. 7B: Insulin-stimulated glucose uptake in quadriceps muscle. FIG. 7C: Basal (solid bars) and insulin-stimulated (dashed bars) hepatic glucose production. FIG. 7D: Insulin-stimulated suppression of hepatic glucose production. In all panels, n=6-8 per group.

FIG. 8, comprising FIGS. 8A-8B: Liver and quadriceps triacylglycerol. FIG. 8C: Liver pyruvate carboxylase flux. FIG. 8D: Liver acetyl CoA concentration. FIG. 8E: Hepatic tricarboxylic acid cycle (TCA) cycle flux supplied by carbons from fatty acid oxidation (solid bars) and through PDH flux (dashed bars). FIG. 8F: Hepatic triglyceride export. n=6 per group.

FIG. 9, comprising FIG. 9A: Random plasma glucose concentrations in vehicle-treated (black circles) and ERDNP-treated rats (red squares). FIGS. 9B-9D: Fasting plasma glucose, triglyceride and insulin concentrations. FIGS. 9E-9F: Glucose and insulin concentrations during an intraperitoneal glucose tolerance test. FIGS. 9G-9H: ALT and AST concentrations.

FIG. 11, comprising FIG. 11A is a graph illustrating liver TAG content. FIG. 11B is a graph illustrating quadriceps TAG content. Rats were fasted for 6 hours. ERDNP oral dosing (1 mg/kg every 12 hours) for 5 days resulted in significant reductions in liver triglyceride concentrations and a strong tendency for reductions in muscle triglyceride content in a high fat fed rat model of insulin resistance and NAFLD.

FIG. 14, comprising FIGS. 14A-14L, illustrates the finding that chronic, intragastric DNP infusion (2 mg/kg per day) safely reverses NAFLD in rats. FIGS. 14A-14B: Liver and quadriceps diacylglycerol. FIGS. 14C-14D: Liver and quadriceps DAG species. FIGS. 14E-14F: Liver and quadriceps ceramides. FIGS. 14G-14J: ALT, AST, BUN, and creatinine concentrations. FIG. 14K: Body weight before and after treatment. FIG. 14L: Daily caloric intake during the treatment period. n=4 per group.

FIG. 15, comprising FIGS. 15A-15B: ALT in rats treated with varying doses of DNP or ERDNP for 5 days. FIGS. 15C-15D: AST in rats treated with varying doses of DNP or ERDNP for 5 days. FIGS. 15E-15F: BUN in rats treated with varying doses of DNP or ERDNP for 5 days. FIGS. 15G-15H: Creatinine in two-week high fat fed rats treated with varying doses of DNP for five days. n=3 per dose, per group.

FIG. 16, comprising FIGS. 16A-16H, illustrates the finding that six weeks of ERDNP treatment (1 mg/kg per day) is well tolerated in rats. FIGS. 16A-16D: ALT, AST, BUN, and creatinine. FIGS. 16E-16F: Representative images of liver and kidney, respectively, stained with hematoxylin and eosin. FIG. 16G: Rectal temperature. FIG. 16H: Tissue DNP concentrations 8 hours after the last dose of ERDNP. In all panels, n=3-6 per group.

FIG. 17, comprising FIG. 17A: Body weight at the end of the treatment period. FIG. 17B: Non-esterified free fatty acid concentration. FIG. 17C: Western blots. FIGS. 17D-17F: Pyruvate carboxylase, glucose-6-phosphatase, and fructose-1,6-bisphosphatase protein. FIGS. 17G-17H: Plasma glucose and insulin area under the curve in an IP glucose tolerance test. In all panels, n=6-8 per group. FIG. 17I: Ratio of fat oxidation to TCA cycle flux. Black bars, vehicle; red/gray bars, ERDNP. FIG. 17J: White adipose tissue weight. FIG. 17K: Plasma cholesterol. Black bars, vehicle; red/gray bars, ERDNP.

FIG. 18, comprising FIG. 18A: Plasma insulin concentrations at the end of a 120 min hyperinsulinemic-euglycemic clamp. FIG. 18Z: Insulin-stimulated glucose uptake in brown adipose tissue. Unless otherwise stated, n=6-8 per group.

FIG. 19, comprising FIG. 19A: Body weight before and after treatment with vehicle (black bars) or ERDNP (red bars). FIGS. 19B-19C: Glucose and insulin area under the curve in the IP glucose tolerance test. FIGS. 19D-19E: Liver and quadriceps TAG concentrations. FIGS. 19F-19I: ALT, AST, BUN, and creatinine concentrations. FIGS. 19J-19K: Liver acetyl and malonyl CoA concentrations. FIG. 19L: Hepatic acetyl CoA concentration. In all panels, n=6-7 per group.

FIG. 20, comprising FIGS. 20A-20L, illustrates the finding that oral ERDNP (1 mg/kg per day) ameliorates NASH and improves liver synthetic function in methionine/choline deficient rats. FIG. 20A: Liver triglyceride content. FIGS. 20B-20C: Plasma AST and ALT concentrations. FIG. 20D: Liver inflammatory cytokine concentrations, normalized to total protein. n=4 per group. FIG. 20E: Liver histology. FIG. 20F: Fibrosis score. FIG. 20G: Liver collagen mRNA expression. FIG. 20H: Liver smooth muscle actin protein. FIG. 20I: Hepatic hydroxyproline content. FIGS. 20J-20K: Liver caspase 3 and caspase 9 protein. FIG. 20L: Plasma albumin concentrations. Unless otherwise specified, n=6-8 per group.

FIG. 21, comprising FIGS. 21-21L, illustrates the finding that ERDNP is better tolerated than DNP because it results in lower plasma and tissue DNP concentrations. FIG. 21E: 24 hour area under the curve of plasma DNP concentrations after treatment with 1 mg/kg oral DNP (n=4) or ERDNP (n=9). FIG. 21F: Correlation between rectal temperature and plasma DNP concentration in rats treated with 10-50 mg/kg DNP. FIG. 21G: Tissue DNP concentrations 1 hour after treatment with 25 mg/kg DNP. n=3. FIG. 21H: Tissue DNP concentrations 8 hours after one dose of 1 mg/kg orally administered ERDNP. n=3. FIG. 21I: Plasma:tissue DNP ratio at various time points following 1 mg/kg oral ERDNP. n=3. FIG. 21J: Tissue DNP concentrations 8 hours after the last of five daily 1 mg/kg ERDNP doses. n=3. FIG. 21K: Linear correlations between oral ERDNP dose and tissue DNP concentrations measured 8 hours after dosing. n=3. FIG. 21L: Plasma DNP concentrations after one dose and the last of five daily 1 mg/kg ERDNP doses. Data for treatment-naïve rats are copied from FIG. 21C. n=4 for rats treated chronically.

FIG. 22, comprising FIGS. 22A-22C: Fasting plasma glucose, NEFA and insulin concentrations. FIGS. 22D-22F: Liver, plasma, and quadriceps triglyceride content. n=8 per group.

FIG. 23, comprising FIG. 23A: Oxygen consumption ($V_{O2}$). FIG. 23B: Carbon dioxide production ($V_{CO2}$). FIG. 23C: Respiratory quotient. FIG. 23D: Activity over the course of the day. FIG. 23E: Energy expenditure throughout the day. FIG. 23F: Total daily water drinking. FIG. 23G: Total daily food intake. FIG. 23H: Food intake over the course of the day. *$P<0.05$, **$P<0.01$. n=8 per group.

FIG. 24, comprising FIGS. 24A-24E, illustrates the finding that six weeks of daily ERDNP treatment (1 mg/kg per day) ameliorates NASH and improves liver synthetic function in methionine/choline deficient rats. FIG. 24A: Liver inflammatory cytokine protein content, normalized to total protein. FIG. 24B: Hepatic CD69 protein. FIG. 24C: Livers stained for TUNEL positive cells (brown stain). FIG. 24D: Fasting plasma glucose concentrations. FIG. 24E: Liver glycogen content. n=6-8 per group.

DETAILED DESCRIPTION OF THE INVENTION

Figure 1:
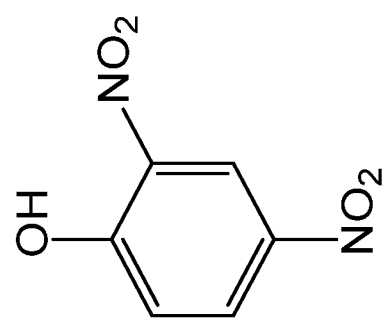
FIG. 1 illustrates the structure of 2,4-dinitrophenol (DNP).

The invention relates to the unexpected discovery that a low, sustained dose of 2,4-dinitrophenol (DNP), or a salt or solvate thereof, or any combinations thereof, provides reductions in hepatic steatosis, improved insulin sensitivity, improved glucose tolerance, reduced blood glucose and/or reversal in liver inflammation, without causing hyperthermia and systemic toxicities.

In certain embodiments, the compositions of the invention are useful in treating or preventing at least one disease or disorder selected from the group consisting of non-alcoholic fatty liver disease (NAFLD), non-alcoholic steatohepatitis (NASH), hepatic steatosis, type 2 diabetes (T2D), acquired lipodystrophy, (inherited) lipodystrophy, partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma. In other embodiments, the compositions of the invention are useful in managing, maintaining, and/or preventing the increase of, the weight of a subject. In yet other embodiments, the compositions of the invention are useful in reducing the weight of a subject.

In one aspect, the studies described herein demonstrate that the systemic toxicities of a mitochondrial protonophore (such as DNP) may be dissociated from its ability to promote hepatic mitochondrial uncoupling and increase hepatic fat oxidation by altering its pharmacokinetics. The findings described herein should not be construed to be limited to extended release formulations of 2,4-DNP, but rather are applicable to extended release formulations of any known and useful mitochondrial protonophore or analogue/derivative thereof, such as but not limited to any isomers and/or analogues of 2,4-DNP (e.g., beta-2,4-DNP and 2,6-dinitrophenol), carbonyl cyanide m-chlorophenyl hydrazine (CCCP) and carbonylcyanide p-trifluoromethoxyphenylhydrazone (FCCP).

As described herein, the safety and efficacy of a novel extended release oral formulation of DNP (ERDNP) on hepatic steatosis, insulin resistance and diabetes was studied in rat models of NAFLD and T2D. Such models achieved sustained plasma concentrations of DNP (1 to 10 μM over 24 hours), which are 50-100 fold lower than the toxic threshold for DNP. In a non-limiting embodiment, low concentrations of DNP (1-5 μM) were found to promote subtle increases in hepatic mitochondrial uncoupling while remaining well below the toxic plasma threshold of DNP (~400 μM).

ERDNP was found to have a therapeutic index that was 500-fold greater than DNP. Chronic ERDNP treatment reduced hypertriglyceridemia, hepatic steatosis, insulin resistance and diabetes in rat models of NAFLD and T2D. Further, ERDNP normalized plasma transaminase concentrations, ameliorated liver fibrosis, and improved hepatic protein synthetic function as reflected by an increase in plasma albumin concentrations in a methionine/choline deficient rat model of NASH. Further, chronic ERDNP was well tolerated and not associated systemic toxicities. These data indicates that ERDNP may be used in treating related epidemics of T2D, NASH, hepatic fibrosis and metabolic syndrome.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "abnormal," when used herein in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

As used herein, the term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" or "treated" if the severity of a symptom of the disease or disorder, the frequency with which such a symptom is experienced by a patient, or both, is reduced.

As used herein, the term "ALT" refers to alanine aminotransferase.

As used herein, the term "AST" refers to aspartate aminotransferase.

As used herein, the term "BUN" refers to blood urea nitrogen.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

A used herein, the term "CRMP" refers to controlled-release oral formulation of a mitochondrial protonophore. As used herein, the terms "ERDNP" and "CRMP" are used interchangeably.

As used herein, the term "DAG" refers to diacylglycerol.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "DNP" and "2,4-DNP" refer to 2,4-dinitrophenol, or a salt or solvate thereof, or any combinations thereof (FIG. 1).

An "effective amount" of a delivery vehicle is that amount sufficient to effectively bind or deliver a compound.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "ERDNP" refers to extended release 2,4-dinitrophenol, or a salt or solvate thereof, or any combinations thereof.

As used herein, the term "LC/MS/MS" refers to liquid chromatography/mass spectrometry/mass spectrometry.

As used herein, the term "NAFLD" refers to non-alcoholic fatty liver disease.

As used herein, the term "NMR" refers to nuclear magnetic resonance.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, individual or subject is human.

As used herein, the term "PC" refers to pyruvate carboxylase.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "PKCε" refers to protein kinase CE.

As used herein, the term "PKCθ" refers to protein kinase CO.

As used herein, the term "potency" refers to the dose needed to produce half the maximal response ($ED_{50}$).

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "significant increase in body temperature" in a subject refers to a body temperature increase that is associated with deleterious effects on the subject, not limited to illness, physical discomfort or pain, coma and death. In one non-limiting embodiment, the significant increase in body temperature is an increase of about 0.5° C., about 1° C., about 1.5° C., about 2° C., about 2.5° C., about 3° C., about 3.5° C., about 4° C., about 4.5° C., about 5° C., about 5.5° C., about 6° C. or higher. In another non-limiting embodiment, the significant increase in body temperature lasts for about 5 min, about 15 min, about 30 min, about 45 min, about 1 h, about 1.5 h, about 2 h, about 3 h, about 4 h, about 5 h, about 6 h, about 7 h, about 8 h, about 9 h, about 10 h, about 12 h, about 14 h, about 16 h, about 18 h, about 20 h, about 22 h, about 24 h or longer.

As used herein, the term "significant systemic toxicity" in a subject refers to systemic toxicity that is associated with deleterious effects on the subject, not limited to illness, physical discomfort or pain, coma and death. In one non-limiting embodiment, significant systemic toxicity is indicated by increase in levels of liver enzymes, blood urea nitrogen or creatinine as compared to the corresponding levels in the subject in the absence of administration of the composition.

As used herein, the term "TAG" refers to triacylglycerol.

As used herein, the term "T2D" refers to type 2 diabetes.

As used herein, the term "TCA" refers to tricarboxylic acid cycle.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "VLDL" refers to very low-density lipoprotein.

As used herein, the term "WAT" refers to white adipose tissue.

As used herein, the term "ZDF" refers to Zucker Diabetic Fatty.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the unexpected discovery that a low, sustained dose of DNP reduces hepatic steatosis, improves insulin sensitivity, improves glucose tolerance, reduces blood glucose and/or reverses liver inflammation in a subject, without causing hyperthermia and systemic toxicities in the subject. In certain embodiments, the subject is a mammal. In yet other embodiments, the mammal is human.

The present invention relates in part to the unexpected discovery that significant hepatic mitochondrial uncoupling may be achieved by administering a very low dose continuous infusion of DNP (or any other mitochondrial protonophore) without any associated systemic toxicities, leading to increased hepatic fatty acid oxidation, decreased hepatic fat content, and reversal of hepatic and peripheral insulin resistance in a rat model of non-alcoholic fatty liver disease (NAFLD). The toxicity of DNP in prior art studies was due to the pharmacokinetics of oral DNP leading to peak plasma concentrations that were many fold greater than what is required to achieve a therapeutic effect. In view of the fact that hyperthermia and related toxicities of DNP are on-target effects related to systemic mitochondrial uncoupling, a slow release formulation of DNP is an effective and safe approach to promote the metabolism of hepatic triglyceride, while avoiding hyperthermia and associated systemic toxicities that typically occur with mitochondrial uncoupling agents.

In one aspect, the present invention contemplates the use of any mitochondrial uncoupling agent within the compositions and methods of the invention. In certain embodiments, the mitochondrial uncoupling agent comprises DNP. In yet other embodiments, the mitochondrial uncoupling agent comprises CCCP, FCCP, 2,6-dinitrophenol, or any known 2,4-DNP analog/derivative/isomer.

As demonstrated herein, sustained plasma and liver concentrations of DNP between 0.5 μM-50 μM, such as between 1-3 μM, which were achieved during a continuous low dose intragastric infusion of DNP, reversed fatty liver and whole body insulin resistance in a well-established high fat rat model of NAFLD. These plasma DNP concentrations were ~100 fold lower than the threshold where DNP toxicity is first detected. Based on these results, an extended release preparation of DNP was formulated that resulted in low sustained plasma DNP concentrations over a 24-hour interval, which in turn led to a 500-fold improvement in the ratio of toxic to effective dose of ERDNP compared to DNP.

Chronic safety and efficacy studies of ERDNP treatment were performed, chronic daily ERDNP treatment was well tolerated in rats for up to 6 weeks with no changes in behavior, body temperature, food intake, activity or body weight. Further, chronic ERDNP treatment was not associated with any systemic or liver/renal toxicities, as indicated by a lack of elevations in liver enzymes, BUN, or creatinine or deleterious changes in liver or kidney histology.

In terms to efficacy, chronic ERDNP treatment resulted in a 50% reduction in liver TAG content. This reduction in hepatic fat content could be attributed to a 60% increase in liver mitochondrial $V_{TCA}$ cycle flux, which was entirely due to a 70% increase in hepatic fat oxidation. This reduction in liver lipid content was associated with marked reductions in fasting plasma glucose concentrations, basal rates of hepatic glucose production and improvement in whole body insulin sensitivity. The reduction in basal rates of hepatic glucose production could be attributed to a 25% reduction in $V_{PC}$ flux, which was most likely secondary to a 50% reduction in concentrations of acetyl CoA, a key allosteric regulator of PC activity. In contrast, there was no effect of ERDNP treatment on hepatic PEP-CK, PC or G6Pase protein expression.

ERDNP improvement in whole body insulin sensitivity in turn could be attributed to an increase in both hepatic and muscle insulin responsiveness, as reflected by a 2.5-fold increase in suppression of hepatic glucose production during a hyperglycemic-euglycemic clamp and a three-fold increase in insulin-stimulated peripheral glucose uptake. This ERDNP induced increase in liver and muscle insulin sensitivity could be attributed to >50% reductions in liver and muscle DAG content, as well as in PKCε and PKCθ activity in liver and muscle respectively. DAG-nPKC activation is implicated in causing liver and muscle insulin resistance in both humans and animal models of NAFLD. The observed ERDNP reduction in TAG/DAG content could be attributed at least in part to an 80% reduction in hepatic VLDL export. Without wishing to be bound by any theory, while ERDNP may promote mitochondrial uncoupling in skeletal muscle, the fact that 20-fold higher DNP concentrations did not cause significant mitochondrial uncoupling in the quadriceps makes this possibility less likely.

The safety and efficacy of ERDNP were examined in ZDF rats, a model of T2D associated with NASH. Two weeks of ERDNP treatment resulted in a 65% reduction in liver fat content and reversal of hepatic inflammation as reflected by normalization of plasma ALT and AST in these animals, highlighting a possible role for ERDNP in reversing NASH. In addition, ERDNP caused a 400 mg/dL reduction in fasting plasma glucose concentrations in ZDF rats, which could be attributed to marked improvements in whole body insulin sensitivity as reflected by lower plasma glucose and insulin concentrations during an intraperitional glucose tolerance test. Consistent with the lack of systemic toxicities observed in the other animal studies, chronic ERDNP treatment in ZDF rats was well tolerated and caused no alterations in behavior, body temperature, feeding behavior, body weight, or activity and was unassociated with any changes in renal function.

In one aspect, the present studies indicate that, by altering the pharmacokinetics of DNP to promote a low sustained systemic release, the therapeutic window of DNP is increased by more than 500-fold. Chronic ERDNP administration reversed NAFLD/NASH, insulin resistance, and type 2 diabetes in the rat without any systemic, hepatic or renal toxicity. Taken together, these data support the utility of ERDNP for the treatment of the related epidemics of NAFLD/NASH, metabolic syndrome and type 2 diabetes.

The compositions of the invention, which include therapeutic low dose, sustained release formulations of DNP, are useful in treating a disease or disorder, such as but not limited to non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma.

In certain embodiments, the compositions and methods of the present invention may be used to treat or prevent a disease or disorder such as, but not limited to, NAFLD, non-alcoholic steatohepatitis (NASH), hepatic steatosis, acquired lipodystrophy, inherited lipodystrophy, partial lipodystrophy, insulin resistance, type 2 diabetes (T2D), obesity, hypertriglyceridemia, metabolic syndrome, metabolic syndrome associated with aging, metabolic diseases associated with increased reactive oxygen species (ROS), Friedreich's ataxia, hepatic fibrosis, liver cirrhosis, hepatocellular carcinoma, diseases in which free radical mediated oxidative injury leads to tissue degeneration, and diseases in which cells inappropriately undergo apoptosis, and include the treatment of a wide number of diseases, including but not limited to auto-immune disease, congenital muscular dystrophy, fatal infantile myopathy, "later-onset" myopathy, MELAS (mitochondrial encephalopathy, lactic acidosis, and stroke), MIDD (mitochondrial diabetes and deafness), MERRF (myoclonic epilepsy ragged red fiber syndrome), arthritis, NARP (Neuropathy; Ataxia; Retinitis Pigmentosa), MNGIE (Myopathy and external ophthalmoplegia; Neuropathy; Gastro-Intestinal; Encephalopathy), LHON (Leber's; Hereditary; Optic; Neuropathy), Kearns-Sayre disease, Pearson's Syndrome, PEO (Progressive External Ophthalmoplegia), Wolfram syndrome, DIDMOAD (Diabetes Insipidus, Diabetes Mellitus, Optic Atrophy, Deafness), ADPD (Alzheimer's disease; Parkinson's disease), AMFD (ataxia, myoclonus and deafness), CIPO (chronic intestinal pseudoobstruction; myopathy; opthalmoplegia), CPEO (chronic progressive external opthalmoplegia), maternally inherited deafness, aminoglycoside-induced deafness, DEMCHO (dementia; chorea), DMDF (diabetes mellitus; deafness), exercise intolerance, ESOC (epilepsy; strokes; optic atrophy; congenitive decline), FBSN (familial bilateral striatal necrosis), FICP (fatal infantile cardiomyopathy plus a MELAS-associated cardiomyopathy), GER (gastrointestinal reflux), LIMM (lethal infantile mitochondrial myopathy), LDYT (Leber's hereditary optic neuropathy and DYsTonia), MDM (myopathy; diabetes mellitus), MEPR (myoclonic epilepsy; psychomotor regression), MERME (MERRF/MELAS overlap disease), MHCM (maternally inherited hypertrophic cardiomyopathy), MICM (maternally inherited cardiomyopathy), MILS (maternally inherited Leigh syndrome), mitochondrial encephalocardiomyopathy, mitochondrial encephalomyopathy, mitochondrial myopathy, MMC (maternal myopathy; cardio myopathy), multi-system mitochondrial disorder (myopathy; encephalopathy; blindness; hearing loss; peripheral neuropathy), NIDDM (non-insulin dependent diabetes mellitus), PEM (progressive encephalopathy), PME (progressive myclonus epilepsy), Rett's syndrome, SIDS (sudden infant death syndrome, SNHL (sensorineural hearing loss), Leigh's Syndrome, dystonia, schizophrenia, and psoriasis.

In certain embodiments, the disease or disorder is NAFLD. In yet other embodiments, the disease or disorder is non-alcoholic steatohepatitis (NASH). In yet other embodiments, the disease or disorder is hepatic steatosis. In yet other embodiments, the disease or disorder is type 2 diabetes. In yet other embodiments, the disease or disorder is acquired lipodystrophy. In yet other embodiments, the disease or disorder is inherited lipodystrophy. In yet other embodiments, the disease or disorder is partial lipodystrophy. In yet other embodiments, the disease or disorder is hypertriglyceridemia. In yet other embodiments, the disease or disorder is obesity. In yet other embodiments, the disease or disorder is metabolic syndrome. In yet other embodiments, the disease or disorder is insulin resistance. In yet other embodiments, the disease or disorder is Rett's syndrome. In yet other embodiments, the disease or disorder is metabolic syndrome associated with aging. In yet other embodiments, the disease or disorder is metabolic diseases associated with increased reactive oxygen species (ROS). In yet other embodiments, the disease or disorder is Friedreich's ataxia. In yet other embodiments, the disease is hepatic fibrosis. In yet other embodiments, the disease is liver cirrhosis. In yet other embodiments, the disease is hepatocellular carcinoma.

Sustained Release and Controlled Release Formulations

In one aspect, the invention provides a formulation for a sustained release of DNP. In certain embodiments, the invention provides sustained release formulations of DNP including a therapeutically effective amount of DNP or a pharmaceutically acceptable salt or solvate thereof. As used herein, "sustained release" or "extended release" refers to the fact that the DNP or pharmaceutically acceptable salt thereof is released from the formulation at a controlled rate so that therapeutically beneficial blood levels (which are below toxic levels) of the DNP or pharmaceutically acceptable salt thereof are maintained over an extended period of time. Alternatively, "sustained release" or "extended release" means that the desired pharmacologic effect is maintained over an extended period of time.

In one aspect, the invention provides the potential for enhanced patient convenience by reducing the frequency of dosing. In another aspect, the lower dosing frequency provides reduced side effects because the patient is exposed to lower peak concentrations of drug over time.

In certain embodiments, the invention provides an oral sustained release formulation. In yet other embodiments, the composition of the invention is formulated for oral sustained release. However, the invention should not be construed to be limited to only oral formulations, but rather encompass any form of formulations that provides a low dose and sustained release of DNP.

In certain embodiments, the sustained release formulations of the invention provide a controlled release of the drug over a longer period than observed for injectable or immediate release oral formulations (e.g., at least about 8-12 hours). In other embodiments, the sustained release is over a period of time that may be as long as a month or more and should be a release, which is longer that the same amount of agent administered in bolus form. In yet other embodiments, the period of time is greater than about one day, about two days, about one week, about two weeks, about one month, about two months, and any and all ranges there between. In yet other embodiments, the period of time is between about 12 and about 24 hours. In yet other embodiments, the period of time is about 12 hours. In yet other embodiments, the period of time is about 14 hours. In yet other embodiments, the period of time is about 24 hours.

In certain embodiments, the sustained release formulation is administered once a day. In other embodiments, the sustained release formulation is administered twice a day. In yet other embodiments, the sustained release formulation is administered three times a day.

In certain embodiments, the sustained release provides a steady state plasma concentration of a protonophore of the invention in a subject. In other embodiments, the steady state plasma concentration ranges between about 0.05 $\mu$M and about 200 $\mu$M. In yet other embodiments, the steady state plasma concentration ranges between about 0.05 $\mu$M and about 50 $\mu$M. In yet other embodiments, the steady state plasma concentration ranges between about 0.5 $\mu$M and about 50 $\mu$M. In yet other embodiments, the peak plasma concentration is equal to or lower than about 400 $\mu$M. In yet other embodiments, the peak plasma concentration is equal to or lower than about 300 $\mu$M. In yet other embodiments, the peak plasma concentration is equal to or lower than about 30 $\mu$M. In yet other embodiments, the steady state plasma concentration ranges between about 1 $\mu$M and about 10 $\mu$M. In yet other embodiments, the steady state plasma concentration ranges between about 1 $\mu$M and about 5 $\mu$M. In yet other embodiments, the steady state plasma concentration is about 5 $\mu$M. In yet other embodiments, the steady state plasma concentration is about 3 $\mu$M.

In certain embodiments, the sustained release formulation provides a tissue concentration of the compound of the invention in a subject. In other embodiments, the tissue concentration is equal to or lower than 10 $\mu$M. In yet other embodiments, the tissue concentration is equal to or lower than 5 $\mu$M. In yet other embodiments, the tissue concentration is equal to or lower than 2 $\mu$M.

The compound of the invention or a salt thereof may be homogeneously dispersed in the sustained release delivery system. In certain embodiments, the compound is present in the composition in an amount of about 1 mg to about 200 mg; about 1 mg to about 150 mg; about 1 mg to about 125 mg; or about 1 mg to about 100 mg. In certain embodiments, the compound or pharmaceutically acceptable salt thereof is present in the composition in an amount of about 2 mg to about 5 mg; about 5 mg to about 80 mg; about 10 mg to about 70 mg; about 15 mg to about 60 mg; about 40 mg to about 80 mg; about 50 mg to about 70 mg; or about 45 mg to about 60 mg. In certain embodiments, the compound or pharmaceutically acceptable salt thereof is present in the composition in an amount of about 2 mg; about 20 mg, about 40 mg, about 60 mg, about 75 mg, about 80 mg, about 100 mg, about 120 mg, about 140 mg, about 150 mg, about 160 mg, about 175 mg, about 180 mg or about 200 mg.

In certain embodiments, the ratio of the compound or pharmaceutically acceptable salt thereof to the sustained release delivery system in the composition is generally from about 4:1 to about 1:25. In some embodiments, the ratio of the compound or pharmaceutically acceptable salt thereof to the sustained release delivery system is generally from about 2.5:1 to about 1:4. In some embodiments, the ratio of the compound or pharmaceutically acceptable salt thereof to the sustained release delivery system is generally from about 5:1 to about 1:5, about 4:1 to about 1:4, about 3:1 to about 1:3, about 2:1 to about 1:2, about 1:1 to about 1:5, about 1:1 to about 1:4, about 1:1 to about 1:3, about 1:1 to about 1:2, and about 1:2 to about 1:3. In some embodiments, the ratio of the compound or pharmaceutically acceptable salt thereof to the sustained release delivery system is about 1:1, about 1:2, about 1:2.5, about 1:3, about 1:4, or about 1:5.

For sustained release, the compounds may be formulated with a suitable polymer or hydrophobic material that provides sustained release properties to the compound. As such, the compounds may be administered in the form of microparticles, for example, by injection or in the form of wafers or discs by implantation.

In certain embodiments, the compounds of the invention are administered to a patient, alone or in combination with another pharmaceutical agent, using a sustained release formulation.

In certain embodiments, the sustained release formulation of a compound of the invention is an orally administrable solid dosage formulation. Non-limiting examples of oral solid dosage formulations include tablets, capsules including a plurality of granules, sublingual tablets, powders, granules, syrups, and buccal dosage forms. In certain embodiments, tablets have an enteric coating or a hydrophilic coating.

In certain embodiments, the sustained release delivery system is prepared by dry granulation or wet granulation, before a compound of the invention or pharmaceutically acceptable salt thereof is added, although the components may be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules of the sustained release delivery system. Thereafter, the sustained release delivery system is mixed in the desired amounts with a compound of the invention or the pharmaceutically acceptable salt thereof and, optionally, one or more wetting agents, one or more lubricants, one or more buffering agents, one or more coloring agents, one or more second hydrophilic compounds, or other conventional ingredients, to produce a granulated composition. The sustained release delivery system and a compound of the invention may be blended with, for example, a high shear mixer. The compound of the invention is preferably finely and homogeneously dispersed in the sustained release delivery system. The granulated composition, in an amount sufficient to make a uniform batch of tablets, is subjected to tableting in a conventional production scale tableting machine at typical compression pressures, i.e., about 2,000-16,000 psi. In certain embodiments, the mixture should not be compressed to a point where there is subsequent difficulty with hydration upon exposure to liquids.

In some embodiments, a composition of the invention is prepared by dry granulation or wet granulation. The components of the sustained release delivery system are added, along with a compound of the invention or pharmaceutically acceptable salt thereof. Alternatively, all of the components may be held together by an agglomeration technique to produce an acceptable product. In the wet granulation technique, a compound of the invention or pharmaceutically salt thereof and the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules. Optionally, one or more wetting agents, one or more lubri-cants, one or more buffering agents, one or more coloring agents, one or more second hydrophilic compounds, or other conventional ingredients, are also added to the granulation. The granulated composition, in an amount sufficient to make a uniform batch of tablets, is subjected to tableting in a conventional production scale tableting machine at typical compression pressures, i.e., about 2,000-16,000 psi. In certain embodiments, the mixture should not be compressed to a point where there is subsequent difficulty with hydration upon exposure to liquids.

In certain embodiments, the average particle size of the granulated composition is from about 50 μm to about 400 μm. In certain embodiments, the average particle size is from about 185 μm to about 265 μm. The average density of the granulated composition is from about 0.3 g/mL to about 0.8 g/mL. In certain embodiments, the average density is from about 0.5 g/mL to about 0.7 g/mL. The tablets formed from the granulations are generally from about 4 Kp to about 22 kP hardness. The average flow of the granulations is from about 25 to about 40 g/sec.

In one aspect, the invention provides a multilayer solid dosage form, in which the layers are formulated to release a compound of the invention at different rates. For example, In certain embodiments, the second layer is an extended release layer that includes a compound of the invention or a pharmaceutically acceptable salt thereof and a sustained release delivery system designed to release a compound of the invention or the pharmaceutically acceptable salt thereof at a controlled rate so that therapeutically beneficial blood levels are maintained over an extended period of time (e.g., from about 8 to about 12 hours). The first layer is an immediate release layer that includes a formulation of a compound of the invention or a pharmaceutically acceptable salt thereof designed to release the compound of the invention or the pharmaceutically acceptable salt thereof at a rate that is faster than the rate of the second layer to achieve a therapeutically beneficial blood level in an immediate period of time (e.g., from about 1 to about 2 hours). In some embodiments, the first layer includes a sustained release delivery system. In some embodiments, the first layer does not include a sustained release delivery system.

In some embodiments, the weight ratio of the second layer to the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In certain embodiments, the weight ratio of the second layer to the first layer is about 5:1 to about 1:5. In yet other embodiments, the weight ratio of the second layer to the first layer is about 1:1 to about 1:2. In yet another embodiments, the weight ratio of the second layer to the first layer is about 1:1, about 1:1.2, about 1:1.4, about 1:1.6, about 1:1.8, or about 1:2. In certain embodiments, the weight ratio of the second layer to the first layer is about 1:2. In certain embodiments, the weight ratio of the second layer to the first layer is about 1:1.4. In some embodiments, the weight ratio of the second layer to the first layer is about 3:1, about 2.5:1, about 2:1, about 1.5:1. In certain embodiments, the weight ratio of the second layer to the first layer is about 2.5:1.

In some embodiments, the multilayer dosage form further includes a pharmaceutical disintegrant. The disintegrant promotes the dissolution and absorption of a compound of the invention or pharmaceutically acceptable salt thereof from the immediate release layer. Non-limiting examples of pharmaceutical disintegrants include croscarmellose sodium, starch glycolate, crospovidone, and unmodified starch. In certain embodiments, the disintegrant is in the first layer (i.e., the immediate release layer), of the dosage form. In certain embodiments, the disintegrant is present in the layer in an amount of about 1.5 mg to about 4.5 mg. In certain embodiments, the disintegrant is present in the layer in an amount of about 2-10% by weight. In certain embodiments, the disintegrant is present in the layer in an amount of about 5% by weight. When the layer contains a sustained release delivery system, the weight ratio of the sustained release delivery system to the disintegrant is in a range of about 5:1 to about 1:5. In some embodiments, the ratio of the sustained release delivery system to the disintegrant is in a range of about 1:1 to about 3:1. In other embodiments, the ratio of the sustained release delivery system to the disintegrant is in a range of about 2:1.

In some embodiments, the multilayer tablets of the invention are prepared by first preparing the immediate release layer and extended release layer blends separately. The extended release layer is prepared as described elsewhere herein. The wet granulation of the extended release layer is then dried and milled to an appropriate size. Magnesium stearate is added and mixed with the milled granulation. The immediate release layer of the invention is prepared by first mixing a compound of the invention or the pharmaceutically acceptable salt thereof with one or more diluents (e.g., microcrystalline cellulose). This mix is then optionally mixed with one or more disintegrants. The blend is mixed with magnesium stearate. Finally, the immediate release layer blend and the extended release layer blend are compressed into multi-layer (e.g., bi-layer) tablets.

In certain embodiments, the formulations of the present invention may be, but are not limited to, short-term, rapid-offset, as well as controlled, for example, delayed release and pulsatile release formulations.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Methods

The invention includes a method of preventing or treating a disease or disorder in a subject in need thereof. The method comprises administering to the subject a therapeutically effective amount of a pharmaceutical composition comprising a compound selected from the group consisting of 2,4-dinitrophenol (DNP), a salt thereof, a solvate thereof, and any combinations thereof, wherein the composition provides a sustained release of the compound in the subject, whereby the disease or disorder in the subject is treated or prevented in the subject.

The invention further includes a method of increasing energy expenditure in a subject in need thereof. The method comprises administering to the subject a therapeutically effective amount of a pharmaceutical composition comprising a compound selected from the group consisting of DNP, a salt thereof, a solvate thereof, and any combinations thereof, wherein the composition provides a sustained release of the compound in the subject, whereby energy expenditure in the subject is increased.

In certain embodiments, the disease or disorder is at least one selected from the group consisting of non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma.

In certain embodiments, the subject is afflicted with at least one disease or disorder selected from the group consisting of non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma.

In certain embodiments, the therapeutically effective dose of the compound ranges from about 1 mg/kg/day to about 10 mg/kg/day. In other embodiments, administration of the composition affords a steady state plasma concentration of the compound ranging from about 0.05 µM to about 200 µM in the subject. In yet other embodiments, administration of the composition affords a steady state plasma concentration of the compound ranging from about 0.5 µM to about 50 µM in the subject. In yet other embodiments, administration of the composition affords a steady state plasma concentration of the compound ranging from about 1 µM to about 10 µM in the subject. In yet other embodiments, administration of the composition affords a steady state plasma concentration of the compound in the subject ranging from about 3 µM to about 5 µM in the subject.

In certain embodiments, the steady state plasma concentration of the compound in the subject is about 50 to about 100 times lower than the toxic concentration of the compound in the subject.

In certain embodiments, administration of the composition affords therapeutically effective levels of the compound in the subject for a period of time ranging from about 12 hours to about 24 hours. In certain embodiments, the composition is administered once, twice or three times a day to the subject.

In certain embodiments, administration of the composition does not cause significant systemic toxicity or significant increase in body temperature in the subject. In other embodiments, the significant systemic toxicity is indicated by increase in levels of liver enzymes, blood urea nitrogen or creatinine as compared to the corresponding levels in the subject in the absence of administration of the composition. In yet other embodiments, the composition is formulated for oral administration.

In certain embodiments, the method further comprises administering to the subject at least one additional therapeutic agent. In other embodiments, the composition and the at least one additional therapeutic agent are co-administered to the subject. In yet other embodiments, the composition and the at least one additional therapeutic agent are co-formulated.

In certain embodiments, the subject is a mammal. In other embodiments, the mammal is human.

Combination Therapies

The compounds useful within the methods of the invention may be used in combination with one or more additional compounds useful for treating a disease or disorder. These additional compounds may comprise compounds that are commercially available or synthetically accessible to those skilled in the art. These additional compounds are known to treat, prevent, or reduce the symptoms of a disease or disorder.

In non-limiting examples, the compounds useful within the invention may be used in combination with one or more of the following therapeutics:

Pulmonary Hypertension Drugs: ambrisentan, bosentan, treprostinil, sildenafil, epoprostenol, treprostenol, iloprost, aldosterone receptor antagonists like spironolactone and eplerenone, angiotensin-converting enzyme inhibitors such as trandolapril, fosinopril, enalapril, captopril, ramipril, moexipril, lisinopril, quinapril, benazepril, and perindopril;

Angiotensin II Inhibitors: eprosartan, olmesmian, telmismian, losartan, valsmian, candesartan, and irbesmian, anti-anginal agents like nitroglycerin, isosorbide mononitrate, and isosorbide dinitrate, anti-arrhythmic agents including moricizine, quinidine, disopyramide, phenyloin, propafenone, flecamide, mexilitene, lidocaine, procainamide, propranolol, acebutolol, amiodarone, dofetilide, dronedarone, sotalol, ibutilide, diltiazem, verapamil, nifedipine, nimodipine, felodipine, nicardipine, clevidipine, isradipine, bepridil, nisoldipine, adenosine, and digoxin;

β-adrenergic Receptor Antagonists: betaxolol, bisoprolol, metoprolol, atenolol, nebivolol, nadolol, carvedilol, labetalol, timolol, carteolol, penbutolol, pindolol, and esmolol;

Anti-Diabetic Agents: insulin, GLP-1 agonists, DPP4 inhibitors, SGLT-2 inhibitors, secretagogues such as sulfonylurea, tolbutamide, acetohexamide, tolazamide, chlorpropamide, glipizide, glyburide, glimepiride, glibenclamide, gliclazide, meglitinide such as nateglinide, senaglinide, repaglinide, insulin sensitizers such as biguanides, metformin, thiazolidinediones such as rosiglitazone, isaglitazone, darglitazone, englitazone, and pioglitazone;

α-Glucosidase Inhibitors: miglitol, voglibose, emiglitate, and acarbose;

Glucagon-Like Peptide Analogs and Agonists: exenatide, liraglutide, and taspglutide, dipeptidyl peptidase-4 inhibitors like vildagliptin, sitagliptin, and saxagliptin;

Amylin Analogs: pramlintide;

Ligands or Agonists of Peroxisome Proliferator Activated Receptor (PPAR)-α, β, δ, and γ Cholesterol-Lowering Agents: hydroxymethylglutaryl-Coenzyme A (HMG-CoA) reductase inhibitors like statins, such as, e.g., atorvastatin, fluvastatin, lovastatin, pitavastatin, pravastatin, rosuvastatin, and simvastatin;

Agonists of Retinoid X Receptors (RXR): ALRT-268, LG-1268, or LG-1069; glucokinase activators, inhibitors of hepatic enzymes involved in stimulation of gluconeogenesis and/or glycogenolysis, Diuretics: acetazolamide, dichlorphenamide, methazolamide, torsemide, furosemide, bumetanide, ethacrynic acid, amiloride, triamterene, indapamide, metolazone, methylclothiazide, hydrochlorothiazide, chlorothiazide, metolazone, bendroflumethiazide, polythiazide, and chlorthalidone;

Vasodilators: alprostadil, hydralazine, minoxidil, nesiritide, and nitropruside;

Anti-Lipidemic Agents: cholestyramine, colestipol, clofibrate, gemfibrozil, probucol or dextrothyroxine;

Adipocytokines: leptin, adiponectin, and metreleptin;

Drugs for the treatment of Hyperlipidemia: fibrates, omega fatty acids, fish oil, statins.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective dose of a composition of the invention. The therapeutic dose of a composition of the invention may be administered to the subject either prior to or after the onset of a disease or disorder. Further, several divided dosages, as well as staggered dosages may be administered daily or sequentially, or the dose may be continuously infused, or may be a bolus injection. Further, dosing of a composition of the invention may be proportionally increased or decreased as indicated by the exigencies of the therapeutic or prophylactic situation.

Administration of a composition of the invention to a patient, preferably a mammal, more preferably a human, may be carried out using known procedures, at dosages and for periods of time effective to treat a disease or disorder in the patient. An effective amount of a composition of the invention necessary to achieve a therapeutic effect may vary according to factors such as the state of the disease or disorder in the patient; the age, sex, and weight of the patient; and the ability of the therapeutic formulation to treat a disease or disorder in the patient. Dosing of a composition of the invention may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of a composition of the invention without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of a composition of the invention. For example, the physician or veterinarian could start doses of a composition of the invention employed in the pharmaceutical composition at levels lower than that required in order to achieve the desired therapeutic effect and gradually increase the dosage until the desired effect is achieved.

In particular embodiments, it is especially advantageous to formulate a composition of the invention in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, a composition of the invention is formulated using one or more pharmaceutically acceptable excipients or carriers. In certain embodiments, the formulations of the invention comprise a composition of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, a composition of the invention is administered to the patient in dosages that range from one to five times per day or more. In yet other embodiments, the formulations of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

In certain embodiments, the present invention is directed to a packaged pharmaceutical formulation comprising a container holding a therapeutically effective amount of a formulation of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, a composition of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, a composition of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Dosing

The dosing of a composition of the invention depends on the age, sex and weight of the patient, the current medical condition of the patient and the progression of a disease or disorder in the patient being treated. The skilled artisan is able to determine appropriate dosages depending on these and other factors.

A suitable dose of a compound of the present invention may be in the range of from about 0.001 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, dosing of a composition of the invention may be initiated on Monday with a first subsequent low dose administered on Wednesday, a second subsequent low dose per day administered on Friday, and so on. In certain embodiments, the compound is dosed at least once a day. In yet other embodiments, the compound is dosed at least twice a day.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance low dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Animals:

Sprague-Dawley rats (300-400 g) and Zucker Diabetic Fatty rats (250 g) were ordered from Charles River Laboratories and allowed to acclimate for at least one week before use. If not otherwise specified, rats were fed regular chow. In the NAFLD reversal model, rats were fed a safflower oil based high fat diet (60% calories from fat) (Harlan) for the time periods specified, and were given free access to water at all times.

To determine whether ERDNP prevents NAFLD, rats were fed safflower oil high fat diet for two weeks while treated daily with ERDNP (1 mg/kg) or vehicle. To induce NASH, rats were fed methionine/choline deficient diet (Harlan) for eight weeks, then continued on this diet while treated them with 1 mg/kg ERDNP or vehicle.

Surgery was performed under isoflurane anesthesia to place polyethylene catheters (Instech Solomon) in the common carotid artery, jugular vein, and, where specified, antrum of the stomach (PE50, PE90, and PE90 tubing, respectively). Rats were fasted for 6 hrs for measurement of DAG concentrations, and overnight (16 hours) for all other studies. For terminal studies, rats were euthanized by intravenous pentobarbital.

For the intragastric DNP infusion studies, rats previously fed high fat diet for 2 weeks were placed in a Covance infusion harness attached to a single-axis counter-balanced swivel mount and a stainless steel one-channel swivel (all from Instech Solomon) to protect the catheters and allow the animals free access to the cage. DNP (2 mg/kg per day) or vehicle (10% dimethylsulfoxide/90% saline vehicle) was infused continuously through the arterial line for 5 days.

ERDNP was formulated by Emerson Resources Inc. (Malvem, Pa.) with sustained-release ethylcellulose coating. Rats used for the NAFLD reversal studies were fed high fat diet for 2 weeks, at the end of which they were treated for three days with peanut butter to acclimate them to this food. They were then treated daily with ERDNP mixed in peanut butter, or peanut butter vehicle, at the doses specified in the text daily for 5 days. Zucker Diabetic Fatty rats were treated with ERDNP (1 mg/kg) in peanut butter or peanut butter vehicle daily for 14 days. Blood glucose was measured by glucometer (Abbott) from the tail vein every three days.

Rats used for the NASH reversal studies were fed methionine/choline deficient diet for eight weeks as described above, then treated with 1 mg/kg ERDNP or vehicle daily for six weeks while continuing on methionine/choline deficient diet.

Normal male C57BL/6J mice were ordered at 12 weeks of age from Jackson and were fed regular chow. After acclimating for five days, they underwent metabolic cage (CLAMS) analysis. The reported food intake does not include caloric intake from the small amount of peanut butter (~250 mg) used to administer ERDNP or vehicle; however, the peanut butter quantity was matched between groups.

Toxicity Studies:

Alanine aminotransferase, aspartate aminotransferase, and blood urea nitrogen were measured using the COBAS Mira Plus, and creatinine by LC/MS/MS. Body temperature was measured using a rectal probe (Physitemp Instruments). Histology slides were stained with hematoxylin & eosin, Sirius Red, and TUNEL stains.

Studies of Basal Metabolism:

Plasma insulin and glucagon were measured by radioimmunoassay. Plasma glucose was measured enzymatically by the YSI Life Sciences 2700 Select Biochemistry Analyzer. Plasma concentrations of twelve inflammatory markers, adiponectin, and FGF-21 were assessed by ELISA (QIAGEN, Life Technologies, and Millipore, respectively). Liver glycogen was measured by amyloglucosidase digestion (Passonneau & Lauderdale, 1974, Anal. Biochem. 60:405-12). Non-esterified fatty acid concentrations were measured by an enzymatic kit (Wako).

To measure total glutamate enrichment from livers of rats infused with [3-$^{13}$C] lactate, ~100 mg frozen liver were homogenized in 400 µL ice-cold 50% acetonitrile. The samples were centrifuged at 10,000 g for 10 min, and the supernatant was isolated. After overnight storage at 4° C., the samples were centrifuged at 10,000 g for 10 min through a Nanosep 100 k Omega filter (Pall Life Sciences). The flow-through was separated on a hypercarb column (Thermo Scientific; 4.6×100 mm; 5 µm particle size) before ionization for multiple reaction monitoring analysis by LC/MS/MS (Applied Biosystems MDS SCIEX, 4000 Q-TRAP).

To measure positional glutamate and alanine enrichment, the liver samples were extracted for nuclear magnetic resonance (NMR) spectroscopy. ~4-6 g ground liver were centrifuged in ~30 mL 7% perchloric acid. The pH of the supernatant was adjusted to 6.5-7.5 using 30% potassium hydroxide and 7% perchloric acid as needed, and the extract was dehydrated by lyophilizing for 2-3 days. The extract was resuspended in 500 µL potassium phosphate buffer: 2.4 mM NaCOOH, 30 mM $K_2HPO_4$, 10 mM $KH_2PO_4$, 20 mM DMSO (internal standard) in 100% $D_2O$. $^{13}C$ NMR spectra were collected using the AVANCE 500-MHz NMR spectrometer (Bruker Instruments).

Spectra were acquired with relaxation time=1 s, dummy scans=32, and number of scans=8,192 per block×3 blocks. Correction factors for differences in $T_1$ relaxation times were determined from fully relaxed spectra of natural abundance glutamate and glucose solutions. The total glutamate enrichment by LC/MS/MS was divided algebraically according to the peak areas of [$^{13}$C] glutamate for each carbon corrected for T1 relaxation times.

Total glucose enrichment in the NMR extract was determined by derivatizing 20 µL of the NMR extract with 100 µL methanol, then drying overnight in a Speed-Vac. The extract was then resuspended in 75 µL 1:1 acetic anhydride: pyridine and heated for 20 min at 65° C. The sample was cooled and quenched with 25 µL methanol. The total m+1 glucose enrichment of each sample was measured by gas chromatography/mass spectrometry using previously described methods (Shulman et al., 1985, J. Clin. Invest. 76:757-764). m+2, m+3, m+4, m+5, and m+6 enrichment were found to be negligible (<5% of m+1 enrichment at steady-state). $^{13}C$ NMR spectra were used to determine relative concentrations of [$^{13}$C] glucose. As for glutamate, the total glucose enrichment by mass spectrometry was divided algebraically to measure the enrichment at each glucose carbon.

To measure positional alanine enrichment from [3-$^{13}$C] lactate infused rat livers, liver samples were extracted for NMR as described above, and the enrichment at [2-$^{13}$C] and [3-$^{13}$C] alanine was measured by proton-observed, carbon-edited NMR as we have reported (Alves et al., 2011, Hepatology 53:1175-1181).

Lipid Measurements:

Plasma triglycerides were measured using a Wako reagent. Liver and quadriceps triacylglycerol were extracted using the method of Bligh and Dyer (Bligh & Dyer, 1959, Can. J. Biochem. Physiol. 37:911-7) and quantified spectrophotometrically using a reagent from Diagnostic Chemicals Ltd. Liver and quadriceps DAG and ceramide concentrations were measured by liquid chromatography/mass spectrometry/mass spectrometry (LC/MS/MS) (Yu, et al., 2002, J. Biol. Chem. 277:50230-6), as were acylcarnitine concentrations (An, et al., 2004, Nat. Med. 10:268-74). Very low-density lipoprotein (VLDL) export was measured (Lee, et al., 2011, Hepatology 54:1650-60). Liver acetyl and malonyl CoA concentrations were measured by LC/MS/MS (Hosokawa, et al., 1986, Anal. Biochem. 153:45-9; Roughan, 1994, Biochem. J. 300:355-8).

Markers of Liver Fibrosis and Apoptosis:

Caspase-3 and -9, smooth muscle actin, and inflammatory cytokines were measured in liver homogenates by ELISA (MyBioSource, NeoBioLab, MyBioSource, and SABiosciences, respectively), and were normalized to total protein content measured by Bradford assay. Liver hydroxyproline content was measured (Cai, et al., 2014, J. Pharmacol. Exp. Therap. 349:94-98). Collagen mRNA was measured in liver, and UCP1 mRNA in BAT by qPCR (Kumashiro, et al., 2011, Proc. Natl. Acad. Sci. USA 108:16381-16385).

Glucose Tolerance Tests:

Rats were given an intraperitoneal bolus of 50% dextrose (1 mg/kg) at time zero. Plasma was obtained by drawing blood through the venous catheter at times 0, 5, 10, 20, 30, 45, 60, and 90 min and centrifuged immediately. Plasma glucose and insulin concentrations were measured as described elsewhere herein.

Measurement of Insulin Sensitivity and Hepatic Fluxes:

Basal and insulin-stimulated glucose turnover were measured using a steady-state (120 min) infusion of [6,6]$^2H_2$ glucose (Erion, et al., 2013, Endocrinology 154:36-44).

Muscle and BAT glucose uptake were measured by injection of [$^{14}$C]2-deoxyglucose into the venous line (Samuel, et al., 2007, J. Clin. Invest. 117:739-45).

PKCε and θ translocation in liver and quadriceps, respectively, were measured by Western blot (Choi, et al., 2007, Proc. Natl. Acad. Sci. USA 104:16480-5).

Liver PC flux ($V_{pc}$), flux through the TCA cycle ($V_{tca}$), and substrate contributions to the TCA cycle ($V_{pdh}$, $V_{fa}$) were measured by steady-state [3-$^{13}$C] lactate infusion (Perry, et al., 2013, Cell. Metab. 18:740-8).

Measurement of Gluconeogenic Protein Concentrations:

Protein concentrations of pyruvate carboxylase, glucose-6-phosphatase, and fructose-1,6-bisphosphatase were measured using antibodies from Santa Cruz Biotechnology (Kumashiro, et al., 2013, Diabetes 62:2183-94). CD69 was measured using an antibody from Novus Biologicals (Kumashiro, etb al., 2013, Diabetes 62:2183-2194). PKC translocation was measured (Samuel, et al., 2007, J. Clin. Inv. 117:739-745).

DNP and ERDNP Kinetics Studies:

Rats consumed the concentrations of DNP or ERDNP specified in the text orally, mixed in peanut butter. All rats used for the kinetics studies consumed the entirety of the peanut butter and protonophore within 2 minutes.

Figure 21A:
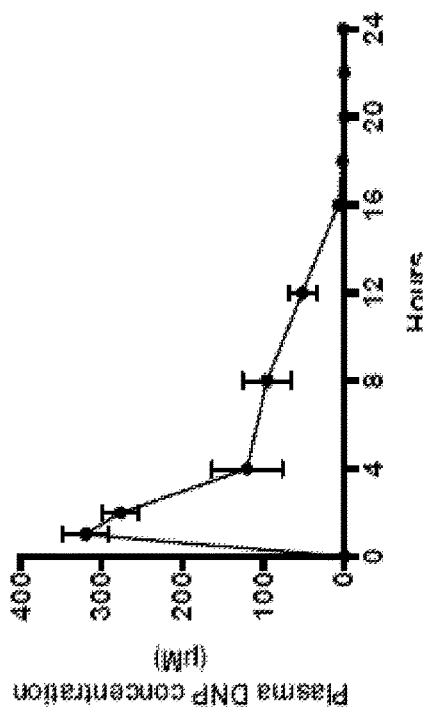
FIGS. 21A-21B: Plasma DNP concentrations after 1 mg/kg (FIG. 21A) or 25 mg/kg (FIG. 21B) DNP at time 0. n=3-4.
Figure 21B:
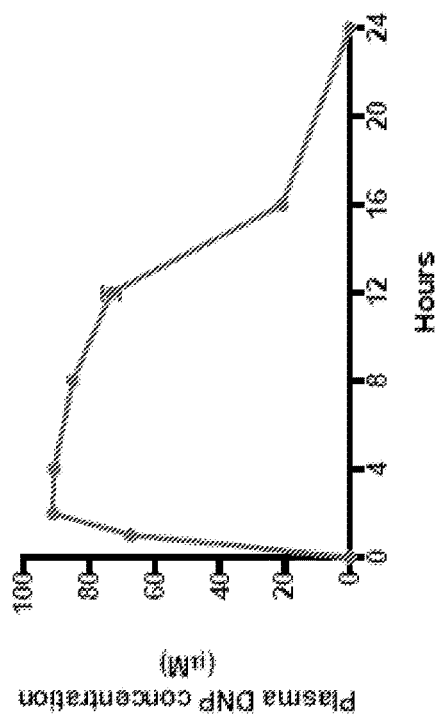
Figure 21C:
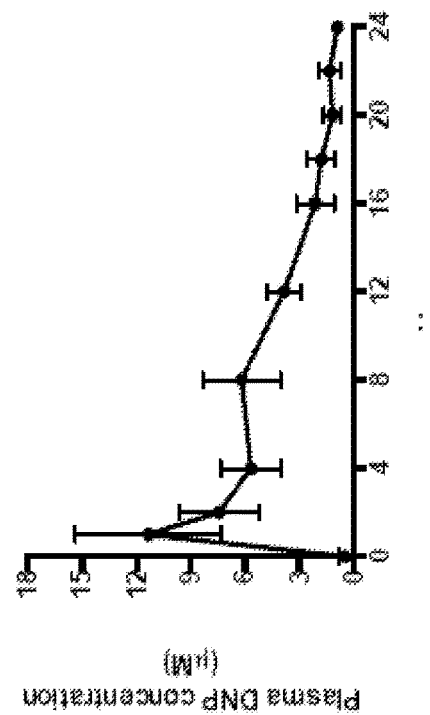
FIGS. 21C-21D: Plasma DNP concentrations after 1 mg/kg (FIG. 21C) or 25 mg/kg (FIG. 21D) ERDNP at time 0. n=6-9.
Figure 21D:
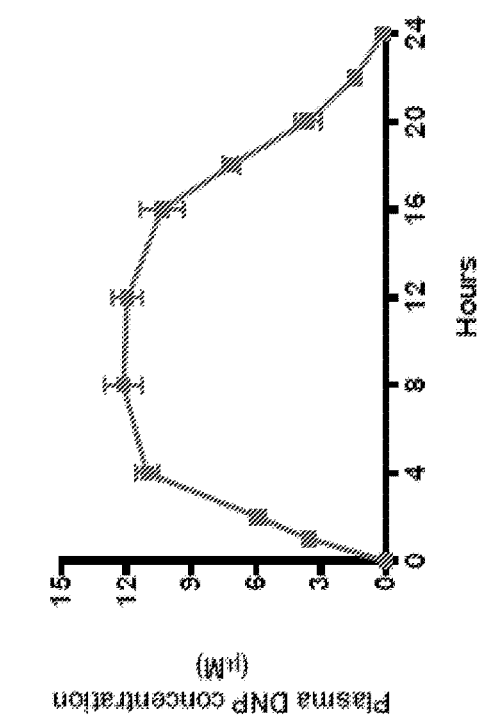

DNP concentrations were measured in plasma, liver, kidney, WAT, quadriceps, heart, and brain of Sprague-Dawley rats by LC/MS/MS (Perry, et al., 2013, Cell. Metab. 18:740-8). Rats treated with DNP were sacrificed 1 hour after treatment with DNP, and those treated with ERDNP were sacrificed 8 hours after treatment, as these were the times determined in the plasma DNP studies to represent the peak plasma DNP concentrations (FIGS. 21A-21B). The minimal detection limit of the method was determined to be 0.05 µM, as this was the minimum concentration of solutions of known quantities of DNP in DMSO measured by the method with less than 20% error in each of three replicates.

Statistical Analysis:

Differences were assessed by the 2-tailed unpaired Student's t-test when two groups were compared, or by ANOVA with Bonferroni's multiple comparisons test when three groups were compared. P-values <0.05 were considered significant. Data are reported as mean±S.E.M.

Histology Studies:

Liver and kidney samples were prepared and stained with hematoxylin & eosin by the Yale Research Histology core, and analyzed as described (Kleiner et al., 2005, Hepatology 41:1313-1321).

Measurement of Liver Glycogen Content:

Hepatic glycogen content was assessed by amyloglucosidase digestion using previously described methods (Passonneau and Lauderdale, 1974, Anal. Biochem. 60:405-412).

Assessment of Potential Gluconeogenic Markers:

Plasma concentrations of twelve inflammatory markers were measured by ELISA (QIAGEN, Valencia, Calif.). Adiponectin was measured by ELISA by the Yale Diabetes Research Center Physiology Core. Lactate was measured by COBAS, and FGF-21 by ELISA (Millipore).

Measurement of Plasma and Tissue DNP Concentrations:

LC/MS/MS method development and analysis were performed on the Applied Biosystems 4000 QTRAP (Foster City, Calif.), equipped with a Shimadzu ultra fast liquid chromatography (UFLC) system. Electrospray ionization (ESI) source with negative-ion detection was shown as the most sensitive for both qualitative and quantitative analysis of DNP. The quantitative analysis of DNP was monitored in MRM mode with an ion pair (183.0/109.0). The preferred parameters are: curtain gas 25; collision gas 9, probe temperature 480° C.; ion source gas 1 20; ion source gas 2 25; declustering potential (DP) −45 V; entrance potential (EP) −10 V; collision energy (CE) −35 V and collision cell exit potential −12 V.

Extraction from Plasma Samples for LC/MS/MS Analysis:

Plasma samples (10-100 µL) were mixed with 2.0 ml pre-chilled chloroform/methanol (v/v: 2/1) containing 0.01% BHT in 5 ml glass vials, to which was added 250 µl water together with 10 nmol DNP-$D_3$ and 10 nmol DNPME-$D_6$ as the internal standards. The mixtures were vortexed for 10 seconds before centrifugation at 4000 rpm for 10 min. The bottom organic layer was carefully collected and dried with a steady stream of nitrogen gas. The residual was reconstituted in 200 µl methanol for LC/MS/MS analysis for DNP and/or DNPME metabolites.

Extraction from Various Tissue Samples for LC/MS/MS Analysis:

Frozen tissue samples (~100 mg) were weighed and suspended in 2 ml microcentrifuge tubes with 1.6 ml pre-chilled chloroform/methanol (v/v: 2/1) containing 0.01% BHT and one metal bead, and then added 10 nmol DNP-d3 (Cambridge Isotopes, Andover, Mass.) as the internal standards. The tissue samples were disrupted with Qiagen TissueLyser at 30 Hz for 15 min, and then transferred into 5 ml glass vials, followed by addition of 0.5 ml chloroform and 250 µl water into each samples. The samples were centrifuged at 4000 rpm for 10 min after vortexed for 10 seconds. The bottom organic layer was collected and dried with a gentle flow of nitrogen. The residual was reconstituted in 200 µl methanol for LC/MS/MS analysis of DNP.

Example 1

Formulation of DNP

DNP was formulated for extended release. In certain embodiments, extended release of DNP reduces toxicity and maximizes efficacy. In other embodiments, the DNP formulation comprise a DNP extruded or drug layered bead that is coated with a sustained release coating in a dosage size suitable to deliver 1.0 mg/kg of DNP over a 12-24 hour period.

In certain embodiments, the polymers used in the sustained release coating work independent of pH, as they are a combination of soluble and insoluble polymers, allowing release through pores created by the soluble polymer. In other embodiments, the formulated drug is absorbed in the acidic stomach and/or neutral intestine. In yet other embodiments, a multiparticulate system allows for lower variance in dissolution rates (as a coating failure in a tablet could result in complete release of the dose whereas a coating failure in one of many particulates would result in a minimally altered dissolution profile).

In certain embodiments, a DNP bead is prepared using extrusion and spheronization. In order to achieve controlled release, two polymer systems were selected for evaluation: a EUDRAGIT® RS/RL system and a hydroxypropylcellulose (HPC)/ethylcellulose (EC) system. Initial formulation work focused on evaluating the HPC/EC and EUDRAGIT® systems at various coating levels, and the HPC/EC system was selected for further investigation. Table 1 illustrates raw materials used for preparation of ERDNP spheres.

TABLE 1

| Generic Name | Trade Name | Supplier |
| --- | --- | --- |
| Mannitol | MANNITOL 100 SD | Roquette |
| Microcrystalline cellulose (MCC) | MCC PH-101 | FMC Biopolymer |
| Hydroxypropylmethyl cellulose (HPMC) | PHARMACOAT® 606 | Shin-Etsu |
| Ethylcellulose (EC) | ECN 10 | Dow |
| Hydroxypropylcellulose (HPC) | KLUCEL® EF | Ashland |
| GMS Emulsion | PLASACRYL® T20 | Emerson |
| Polysorbate 80 | — | Evonik |
| Talc | — | Brenntag |
| Dibutyl sebacate (DBS) | — | Vertellus |
| Distilled water | — | Emerson |
| Ethanol (200 proof) | — | Spectrum |

Uncoated 2,4-DNP Extruded Sphere

In certain embodiments, a desired dose weight is selected based on three factors: development of a dosage weight that would feasibly deliver the requested dose (1.0-1.5 mg/kg) to subjects, avoidance of uniformity issues, and avoidance of issues with the sustained release coating. Based on the selected dose weight and API concentration, a formulation using common excipients for extruded beads was developed. The initial bead formulation (NK15-142, CU03-170, CU03-171) was designed to deliver 1.5 mg DNP/60 mg beads; however, this did not take into account a 22% moisture content in the active pharmaceutical ingredient (API), which resulted in an actual API concentration closer to 1.17 mg/60 mg beads. Subsequent batches were formulated similarly to the latter but were adjusted to deliver 1.0 mg DNP/50 mg beads (or 1.17 mg/58.5 mg beads). Table 3 illustrates the composition of the initial uncoated bead formulations.

TABLE 2

| | NK15-142, CU03-170, CU03-171 | | | | | NK15-155 | | | | |
|---|---|---|---|---|---|---|---|---|---|---|
| Ingredient | % w/w (wet) | g wet/ batch | % w/w (dry) | g dry/ batch | mg/ dose | % w/w (wet) | g wet/ batch | % w/w (dry) | g dry/ batch | mg/ dose |
| Mannitol | 65.3 | 391.8 | 65.7 | 391.8 | 39.4 | 65.4 | 394.8 | 65.8 | 394.8 | 32.9 |
| MCC | 32.0 | 192.0 | 32.2 | 192.0 | 19.3 | 31.8 | 192.0 | 32.0 | 192.0 | 16.0 |
| HPMC | 0.2 | 1.2 | 0.2 | 1.2 | 12.1 | 0.2 | 1.2 | 0.2 | 1.2 | 0.1 |
| 2,4-DNP[1] | 2.5 | 15.0 | 2.0 | 11.7 | 1.2 | 2.5 | 15.4 | 2.0 | 12.0 | 1.0 |
| Water | — | 200.0[2] | — | — | — | — | 200.0 | — | — | — |
| Total | 100.0 | 600.0 | 100.0 | 596.7 | 60.0 | 100.0 | 603.4 | 100.0 | 600.0 | 50.0 |

[1] 2,4-DNP contains 22% moisture. The % w/w wet shows the weight percent of wet API dispensed for the batch. The dry basis % w/w and mg/dose takes into account only the solids concentration, omitting the 22% moisture in the API.
[2] Water is used as a processing aid and does not appear in the final product. It is not represented in the % w/w or final batch weight and is only included to show the quantity added for processing.

To prepare the uncoated spheres, the solid components were added to a high shear mixer and mixed until visually uniform (1 minute at mix speed 300 rpm). 200 ml water were added, and the solution was mixed until visually uniform (2-3 minutes at mix speed 300 rpm). The material was discharged and extruded with a 0.7 mm die face, 9 shims, at 90 rpm. The extrudate was divided into two batches, and each was spheronized with a 2 mm plate at 980 rpm for 2 minutes. The beads were then placed in an oven and dried until the final moisture content was <7.5% based on starting weight.

Controlled Release Bead Formulation Development

In order to achieve controlled (12-24 hr) release, two polymer systems were selected for evaluation: an EUDRAGIT® RS/RL system and a hydroxypropylcellulose (HPC)/ethylcellulose (EC) system.

The EUDRAGIT® system functions by combining permeable and impermeable pH independent swelling polymers, allowing the drug to diffuse out over time, controlled by both the ratio of permeable and impermeable polymer and the amount of polymer applied.

The HPC/EC system functions by combining soluble and insoluble polymers to create pores in the coating through which the drug diffuses over time, also controlled by the ratio of the polymers and the amount of polymer applied. Formulations for the two coating suspensions are described in Table 3.

To generate the controlled-release coating with the EUDRAGIT® system, the Plasacryl was shaken and mixed. While mixing, the EUDRAGIT®, water, TEC, and PS80 were added. The suspension was then passed through a 30 mesh screen and mixing was continued. To coat the DNP spheres produced as described elsewhere herein, the FLM1 fluid bed was set up with bottom spray Wurster coating with a 1.2 mm liquid nozzle, 3 mm air cap, Wurster column, 400 mesh inlet screen, conidor plate, and 40 mesh filters. The spheres were loaded into the fluid bed and coated using the parameters in Table 4. The beads were then dried for a minimum of 10 min with an inlet temperature of 40° C.

TABLE 4

| Parameter | Target range |
|---|---|
| Spray rate | 15-25 g/min |
| Inlet temperature | 44-47° C. |
| Product temperature | 34-37° C. |
| Nozzle air | 40 psi |
| Process air | 55-70 cfm |

Two lots of beads coated with the HPC/EC system were coated and sampled at three theoretical weight gains (11.7%, 13.3%, and 15% for Lot NK15-144 and 7.5%, 10%, and 11.7% for Lot NK15-157). The final coated bead formulation for each lot (based on a 1 mg dose and the maximum coating applied) is illustrated in Table 5.

TABLE 3

| | NK15-146 (Eudragit System) | | | | NK15-143 (HPC/EC System) | | | |
|---|---|---|---|---|---|---|---|---|
| Ingredient | % w/w | % solids | g solids/ batch | g/batch | % w/w | % solids | g solids/ batch | g/batch |
| EUDRAGIT® RS 30D | 42.0 | 30.0 | 168.0 | 560.0 | — | — | — | — |
| EUDRAGIT® RL 30D | 10.5 | 30.0 | 42.0 | 140.0 | — | — | — | — |
| ECN 10 | — | — | — | — | 6.92 | 100.0 | 103.8 | 103.8 |
| KLUCEL® EF | — | — | — | — | 0.77 | 100.0 | 11.5 | 11.5 |
| PLASACRYL® T20 | 7.8 | 20.0 | 20.8 | 104.0 | — | — | — | — |
| TEC | 2.4 | 100.0 | 32.0 | 32.0 | — | — | — | — |
| Polysorbate 80 | 0.9 | 33.0 | 4.0 | 12.0 | — | — | — | — |
| Talc | — | — | — | — | 1.54 | 100.0 | 23.1 | 23.1 |
| DBS | — | — | — | — | 0.77 | 100.0 | 11.5 | 11.5 |
| DI Water | 36.4 | 0.0 | 0.0 | 485.3 | 9.00 | 0.0 | 0.0 | 135.0 |
| Ethanol | — | — | — | — | 81.00 | 0.0 | 0.0 | 1215.0 |
| Total | 100.0 | 20.0 | 266.8 | 1333.3 | 100.00 | 10.0% | 100.0 | 1500.0 |

TABLE 5

| | Lot # | | | |
|---|---|---|---|---|
| | NK 15-144 (15.0% weight gain) | | NK 15-157 (11.7% weight gain) | |
| Ingredient | % w/w | mg/dose | % w/w | mg/dose |
| 2,4-DNP drug spheres | 87.0 | 51.3 | 89.5 | 50.0 |
| ECN 10 | 9.0 | 5.3 | 7.3 | 4.1 |
| KLUCEL ® EF | 1.0 | 0.6 | 0.8 | 0.5 |
| Talc | 2.0 | 1.2 | 1.6 | 0.9 |
| Dibutyl sebacate | 1.0 | 0.6 | 0.8 | 0.5 |
| Total | 100.0 | 58.9 | 100.0 | 55.9 |

Beads coated with the EUDRAGIT® system showed a tendency to block (clump) into the run. Extended release beads prepared with the HPC/EC system were evaluated for assay and dissolution. The results are described in Table 6.

TABLE 6

| Lot # | % Label Claim |
|---|---|
| NK15-144-01 (11.7%) | 97.4 |
| NK15-144-12 (13.3%) | 93.0 |
| NK15-144-23 (15.0%) | 94.4 |
| NK15-157-01 (7.5%) | 92.8 |
| NK15-157-12 (10.0%) | 95.9 |
| NK15-157-23 (11.7%) | 96.7 |

Exemplary ERDNP Formulation

A sustained release dosage form (beads) was developed using an HPC/EC coating system. The 12 hour targeted release profile was confirmed through in vitro dissolution testing. The final formulation representing the DNP drug spheres is illustrated in Table 7.

TABLE 7

| Ingredient | % w/w | g/batch | mg/dose |
|---|---|---|---|
| Mannitol | 65.8 | 394.8 | 32.9 |
| MCC | 32.0 | 192.0 | 16.0 |
| HPMC | 0.2 | 1.2 | 0.1 |
| 2,4-DNP | 2.0 | 12.0 | 1.0 |
| Total | 100.0 | 600.0 | 50.0 |

These drug spheres were used to generate the controlled-release DNP drug with composition as illustrated in Table 8.

TABLE 8

| Ingredient | % w/w | mg/dose |
|---|---|---|
| 2,4-DNP drug spheres | 89.5 | 50.0 |
| ECN 10 | 7.3 | 4.1 |
| KLUCEL ® EF | 0.8 | 0.5 |
| Talc | 1.6 | 0.9 |
| DBS | 0.8 | 0.5 |
| Total | 100.0 | 55.9 |

Example 2

Figure 2E:
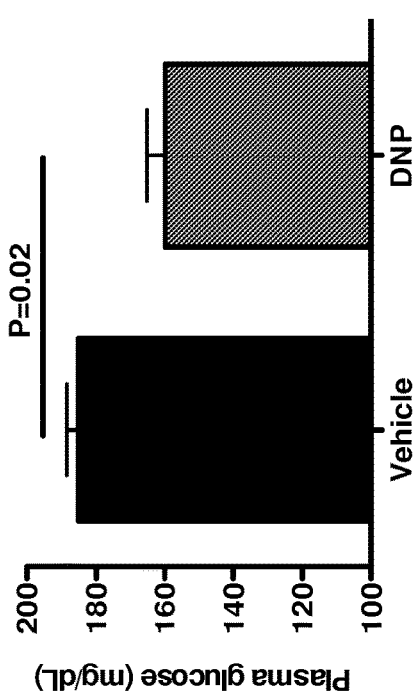
Figure 2F:
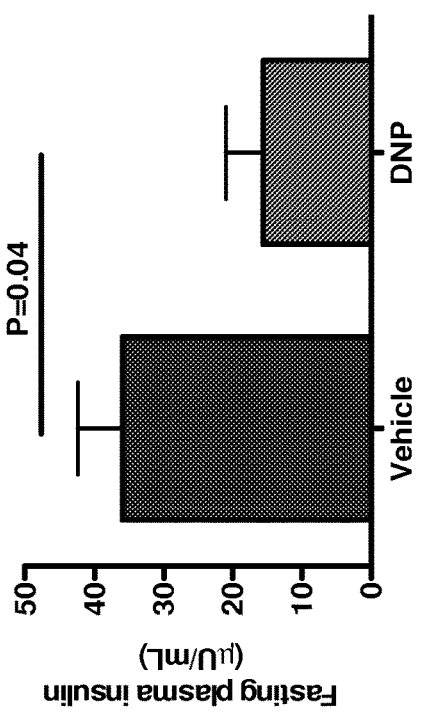
Figure 2G:
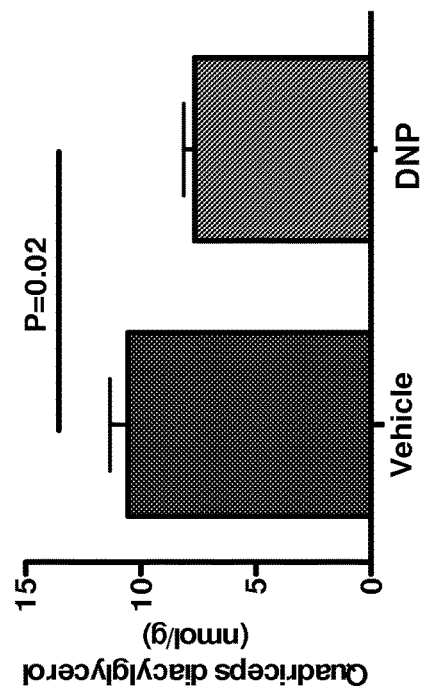
Figure 2H:
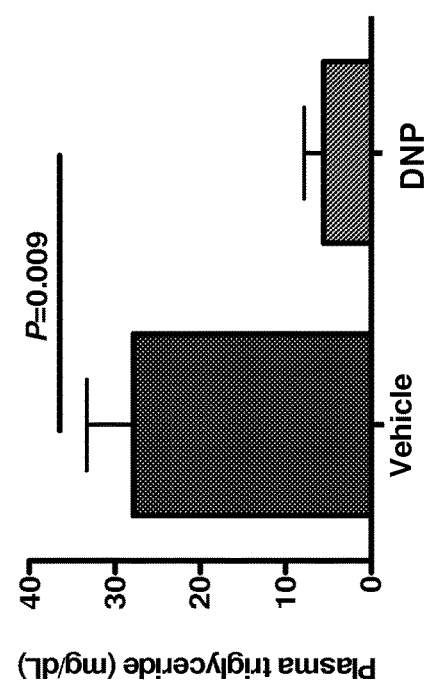
Figure 3:
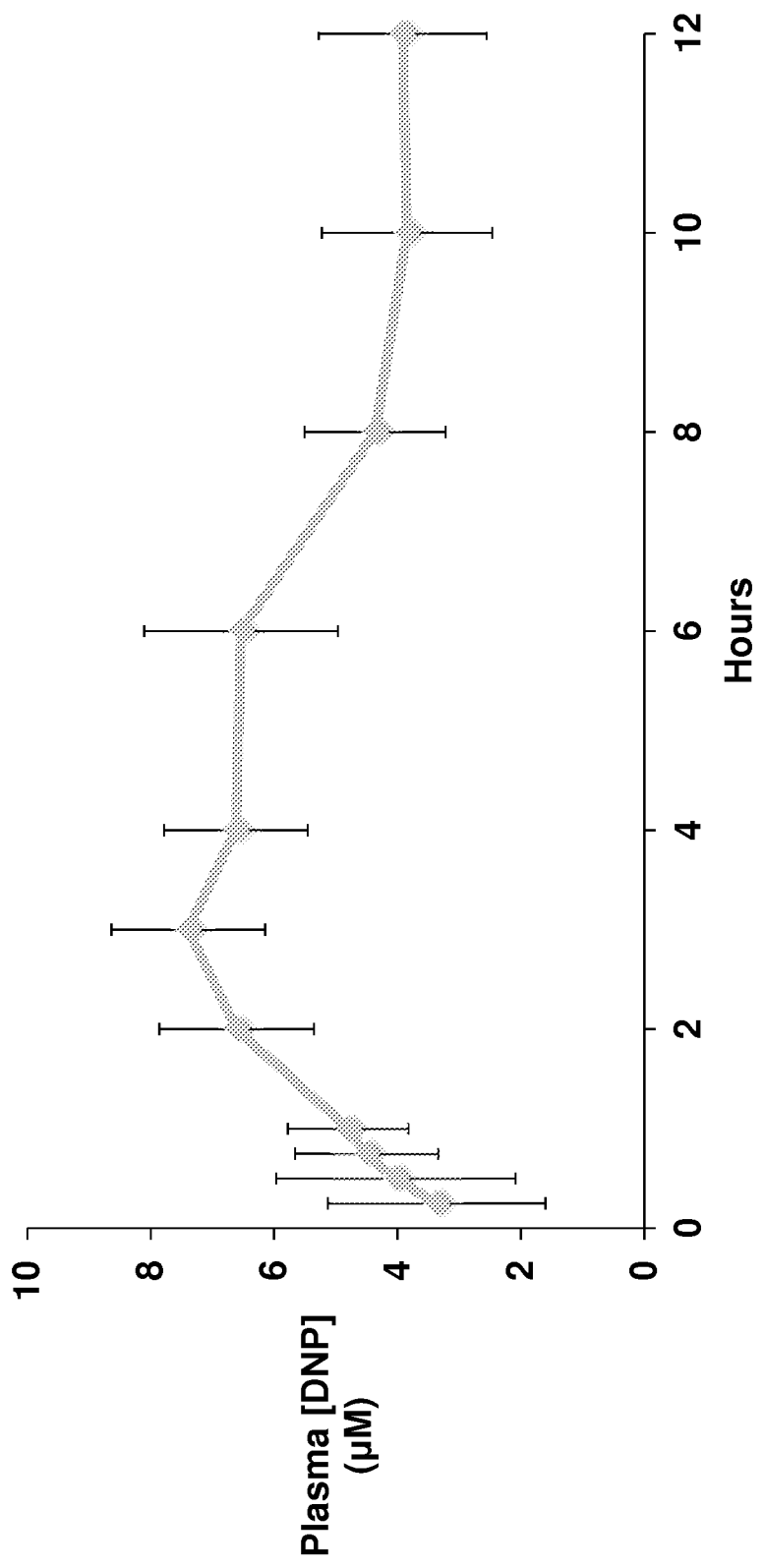
FIG. 3 is a graph illustrating plasma DNP concentrations after feeding rats extended release DNP (ERDNP) (1 mg/kg) in peanut butter at time 0. Treatment with ERDNP achieved a sustained plasma concentration of DNP between 3-8 µM for at least 12 hours.

Continuous Low Dose Intragastric DNP Reduced Liver and Muscle Lipid Content and Improved Whole Body Insulin Sensitivity In order to test whether a continuous, low dose intragastric infusion of DNP achieving sustained plasma DNP concentrations of ~3 µM would lead to reductions in hepatic steatosis and improve whole body insulin sensitivity, rats were infused with intragastric DNP (2 mg/kg per day) for 5 days. This infusion rate of intragastric DNP resulted in steady state plasma and tissue DNP concentrations of ~3 µM and ~1 µM in plasma and liver respectively with negligible concentrations of DNP in skeletal muscle (FIG. 2A). By comparison, a dose of DNP (5 mg/kg) in the rat results in a peak plasma DNP concentration of ~120 µM and peak DNP liver concentrations of ~60 µM.

These very low concentrations of DNP resulted in marked (>80%) reductions in plasma triglycerides as well as >50% reductions in liver and muscle TAG and diacylglycerol (DAG) content. These reductions in liver and muscle TAG/DAG content were associated with marked improvements in whole body insulin sensitivity as indicated by lower fasting plasma glucose and insulin concentrations (FIGS. 1, 14A-14F, 14K-14L). In contrast to these marked improvements in whole body insulin sensitivity, there were no changes in tissue ceramide content and no systemic toxicities associated with these chronic intragastric DNP infusions as reflected by no observed changes in liver enzymes, blood urea nitrogen (BUN) or creatinine (FIGS. 14F-14J).

Example 3

Safety and Efficacy of ERDNP

Since these continuous intragastric DNP infusion studies demonstrated that sustained plasma and tissue concentrations of DNP in the 1-3 µM range reversed hepatic steatosis and insulin resistance in a rat model of NAFLD, safety and efficacy studies of an extended release DNP (ERDNP) formulation were performed, in which the formulation was fed to rats mixed in small amounts (~1 g) of peanut butter.

Figure 4A:
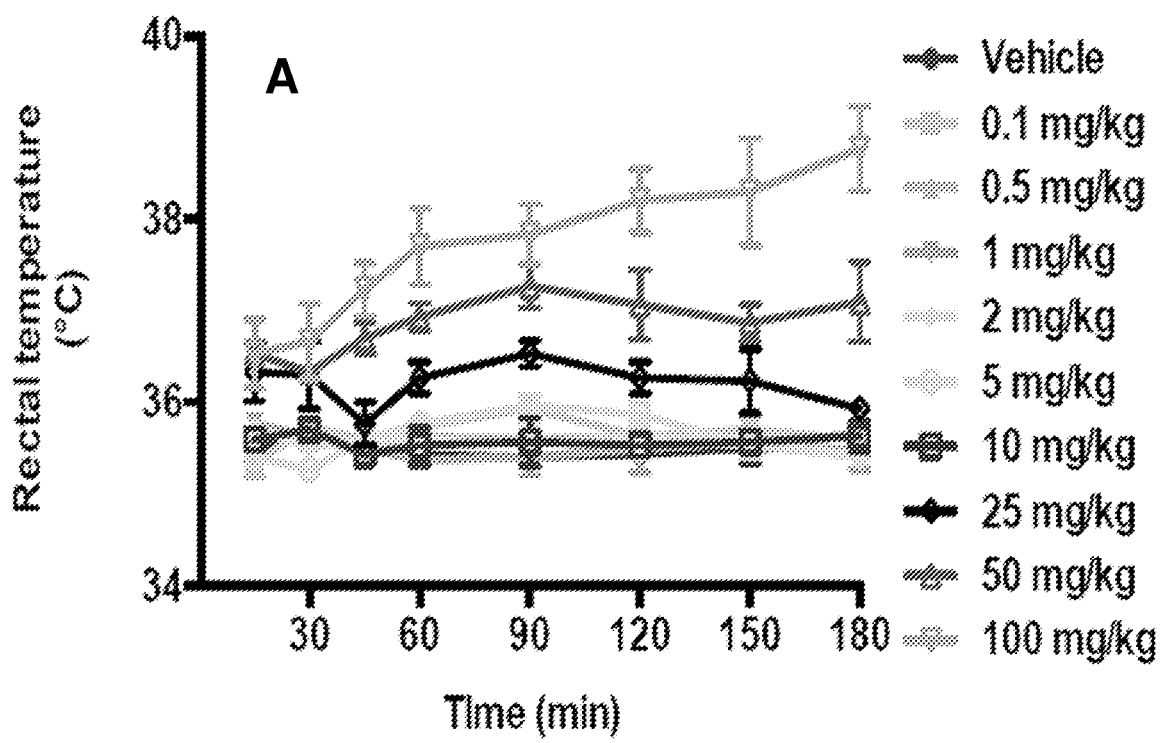
FIGS. 4A-4D, illustrates the finding that ERDNP has a 500-fold wider ratio of effective to safe dose than DNP.
Figure 4B:
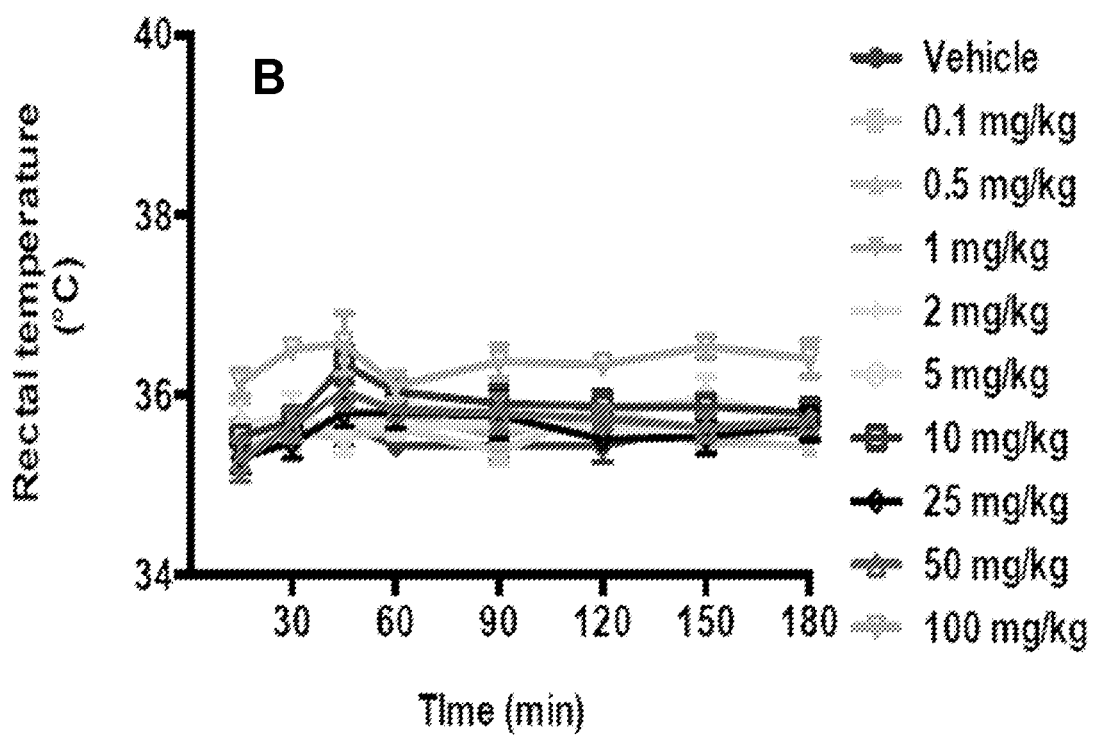

In contrast to DNP, which caused a dose dependent increase in body temperature and doses at and above 25 mg/kg, ERDNP had a negligible effect on body temperate, with only a detectable 0.5° C. increase at 100 mg/kg (FIGS. 4A-4B).

Figure 4C:
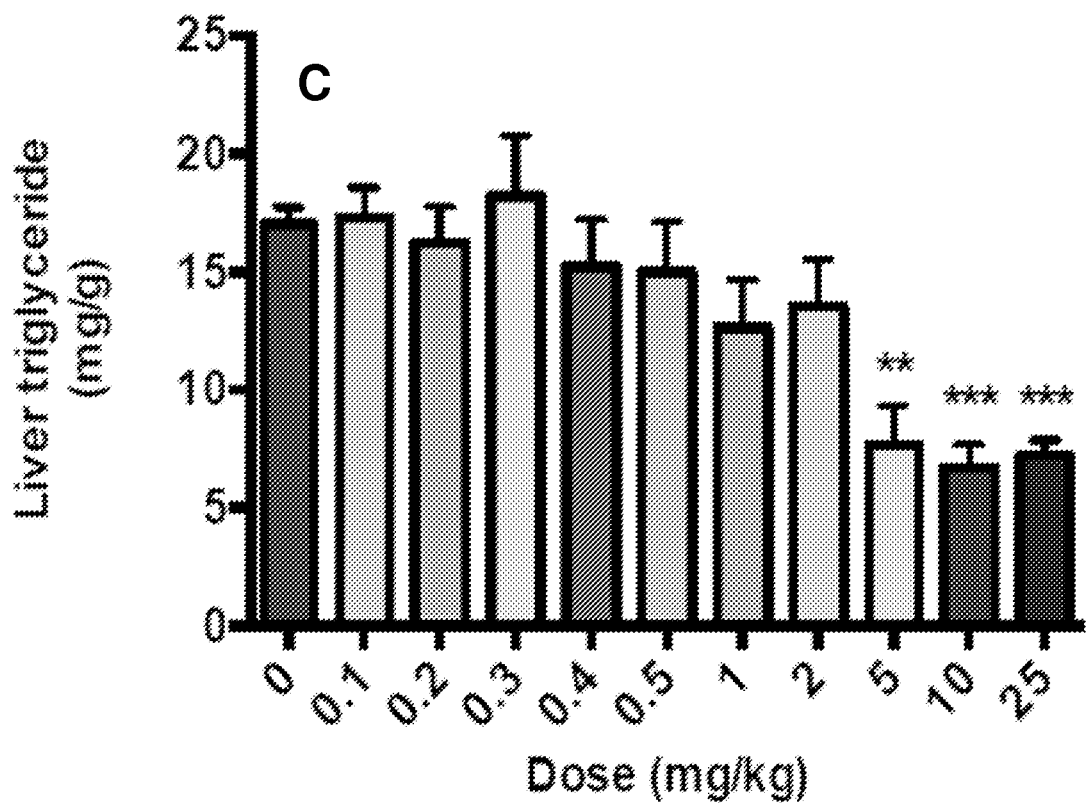
Figure 4D:
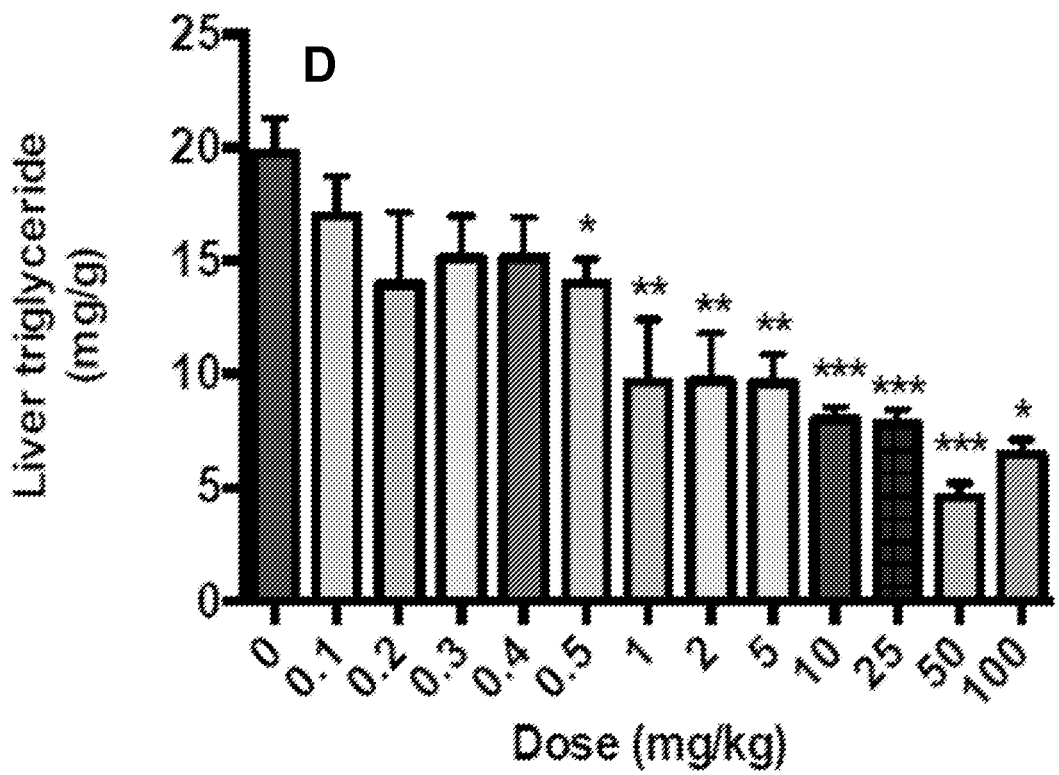

To compare the safety and efficacy of ERDNP and DNP at reversing diet-induced NAFLD, two-week high fat fed rats were treated with varying doses of ERDNP or DNP daily for five days. The lowest effective dose of ERDNP to decrease liver triglyceride was 0.5 mg/kg, whereas that of DNP was 5 mg/kg (FIGS. 4C-4D). No changes to alanine aminotransferase (ALT), aspartate aminotransferase (AST), BUN or creatinine were observed with any of the doses of ERDNP, whereas daily DNP treatment at doses above 1 mg/kg raised AST concentrations, doses above 2 mg/kg raised ALT, and the highest dose of DNP raised BUN (FIGS. 15A-15H). Thus the ratio of toxic (100 mg/kg) to therapeutic dose (0.5 mg/kg) was 200 for ERDNP, as compared to 0.4 (toxic dose 2 mg/kg, therapeutic dose 5 mg/kg) for DNP, yielding a 500 fold improvement in the toxic to effective dose ratio for ERDNP compared to DNP.

Example 4

Pharmacokinetics of ERDNP and DNP

Figures 5A, 5B, 5C, 5D:
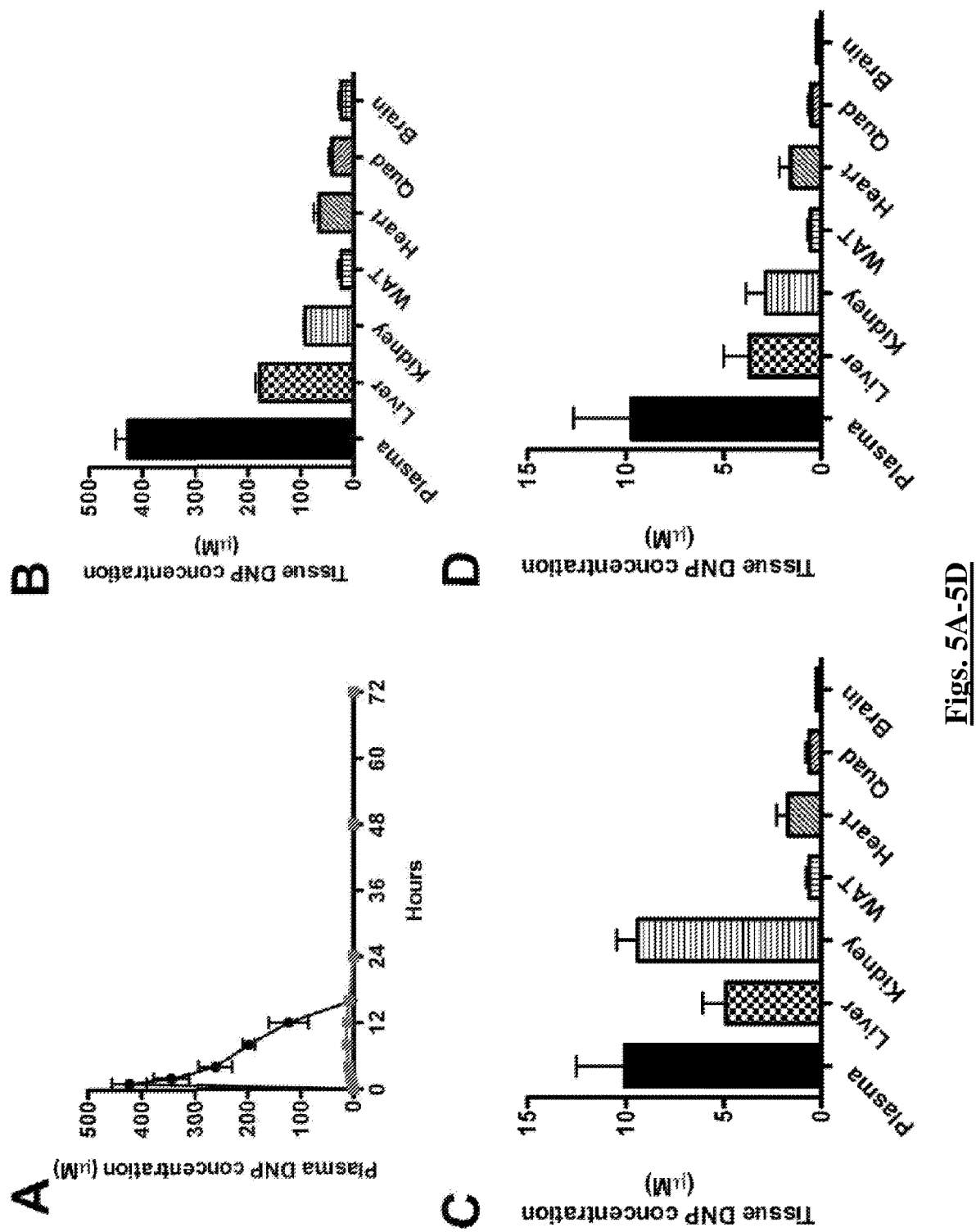
FIGS. 5A-5F, illustrates the finding that ERDNP is better tolerated than DNP because it results in lower plasma and tissue DNP concentrations.
Figures 5E, 5F:
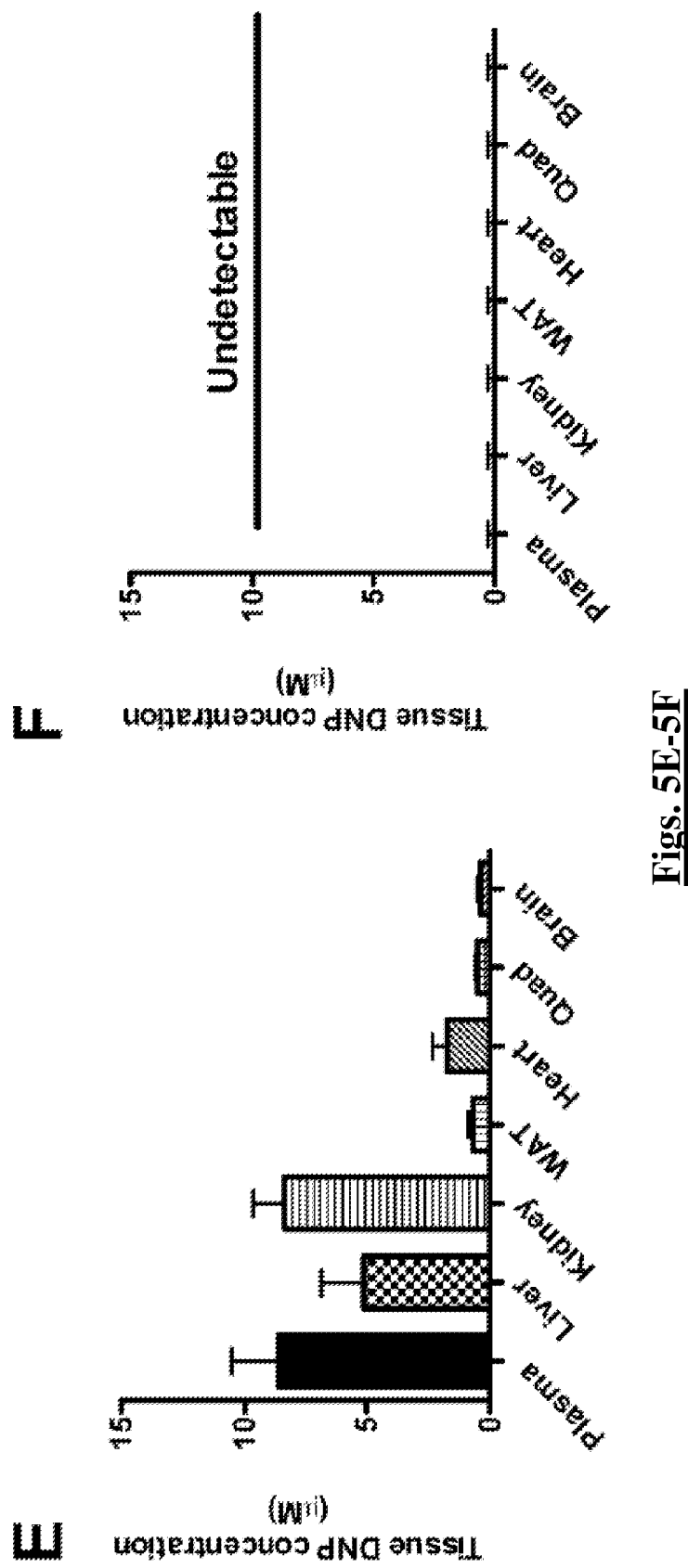
Figures 6A, 6B, 6C, 6D:
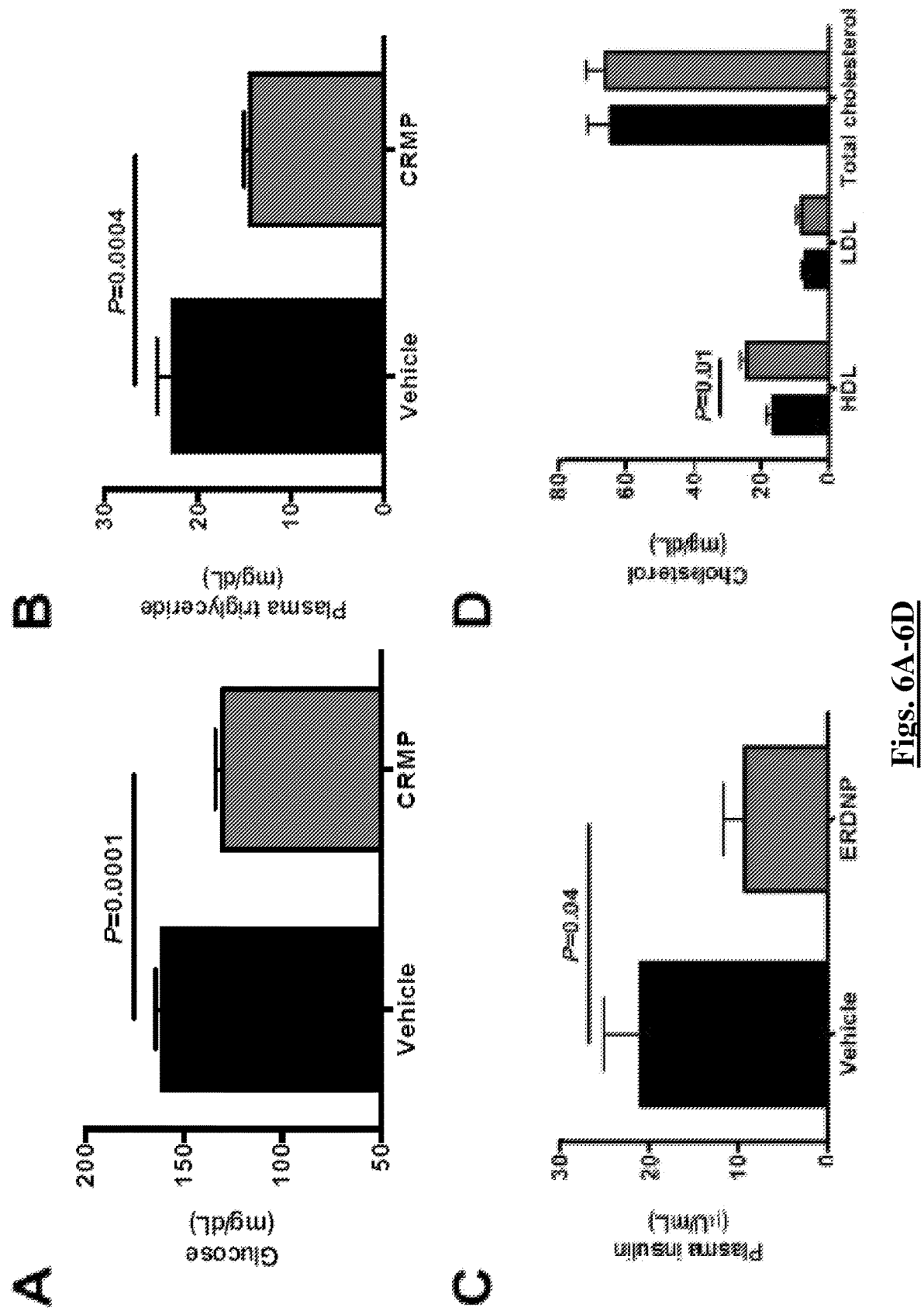
FIGS. 6A-6G, illustrates the finding that ERDNP (1 mg/kg per day for 5 days) reverses NAFLD and improves glucose tolerance and insulin sensitivity in high fat fed Sprague-Dawley rats.
Figure 6E:
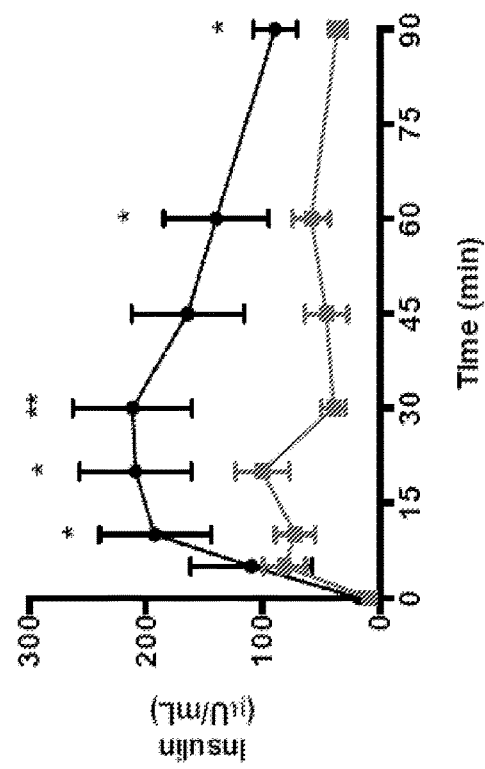
Figure 6F:
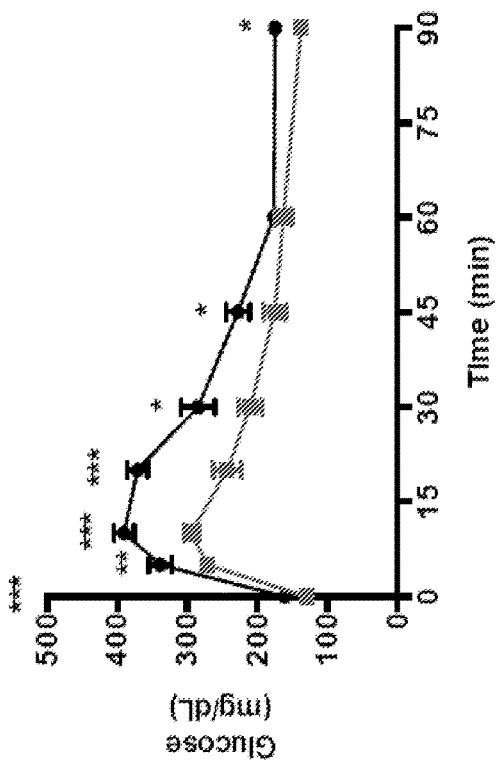
Figure 6G:
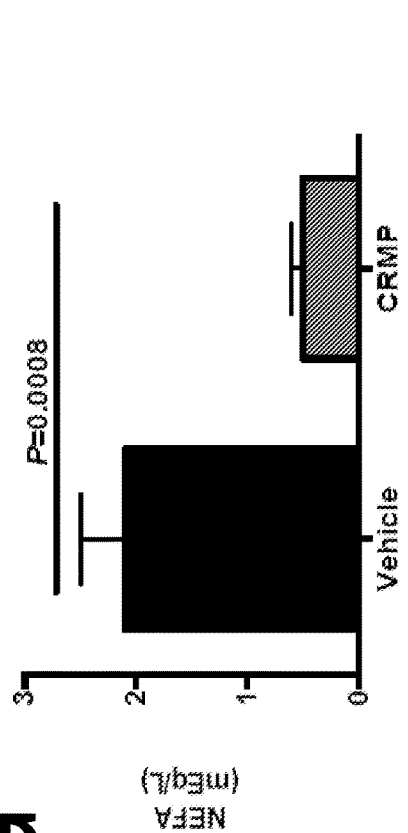

The improved safety to efficacy ratio of ERDNP relative to DNP was correlated with much lower plasma DNP concentrations with ERDNP compared to DNP. The area under the plasma DNP concentration curve was 20-fold in rats treated with 1 mg/kg ERDNP (effective dose used in these studies) versus 25 mg/kg DNP (lowest dose that produced an increase in body temperature) (211±18 vs. 4,311±555, P=0.001; FIG. 5A), with a time of maximum concentration of DNP just one hour with DNP treatment, versus 8-12 hours after treatment with ERDNP. The maximum plasma concentration of DNP was 30-fold higher with DNP treatment than with ERDNP, but the half-life of ERDNP was twice as long (8-12 hours for DNP vs. 16-24 hours for ERDNP). As predicted by the plasma concentration data, tissue DNP concentrations were 10-20-fold lower following both one and five days of 1 mg/kg ERDNP treatment than in rats treated once with 25 mg/kg DNP (FIGS. 5B-5D). There were no differences in tissue DNP concentrations in rats treated for 6 weeks with DNP (FIG. 5E) compared to rats treated for 1 or 5 days. As predicted by these data, tissue DNP concentrations 24 hours after a dose of ERDNP were undetectable (FIG. 5F), as were tissue concentrations of DNP at 48 and 72 hours after ERDNP treatment, demonstrating that DNP does not accumulate in tissues with chronic ERDNP treatment.

Figures 21I, 21J, 21K, 21L:
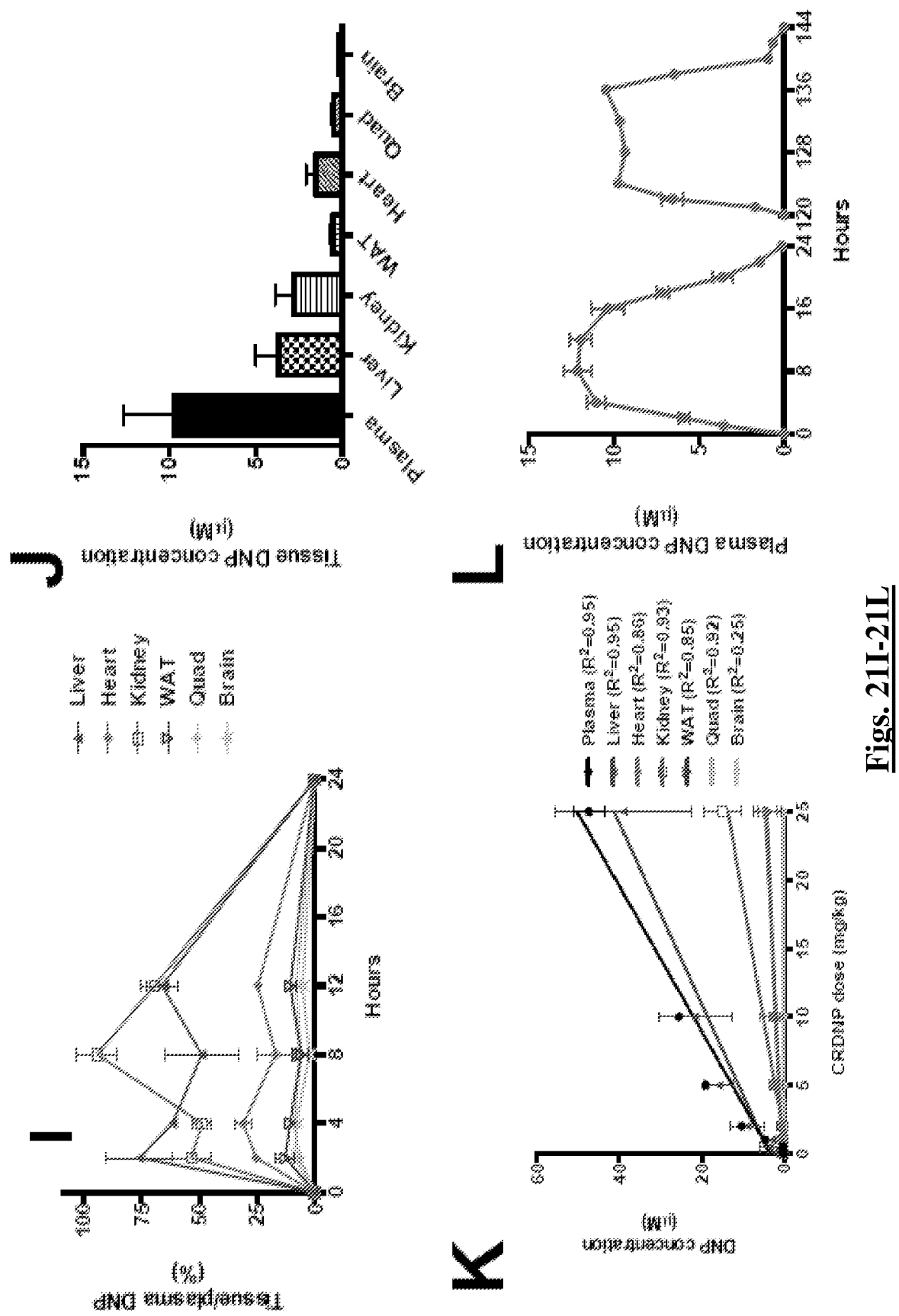
Figures 22A, 22B, 22C, 22D:
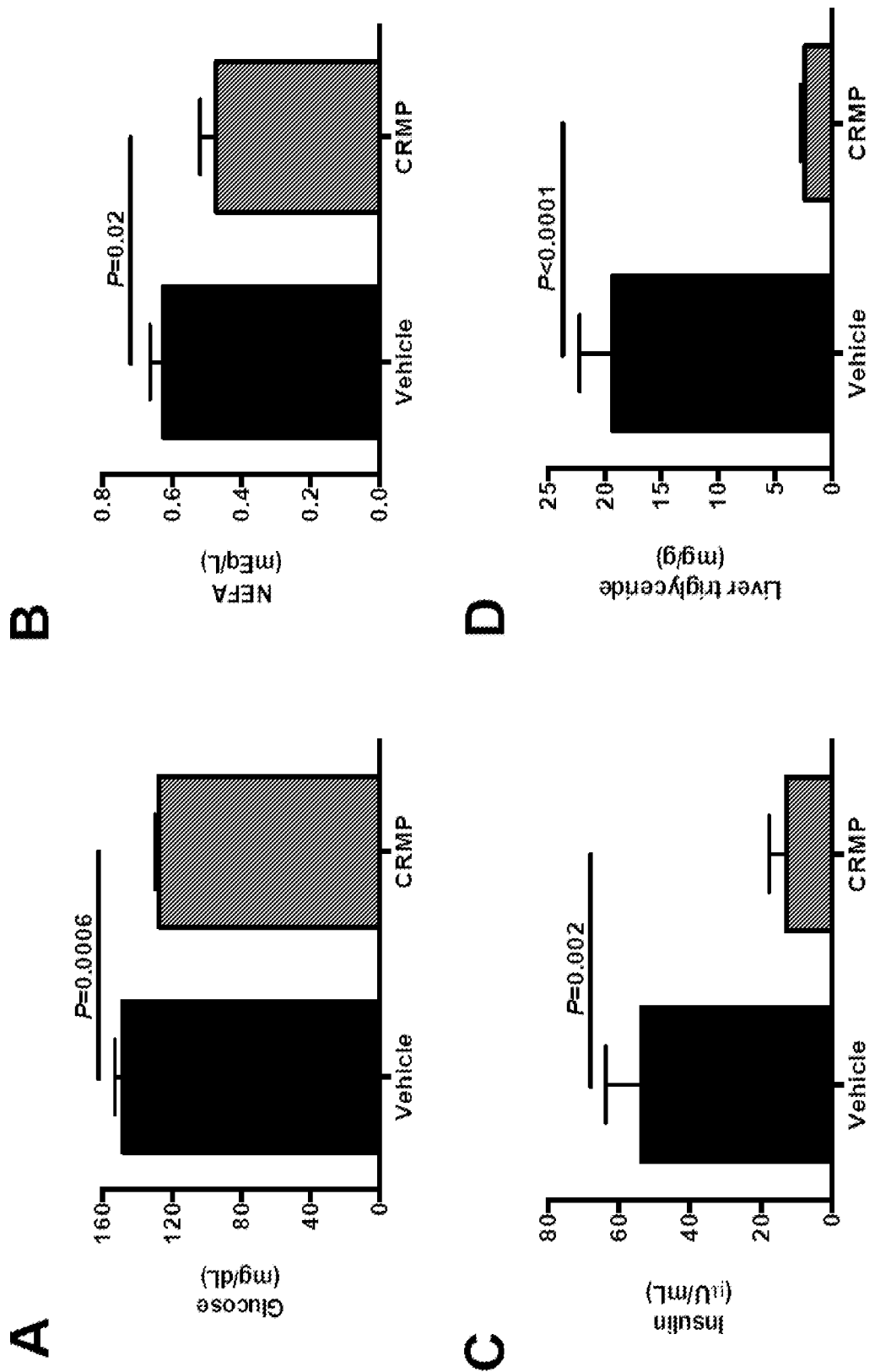
FIGS. 22A-22F, illustrates the finding that two weeks of daily ERDNP treatment (1 mg/kg) prevented NAFLD and insulin resistance in rats concurrently fed high fat diet.
Figures 22E, 22F:
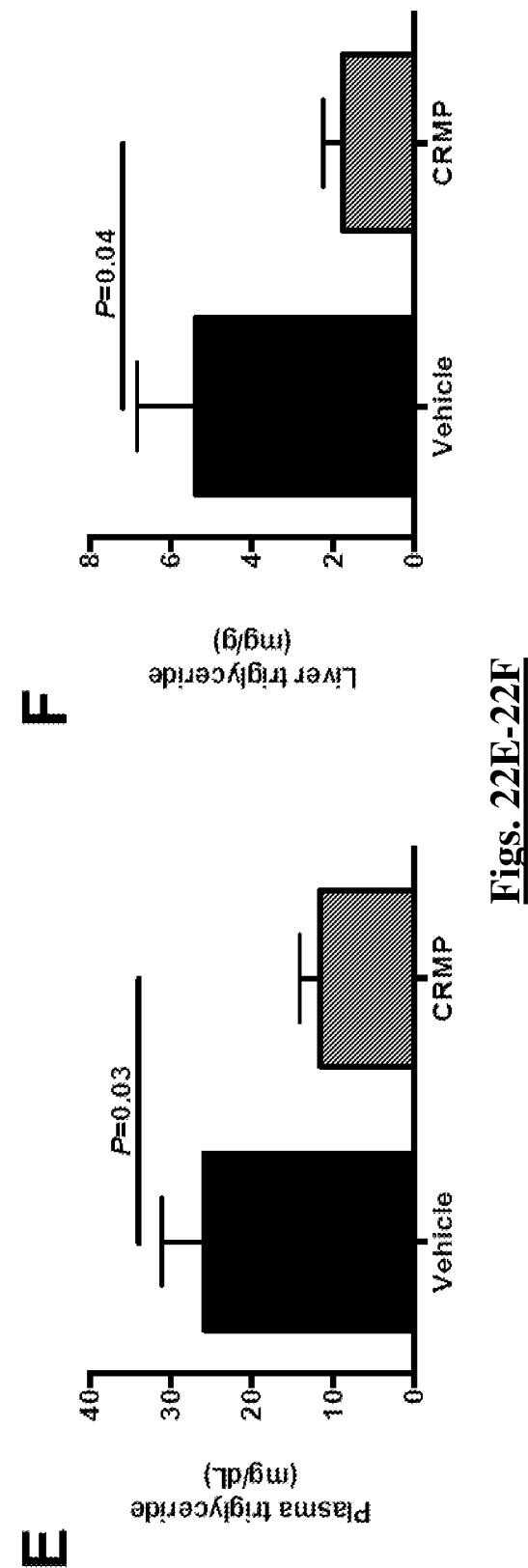
Figures 23A, 23B, 23C, 23D:
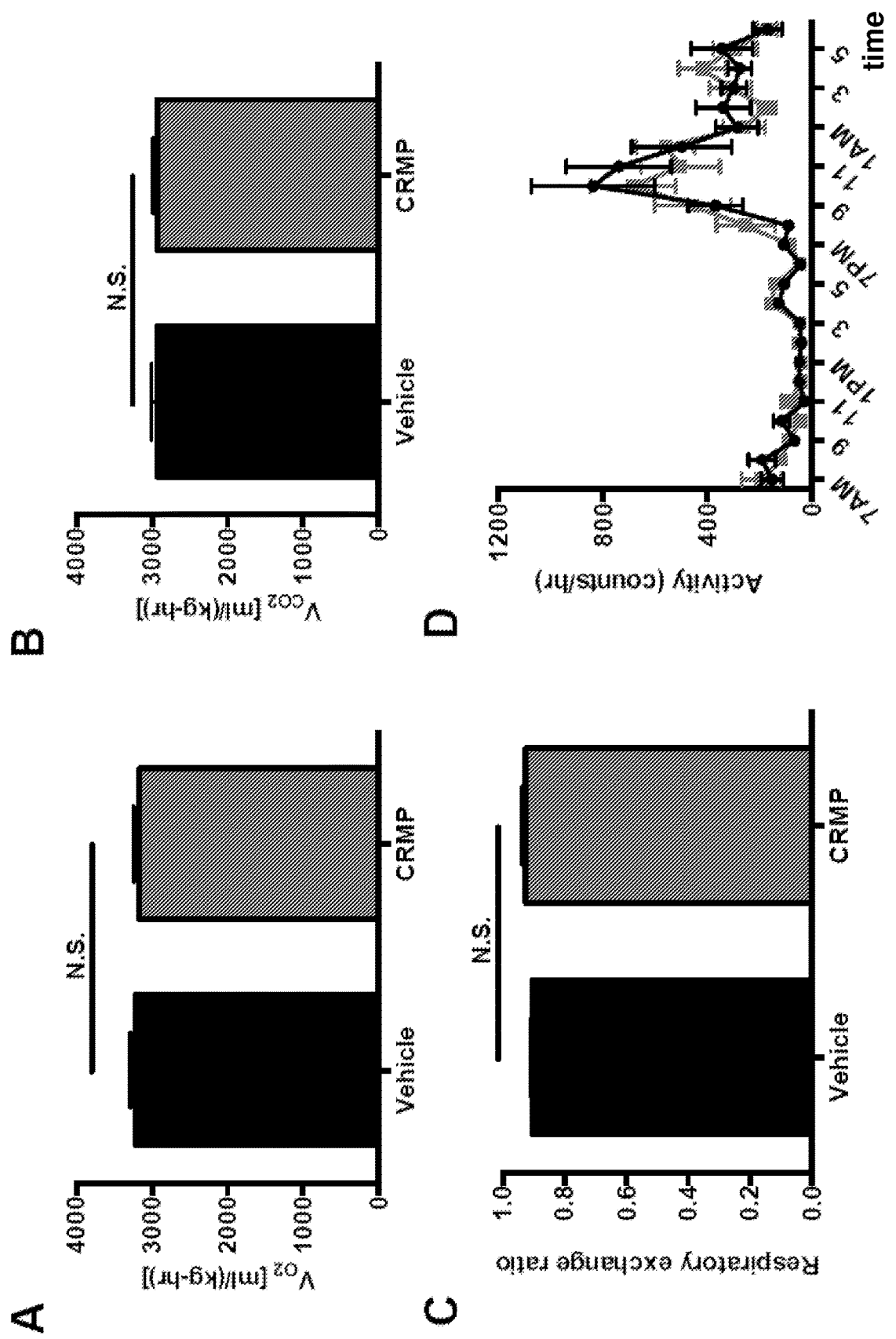
FIGS. 23A-23H, illustrates the finding that ERDNP did not cause any physiologically significant difference in any parameter measured in metabolic cage analysis in mice.
Figures 23E, 23F, 23G, 23H:
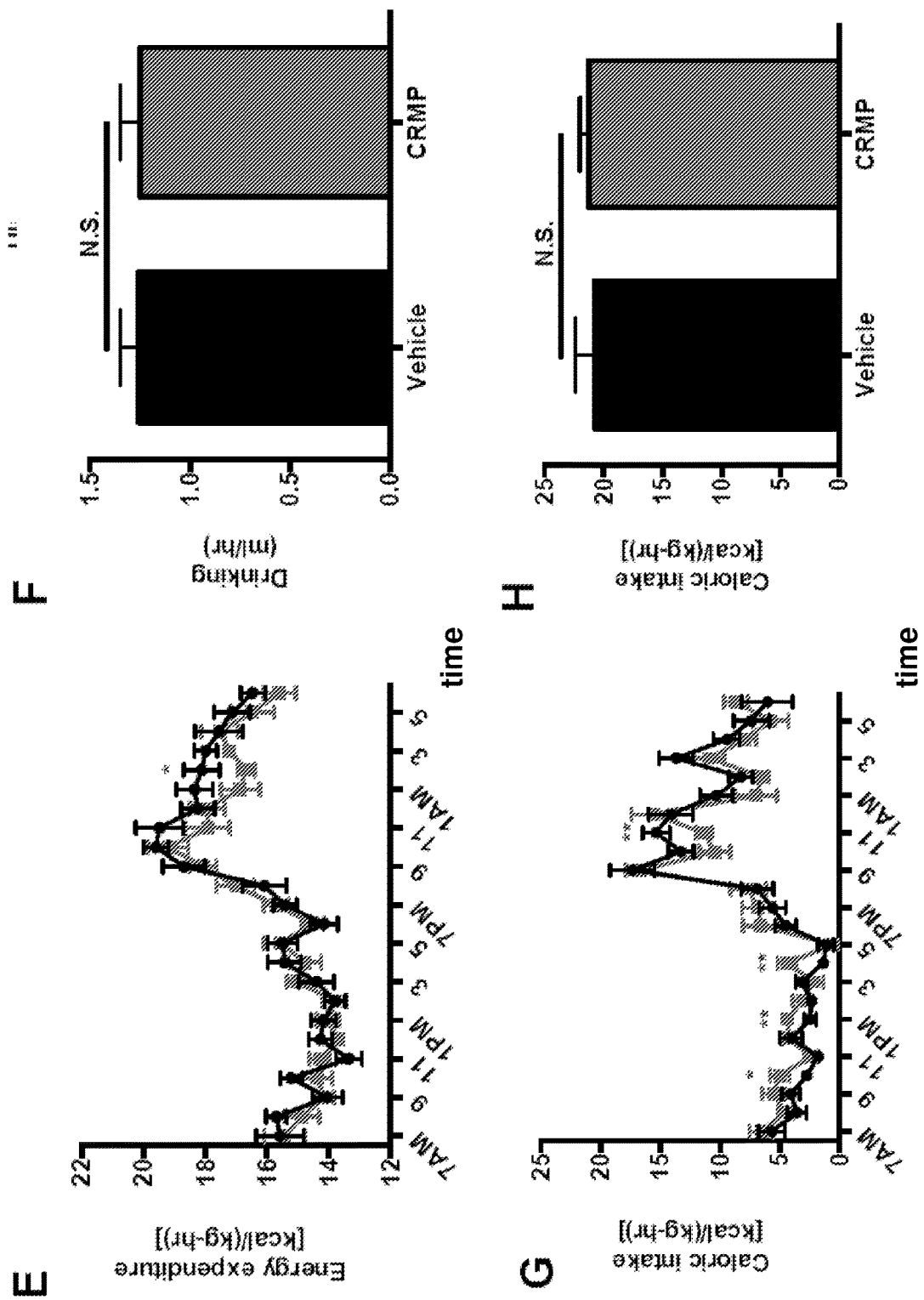

Although peak plasma DNP concentrations following 1 mg/kg treatment were not different between rats treated with DNP and ERDNP, the area under the curve of DNP concentration was doubled with treatment with CRNDP relative to DNP, likely accounting for ERDNP's improved efficacy at equimolar doses (FIGS. 4C-4D, 21A-21E). A strong correlation was observed between plasma DNP concentration and body temperature (FIG. 21F). In certain embodiments, DNP toxicity is a function of the maximum plasma DNP concentration. Tissue concentrations of DNP following 1 mg/kg ERDNP treatment (effective dose) were 25-100-fold lower than DNP concentrations after the lowest toxic dose of DNP (25 mg/kg), without any change in the ratio of plasma/tissue DNP after plasma DNP concentrations had plateaued (FIGS. 21G-21I). Tissue DNP concentrations 24 hours after a dose of ERDNP were undetectable (below the lower limit of detection of the method, 0.05 μM) (FIG. 21H), as were tissue concentrations of DNP 48 and 72 hours after ERDNP treatment, demonstrating that DNP does not accumulate in tissues with chronic ERDNP treatment. Accordingly, DNP concentrations following chronic DNP treatment did not differ significantly from tissue concentrations after one ERDNP treatment, and were under 10 μM in all tissues (FIG. 21J). Tissue DNP concentrations correlated linearly with ERDNP dose other than in brain where measured DNP concentrations were at the lower limit of detection of the method (0.05 μM) (FIG. 21K), implying the absence of dose-dependent tissue DNP metabolism. In concert with this, plasma DNP concentrations were not different after chronic (5 daily) doses of 1 mg/kg ERDNP than after the first dose (FIG. 21L).

Six weeks of treatment with ERDNP at 1 mg/kg was similarly well tolerated and did not result in any alterations in behavior, food intake, body weight, body temperature, elevations in liver enzymes (ALT/AST), BUN, or creatinine and there was no evidence of cellular injury or necrosis in liver or kidney histology (FIGS. 16A-16G).

Tissue DNP concentrations following the last dose did not differ from tissue DNP concentrations after one or five daily doses of ERDNP (FIG. 16H). Without wishing to be limited by any theory, the toxicity of a DNP derivative can be predicted by the maximum concentration of DNP, whereas its efficacy can be predicted by the area under the curve of plasma DNP concentrations.

Example 5

ERDNP Treatment Reduces Hypertriglyceridemia, Hepatic Steatosis and Insulin Resistance To examine whether ERDNP reduces tissue lipid content and improve whole body insulin sensitivity, a well-established high fat fed rat model of NAFLD and insulin resistance was treated with daily ERDNP (1 mg/kg) or vehicle for five days. Despite identical body weight at the time of study, the ERDNP treated rats had an approximately 30-40% reduction in fasting plasma glucose, fatty acid and triglyceride concentrations, a 30% increase in high density lipoprotein concentration and a 50% reduction in plasma insulin concentrations (FIGS. 6A-6D, 17A-17B).

Rats treated with ERDNP manifested improved glucose tolerance, with lower plasma glucose and insulin concentrations during an intraperitoneal (IP) glucose tolerance test (FIGS. 6E-6F, 17G-17H).

Figures 7A, 7B, 7C, 7D:
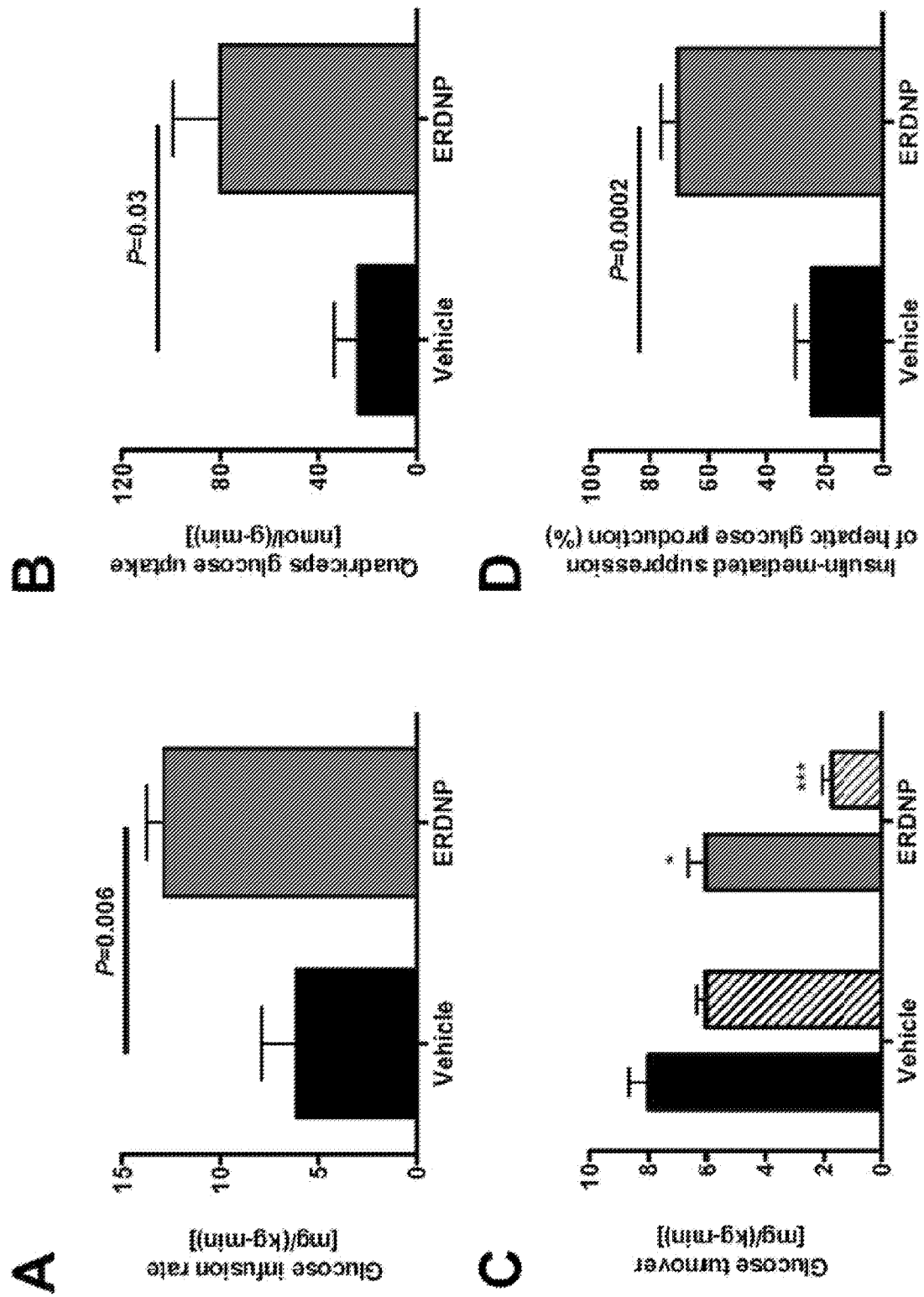
FIGS. 7A-7D, illustrates the finding that ERDNP (1 mg/kg per day for 5 days) improves insulin sensitivity in high fat fed rats.
Figures 18A, 18B, 18C, 18D:
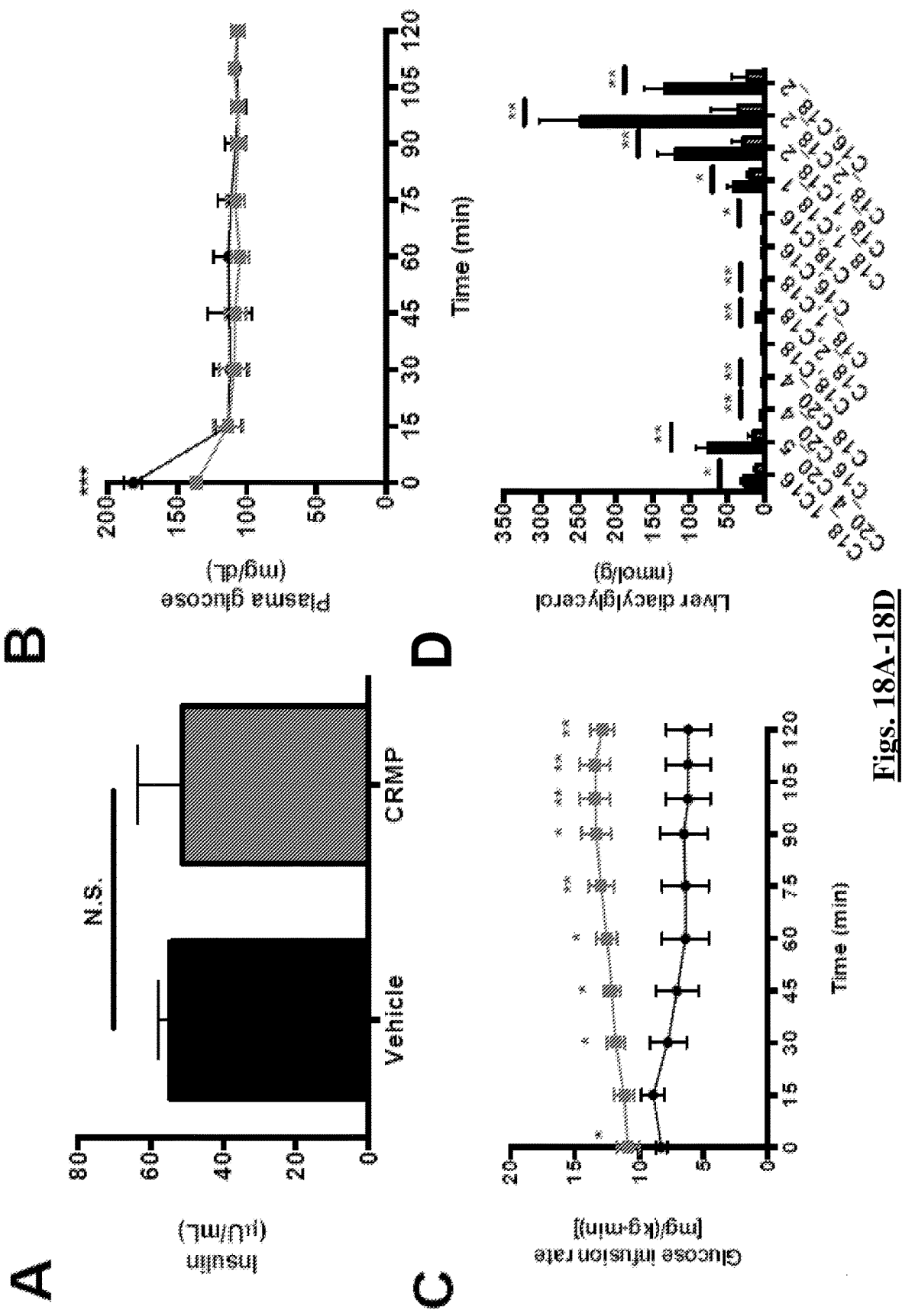
FIGS. 18A-18Z, illustrates the finding that ERDNP (1 mg/kg per day for 5 days) ameliorates NAFLD improves insulin sensitivity in high fat fed rats.
FIG. 18B: Plasma glucose concentrations throughout the clamp.
FIG. 18C: Glucose infusion rate during the clamp.
FIGS. 18D-18E: Liver and quadriceps DAG species.
Figure 18E:
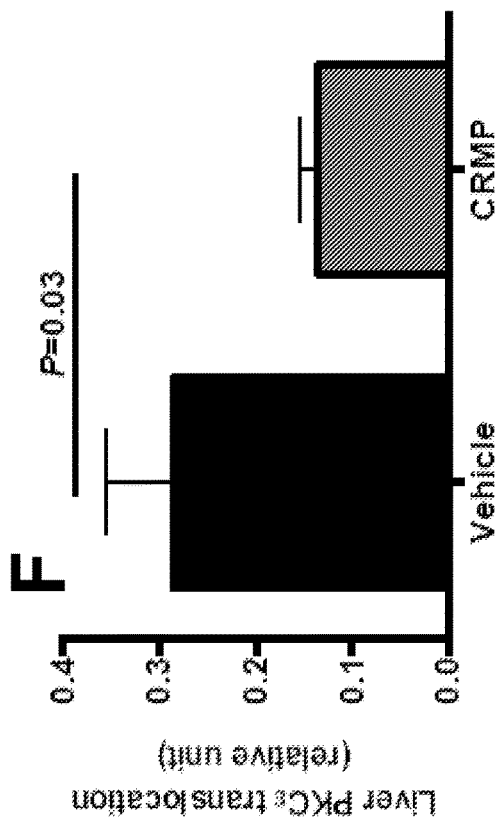
Figure 18F:
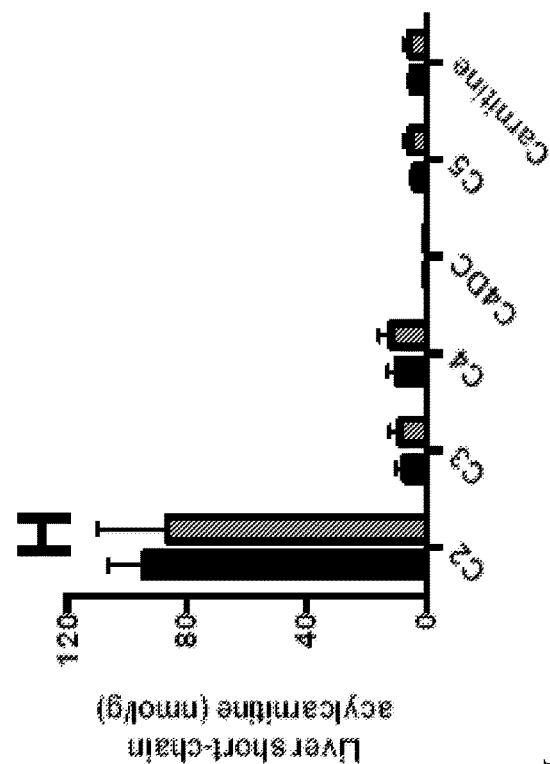
FIGS. 18F-18G: Liver PKCε and quadriceps PKCθ translocation.
Figure 18G:
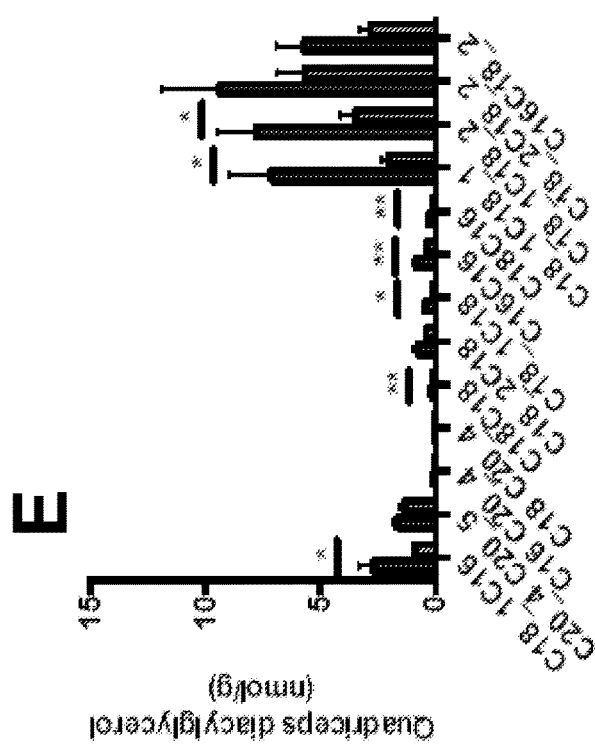
Figure 18H:
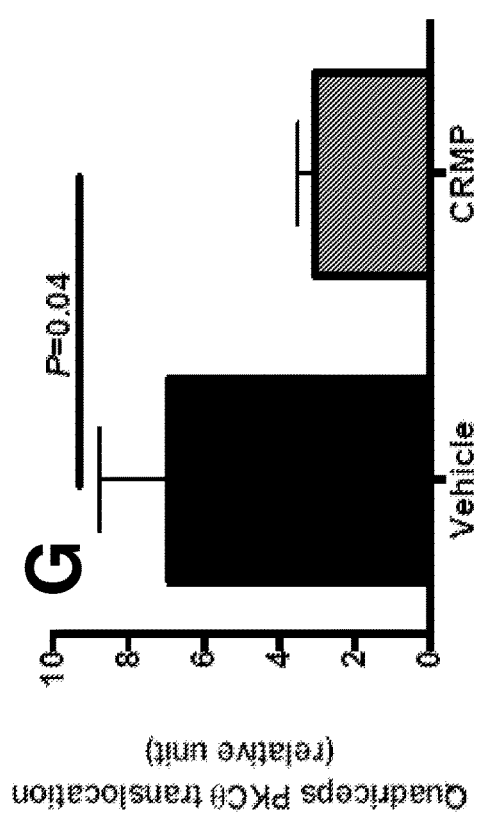
FIGS. 18H-18J: Liver acylcarnitine concentrations.
Figures 18I, 18J, 18K, 18L:
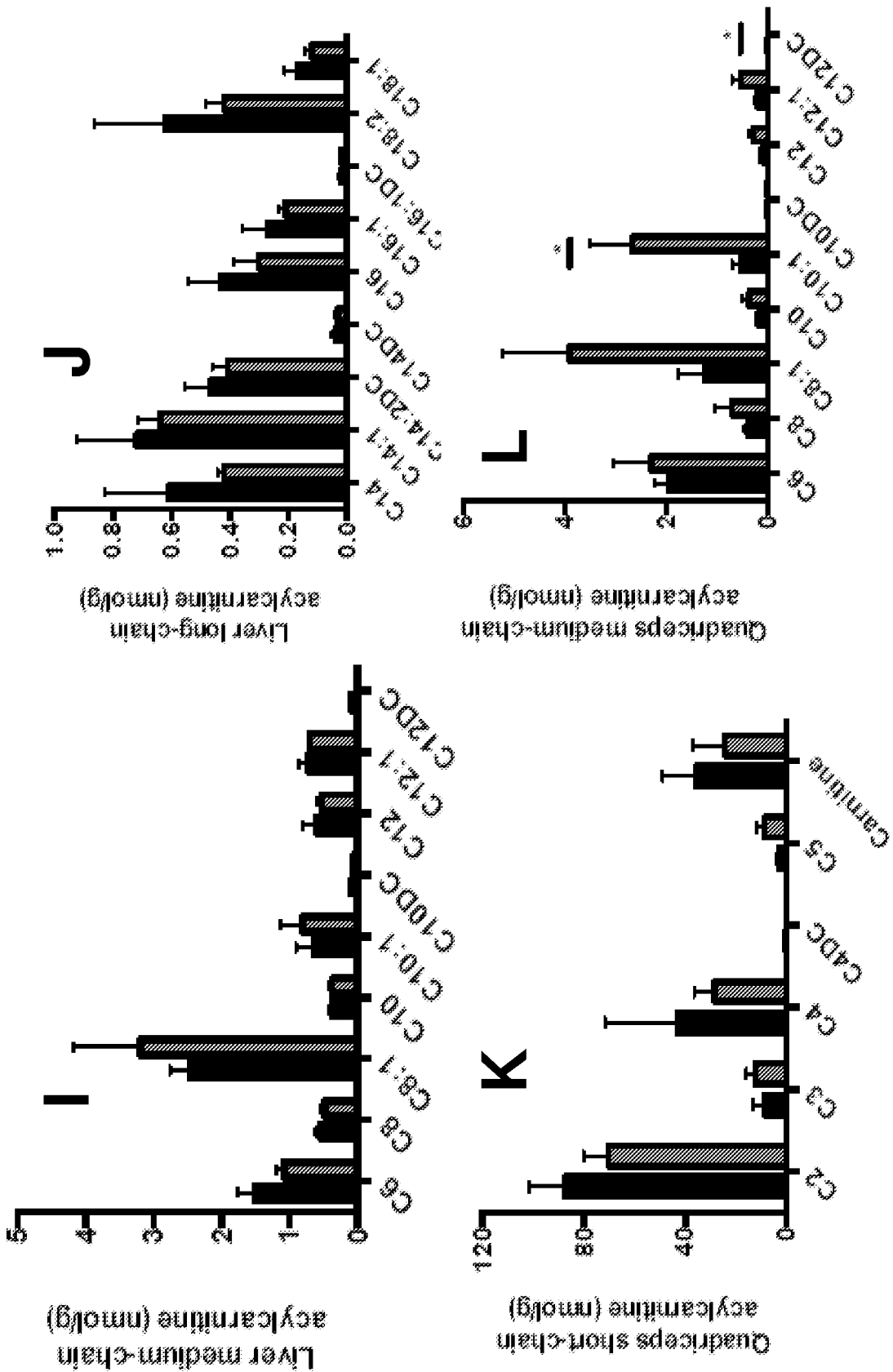
FIGS. 18K-18M: Quadriceps acylcarnitine concentrations.
Figures 18M, 18N, 18O, 18P:
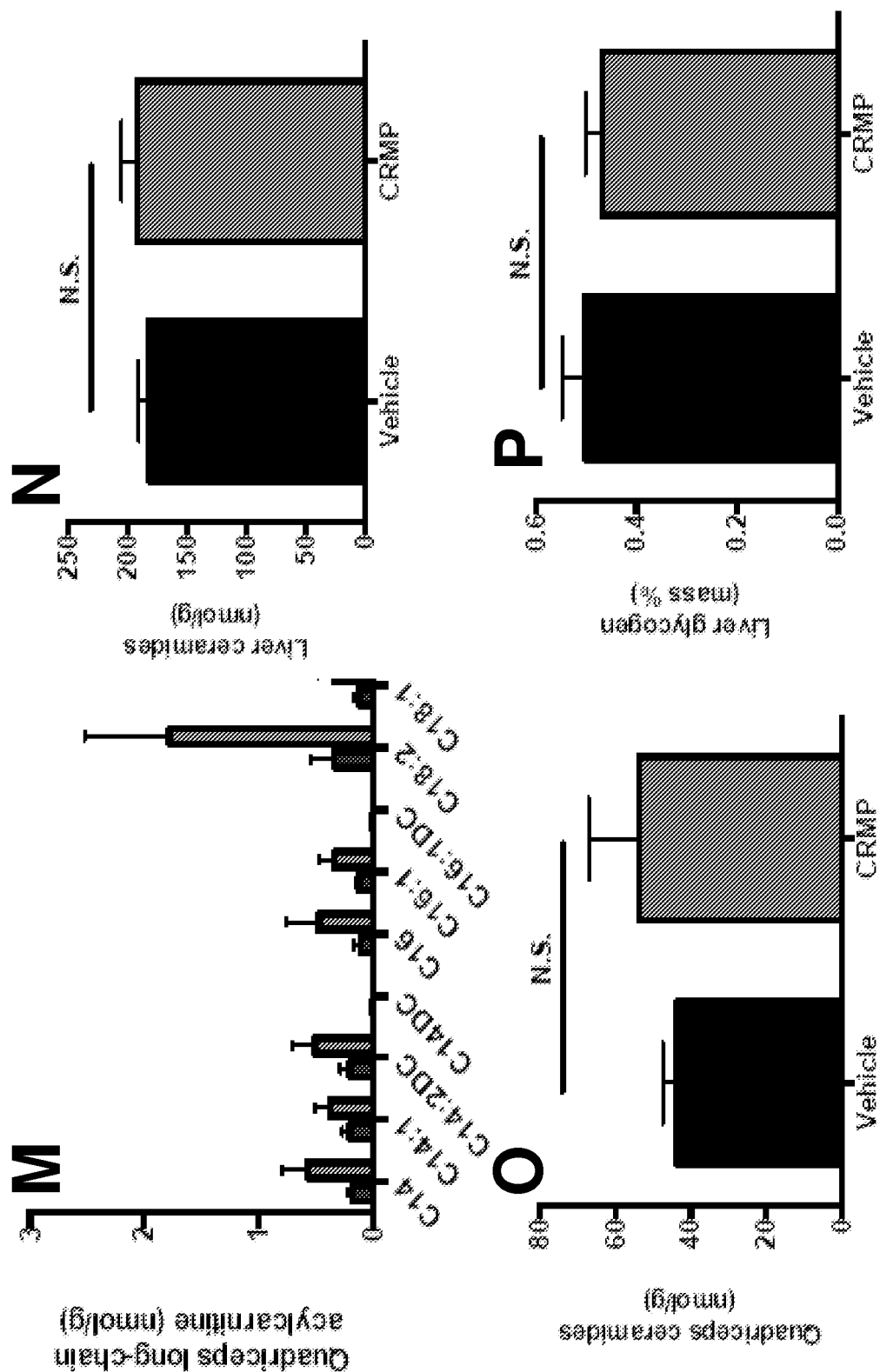
FIGS. 18N-18O: Liver and quadriceps ceramide concentrations.
FIG. 18P: Liver glycogen content.

In order to more fully assess the effect of ERDNP on whole body insulin sensitivity, hyperinsulinemic-euglycemic clamps combined with radiolabeled glucose were performed to assess insulin action in liver and skeletal muscle (FIGS. 18A-18B). Consistent with improved whole body insulin sensitivity by IP glucose tolerance tests, the ERDNP-treated rats required two-fold more glucose to maintain euglycemia during the hyperinsulinemic-euglycemic clamp study (FIGS. 7A, 18C). This improvement in insulin-stimulated whole body glucose metabolism in the ERDNP treated animals could be attributed to increases in both liver and muscle insulin sensitivity as reflected by a 2.5-fold increase in insulin-stimulated peripheral muscle glucose uptake (FIG. 7B) and a three-fold greater suppression of hepatic glucose production in ERDNP-treated rats during the hyperinsulinemic-euglycemic clamp (FIGS. 7C-7D).

Figures 8A, 8B, 8C, 8D:
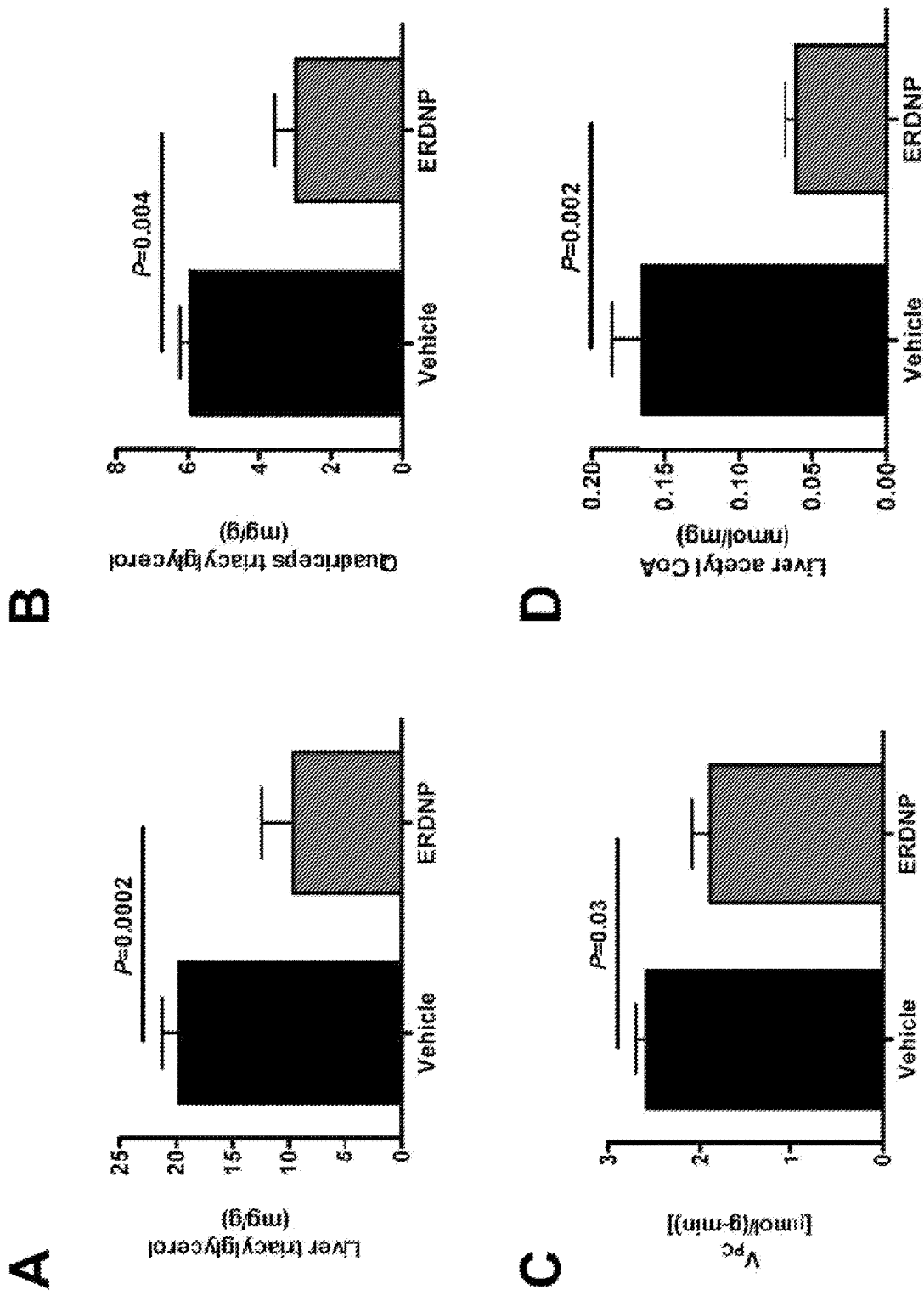
FIGS. 8A-8F, illustrates the finding that ERDNP (1 mg/kg per day for 5 days) reduces hepatic gluconeogenesis in high fat fed rats.

There may be a strong causal relationship between diacylglycerol (DAG)-induced nPKC activation and insulin resistance in liver and skeletal muscle. Consistently, ERDNP-treated rats had lower triacylglycerol (TAG) and DAG content and decreased protein kinase C (PKC)ε and PKCθ translocation in liver and skeletal muscle respectively (FIGS. 8A-8B, 18D-18G). As predicted by their lower fasting plasma glucose concentrations, flux through pyruvate carboxylase in the ERDNP-treated rats was 25% lower than controls, and this reduction in PC flux was associated with a 60% reduction in hepatic acetyl CoA, which is a key allosteric regulator of PC activity (FIGS. 8C-8D). In contrast there were no differences in gluconeogenic protein expression in the ERDNP-treated rats compared to the control animals (FIGS. 17C-17F).

Example 6

Figures 8E, 8F:
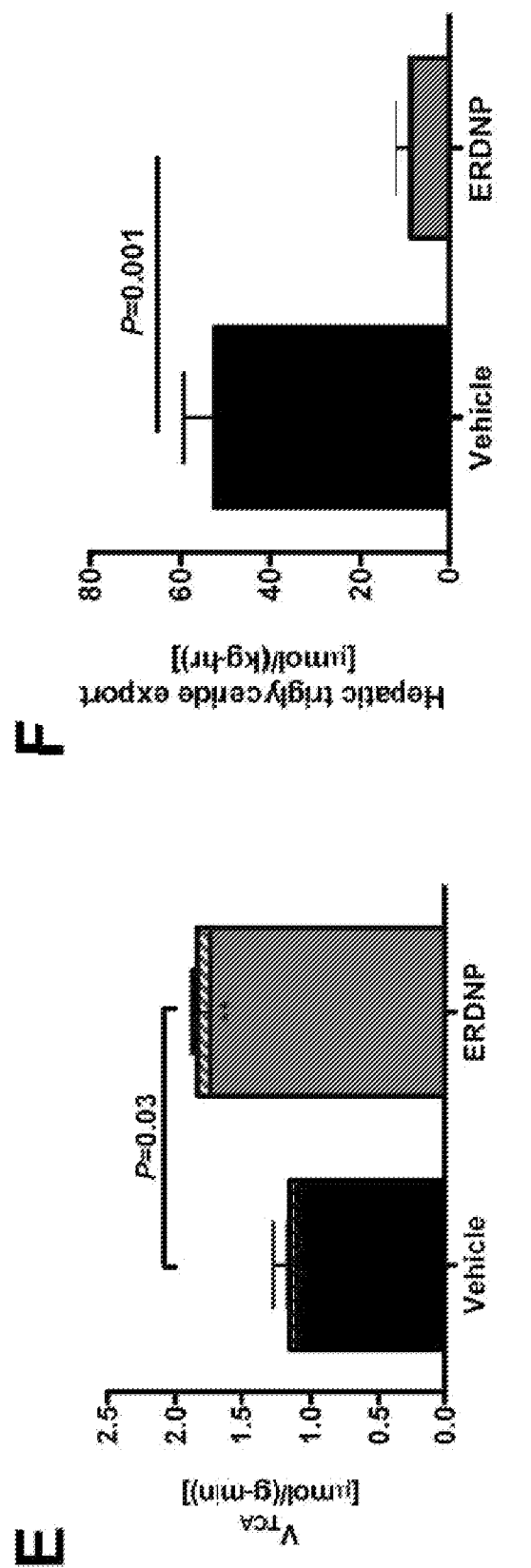
Figures 17A, 17B, 17C, 17D:
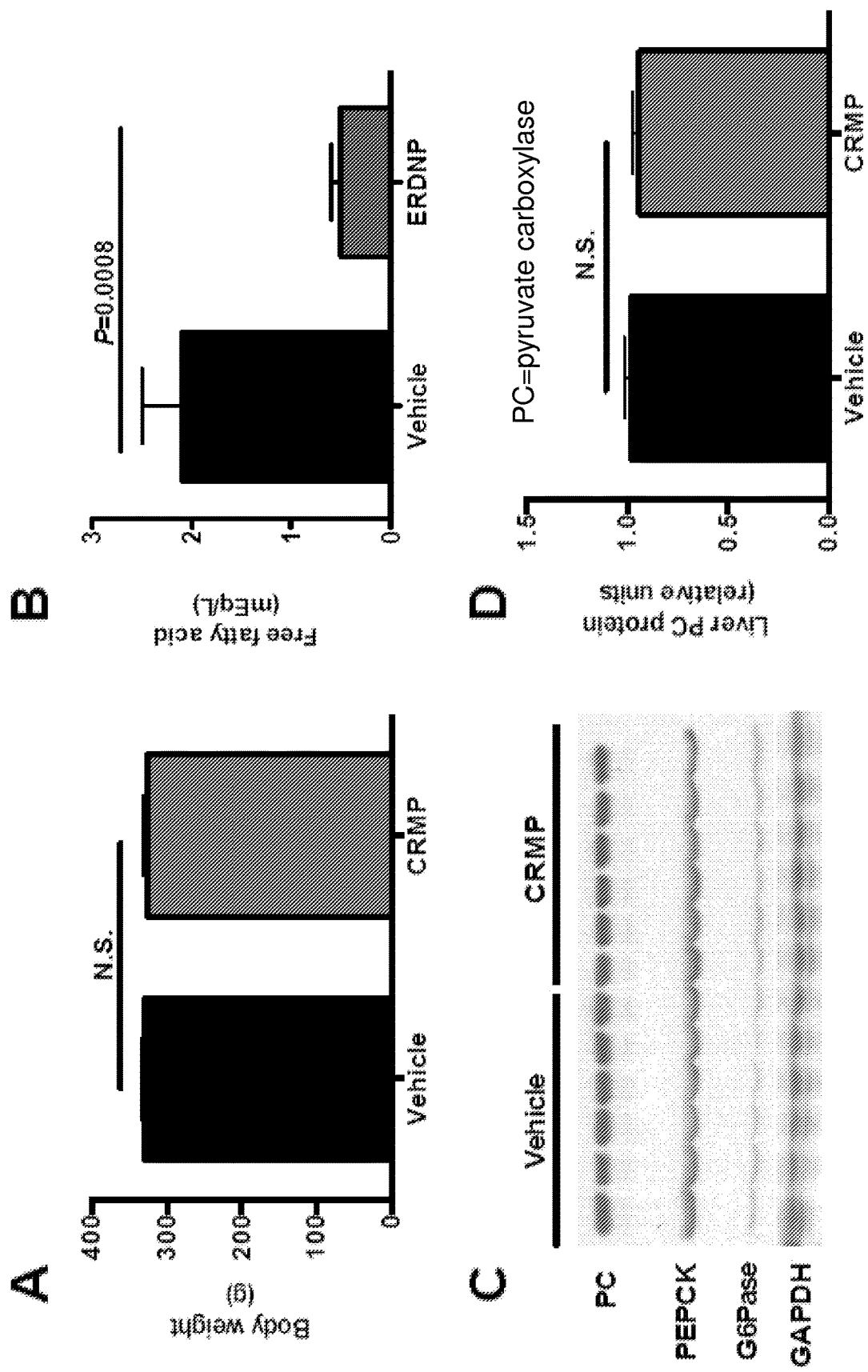
FIGS. 17A-17K, illustrates the finding that ERDNP (1 mg/kg per day for 5 days) reverses NAFLD and improves glucose tolerance and insulin sensitivity in high fat fed Sprague-Dawley rats.
Figures 17E, 17F, 17G, 17H:
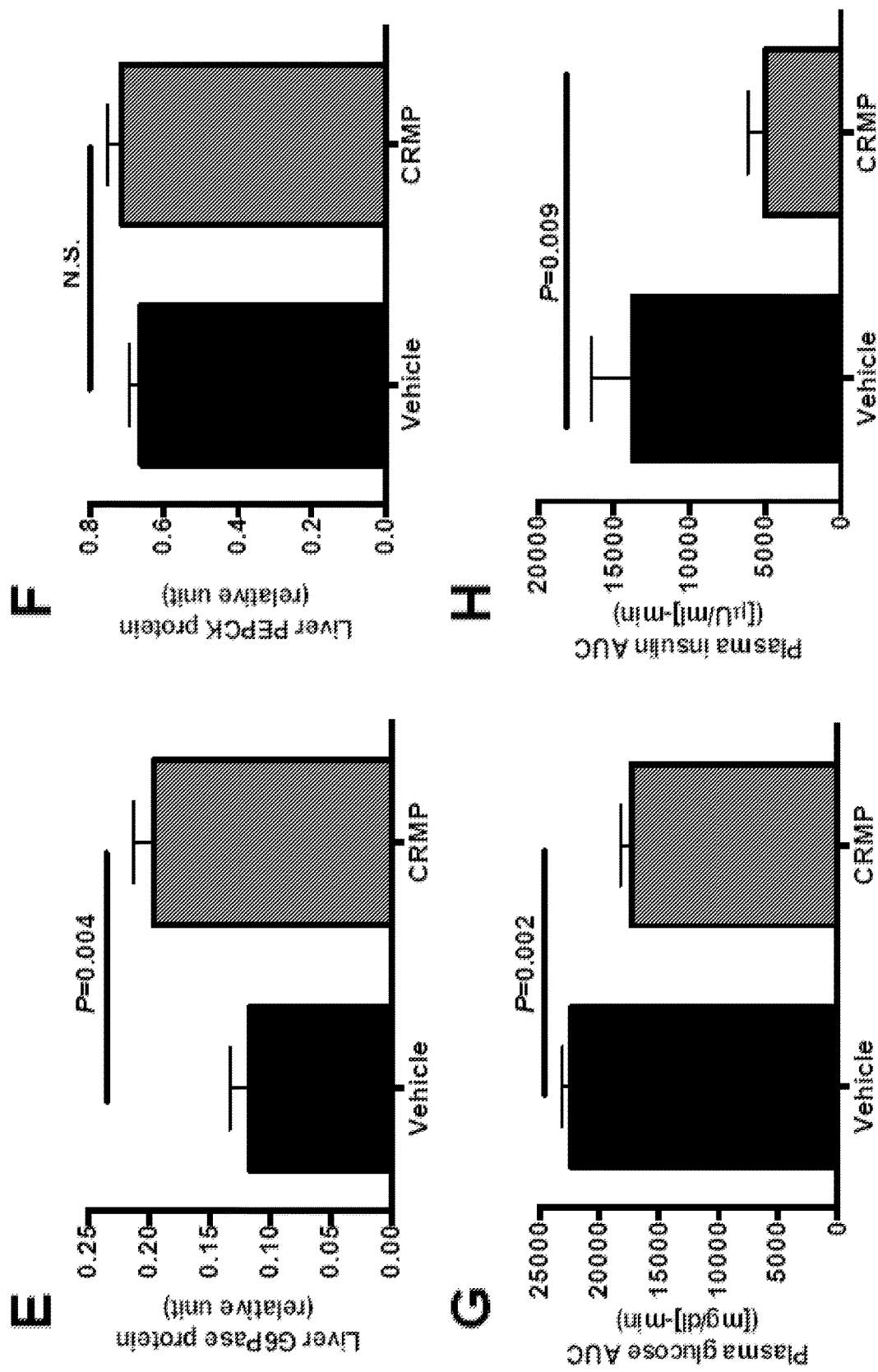
Figures 17I, 17J, 17K:
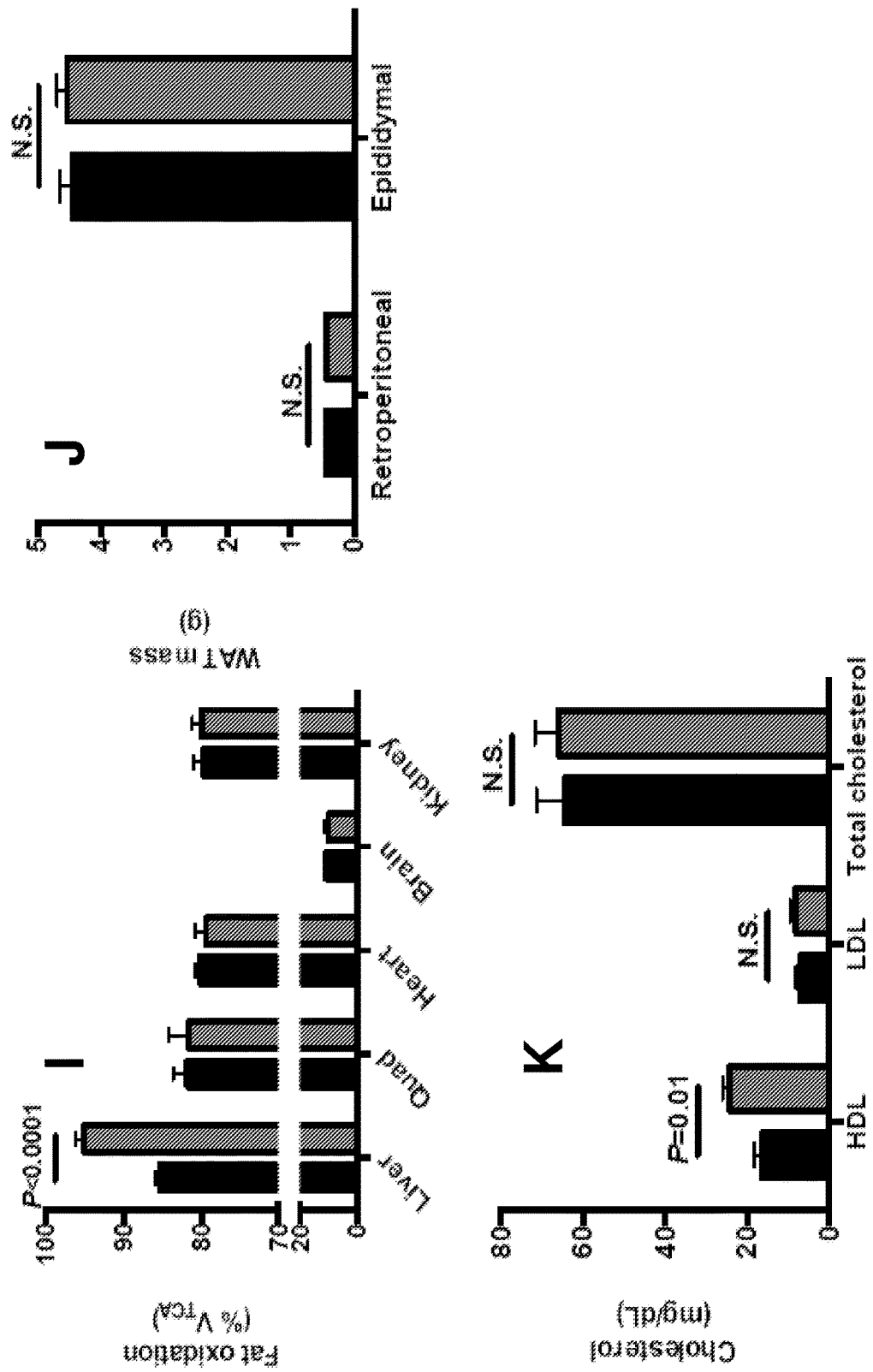

ERDNP Treatment Reduces Hepatic Pyruvate Carboxylase Flux and Increases Rates of Hepatic Mitochondrial Fat Oxidation The effects of ERDNP on rates of hepatic mitochondrial TCA ($V_{TCA}$) flux, $V_{PDH}$ flux, $V_{fa}$ flux and $V_{PC}$ flux were assessed using a novel combined NMR-LC/MS/MS method (Perry, et al., 2013, Cell. Metab. 18:740-8). Consistent with their reduced liver lipid content, liver TCA cycle flux was increased 60% in ERDNP-treated rats after one day of treatment. Furthermore this increase $V_{TCA}$ flux was entirely due to a 65-70% increase in rates of hepatic fat oxidation (FIG. 8E). In contrast, there were no differences in fat oxidation relative to $V_{TCA}$ in kidney, brain, heart, or skeletal muscle, indicating that the uncoupling effect of ERDNP is confined to the liver (FIG. 17I).

In one aspect, the lower skeletal muscle TAG content may be due, at least in part, to reduced hepatic very low-density lipoprotein (VLDL) export as a result of increased hepatic fatty acid oxidation. Liver VLDL export was reduced by 80% in ERDNP-treated animals (FIG. 8F).

Figures 18Q, 18R, 18S, 18T:
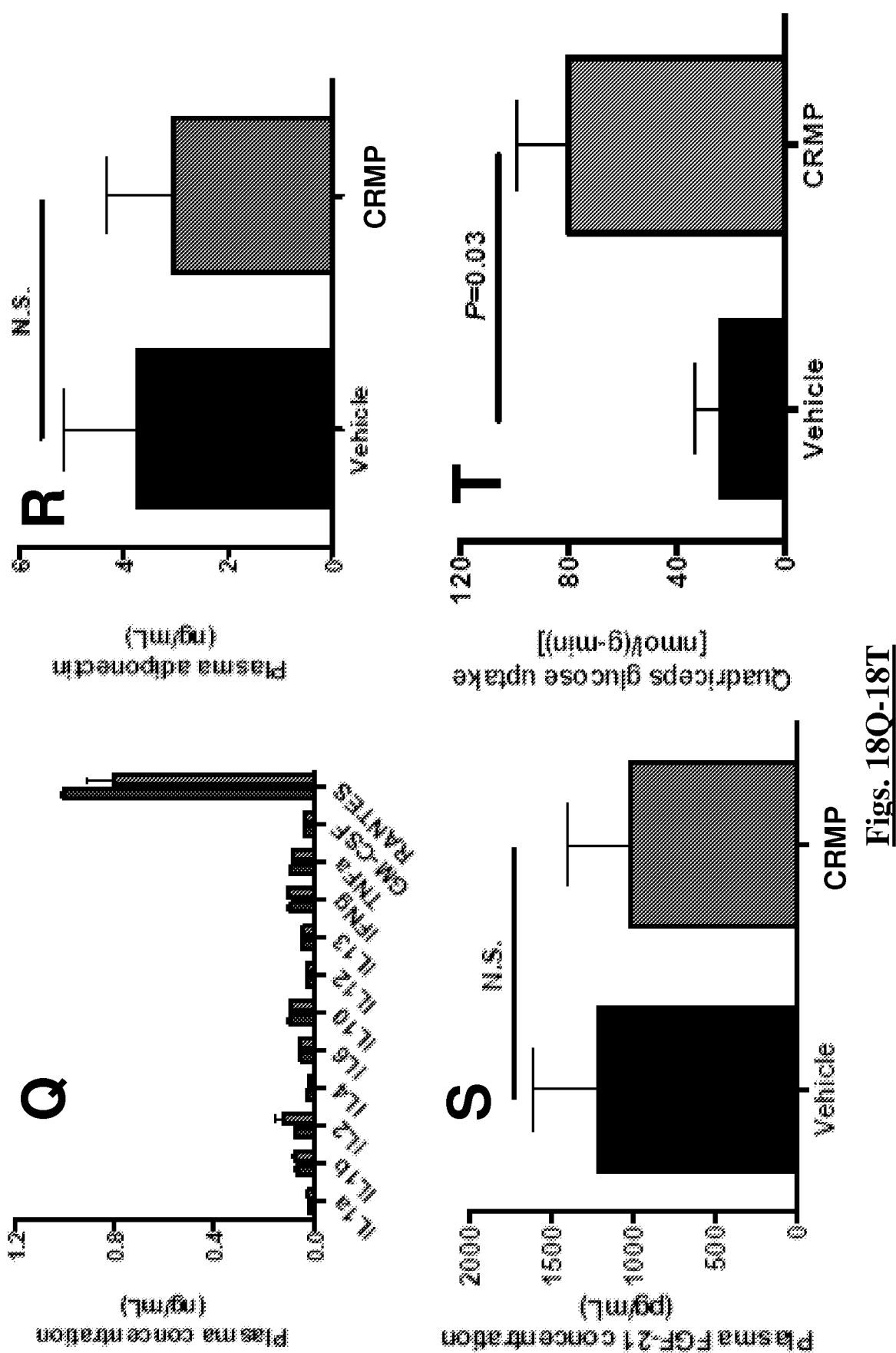
FIG. 18Q: Plasma inflammatory cytokine concentrations. n=3 per group.
FIGS. 18R-18S: Plasma adiponectin and FGF-21 concentrations.
FIG. 18T: Insulin-stimulated glucose uptake in quadriceps.
Figures 18U, 18V, 18W, 18X, 18Y:
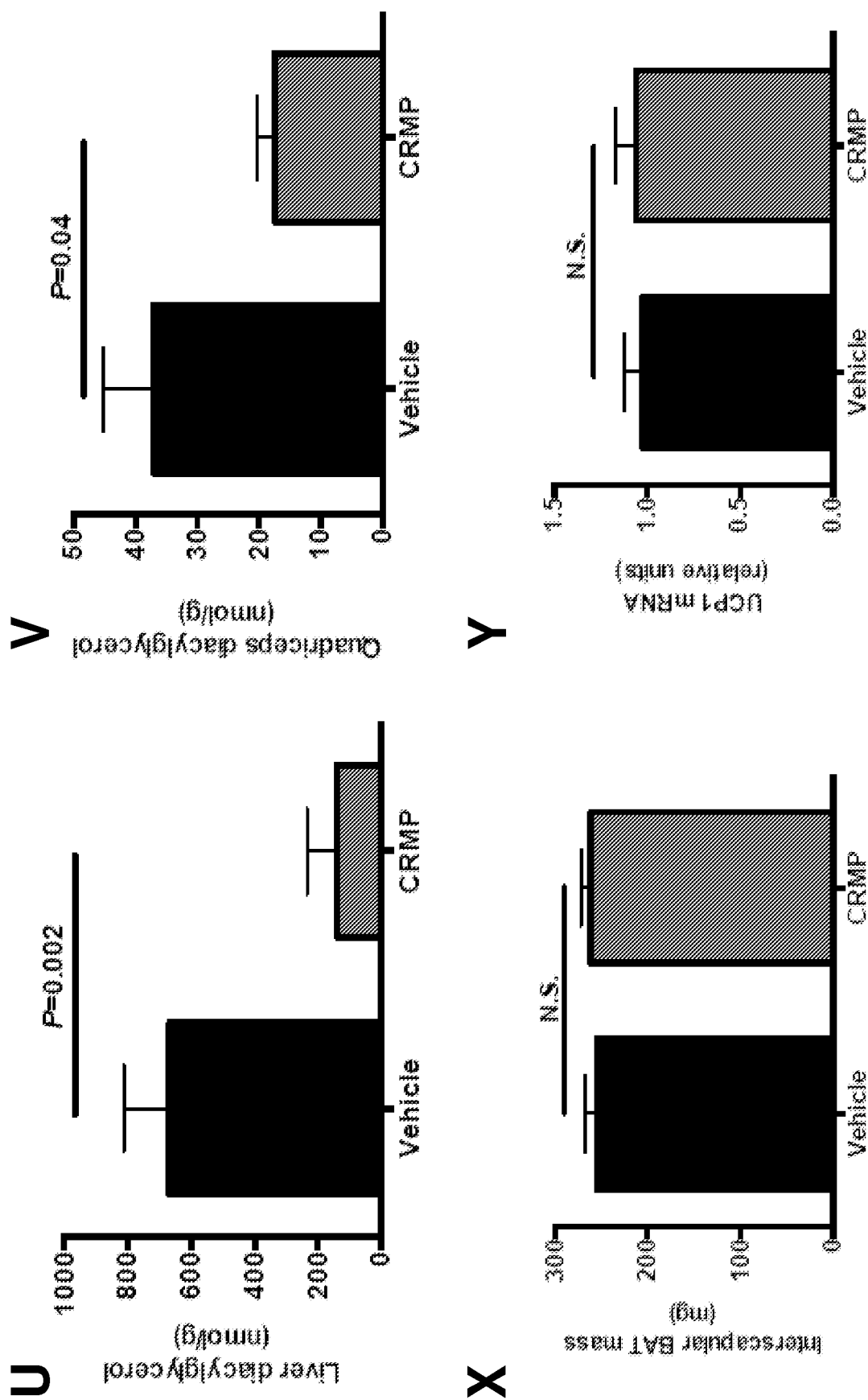
FIGS. 18U-18V: Liver and quadriceps DAG content.
FIG. 18X: Intrascapular brown adipose tissue mass.
FIG. 18Y: BAT UCP1 mRNA expression normalized to actin.
Figure 18Z:
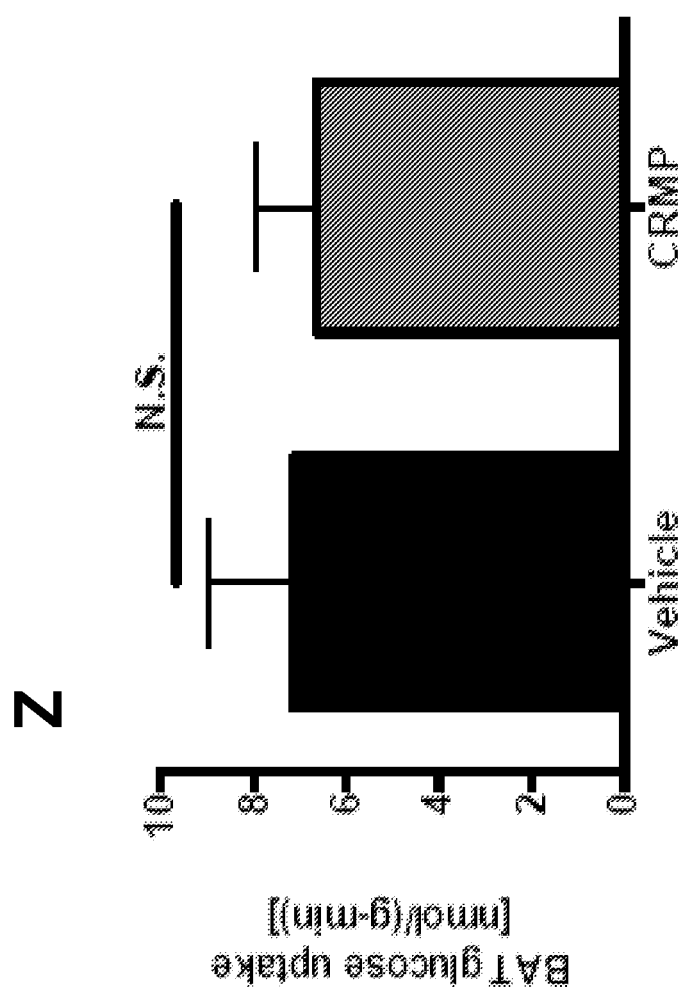

In contrast, no difference was observed in liver or quadriceps acylcarnitines and ceramides, liver glycogen content, plasma concentrations of twelve inflammatory markers, adiponectin, or FGF-21, thus dissociating these metabolites and adipocytokines from ERDNP-induced improvement in liver and muscle insulin responsiveness (FIGS. 18H-18S). In addition, there were no differences in brown adipose tissue mass, insulin-stimulated glucose uptake, or uncoupling protein-1 (UCP1) mRNA expression (FIGS. 18X-18Z).

To examine whether uncoupling with ERDNP reduces tissue lipid content and improves insulin sensitivity, a well-established high fat fed rat model of NAFLD and insulin resistance was treated with daily ERDNP (1 mg/kg) or vehicle for five days. Despite identical body weight and white adipose tissue content at the time of study, ERDNP treated rats were strikingly more insulin sensitive than their vehicle-treated counterparts, manifesting 30-40% reductions in fasting plasma glucose, fatty acid and triglyceride concentrations, a 30% increase in high density lipoprotein concentration and a 50% reduction in plasma insulin concentrations, without any difference in hepatic gluconeogenic protein expression (FIGS. 6A, 6C, 6G, 17A, 17C-17F, 17J-17K).

Example 7

ERDNP Improve Whole-Body Insulin Resistance

Rats treated with ERDNP manifested improved glucose tolerance, with lower plasma glucose and insulin concentrations throughout an intraperitoneal (IP) glucose tolerance test (FIGS. 6E-6F, 17I-17J). In order to more fully assess the effect of ERDNP on whole body insulin sensitivity, hyperinsulinemic-euglycemic clamps with radiolabeled glucose were performed to assess insulin action in liver and skeletal muscle (FIGS. 18A-18B). Consistent with improved whole body insulin sensitivity, the ERDNP-treated rats required two-fold more glucose to maintain euglycemia during the hyperinsulinemic-euglycemic clamp study (FIGS. 7A, 18C). Without wishing to be limited by any theory, this improvement in insulin-stimulated whole body glucose metabolism in the ERDNP-treated animals can be attributed to increases in both liver and muscle insulin sensitivity, as reflected by a 2.5-fold increase in insulin-stimulated peripheral muscle glucose uptake and a 3-fold greater suppression of hepatic glucose production in ERDNP-treated rats during the hyperinsulinemic-euglycemic clamp (FIGS. 7C, 18T). There is a strong causal relationship between ectopic diacylglycerol (DAG) accumulation and insulin resistance in liver and skeletal muscle. ERDNP-treated rats had lower triacylglycerol (TAG) and DAG content and decreased protein kinase Cε (PKCε) and PKCθ translocation in liver and skeletal muscle respectively (FIGS. 8A-8B, 18D-18F, 18U-18V). The reduction in skeletal muscle triglycerides were associated with 40% lower plasma triglyceride concentrations and an 80% reduction in liver very low-density lipoprotein (VLDL) export (FIG. 6B, 8F), explaining the reduced muscle lipid content as a result of liver-specific uncoupling.

The data presented herein indicates absence of hyperthermia in the rats and stand in contrast to the reduced UCP1 mRNA expression in mice treated with a far higher dose of DNP in drinking water (~89 mg/[kg-day]), emphasizing the safety of the present formulation. ERDNP was similarly effective at preventing the development of NAFLD: rats fed high fat diet for 2 weeks and concurrently fed ERDNP had lower fasting plasma glucose, NEFA and insulin concentrations associated with 50-90% reductions in triglyceride concentrations in liver, plasma, and skeletal muscle (FIGS. 22A-22F). In order to more conclusively examine the effect of ERDNP treatment on whole-body energy metabolism, Comprehensive Lab Animal Monitoring System (CLAMS) metabolic cage studies were performed in mice fed ERDNP or vehicle and no difference was observed in any parameter examined (FIGS. 23A-23H). These data again show that very low levels of uncoupling confined to the liver, which cannot be measured with the relatively insensitive CLAMS studies, are sufficient to reduce liver fat content and improve whole-body insulin resistance, without affecting food intake, behavior, or whole-body energy expenditure.

Example 8

ERDNP Treatment Reverses Diabetes in Zucker Diabetic Fatty Rats

Since ERDNP treatment safely reversed NAFLD, hypertriglyceridemia, and hepatic and peripheral insulin resistance in high fat fed rats. In certain embodiments, ERDNP could reverse hyperglycemia, hypertriglyceridemia and hepartic steatosis in a well-established obese rat model of T2D, the Zucker Diabetic Fatty (ZDF) rat (a hyperphagic leptin-deficient obese rat model).

Figures 9A, 9B, 9C, 9D:
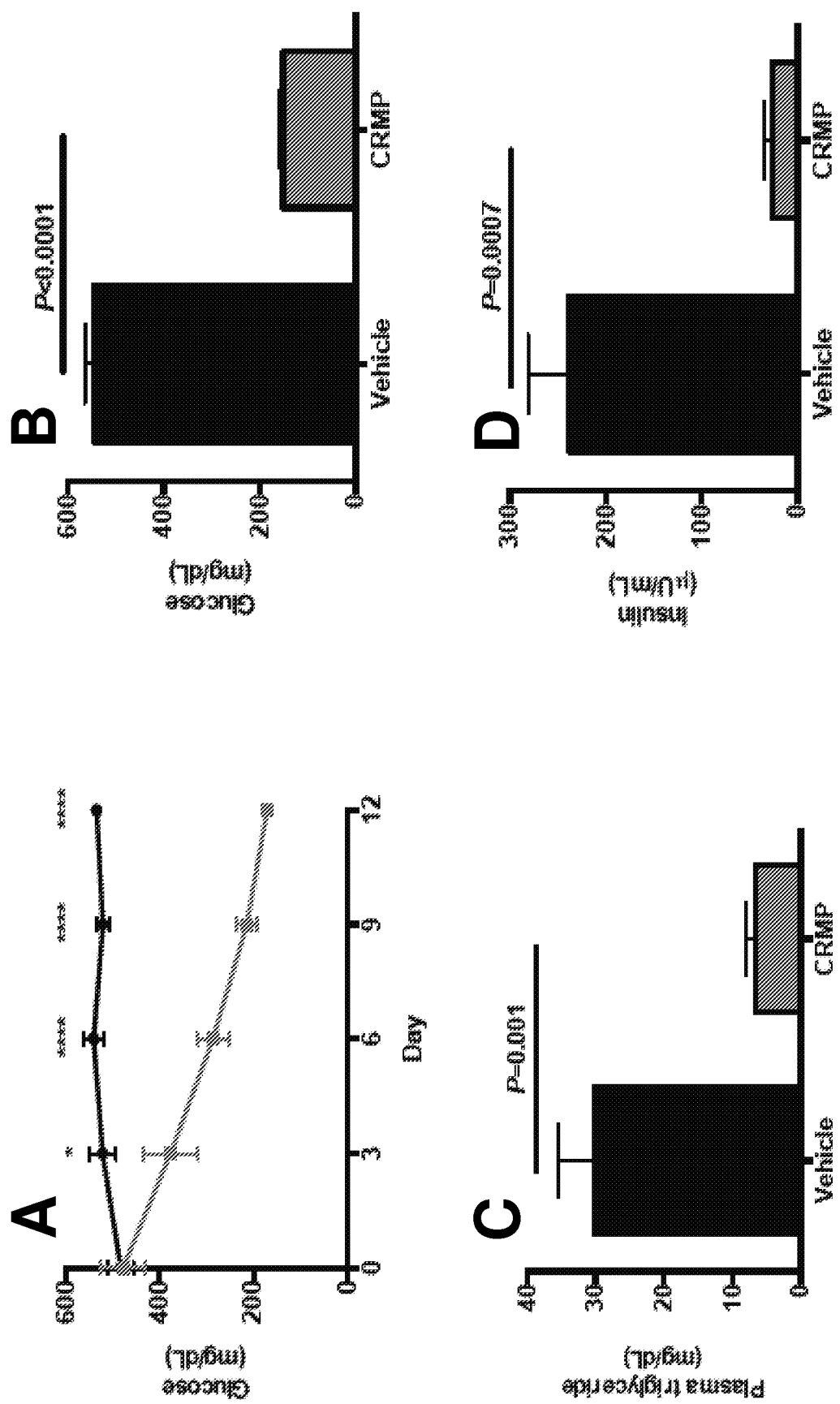
FIGS. 9A-9H, illustrates the finding that oral ERDNP (1 mg/kg per day for 14 days) reverses NAFLD and improves glucose tolerance in Zucker Diabetic Fatty rats.
Figures 9E, 9F, 9G, 9H:
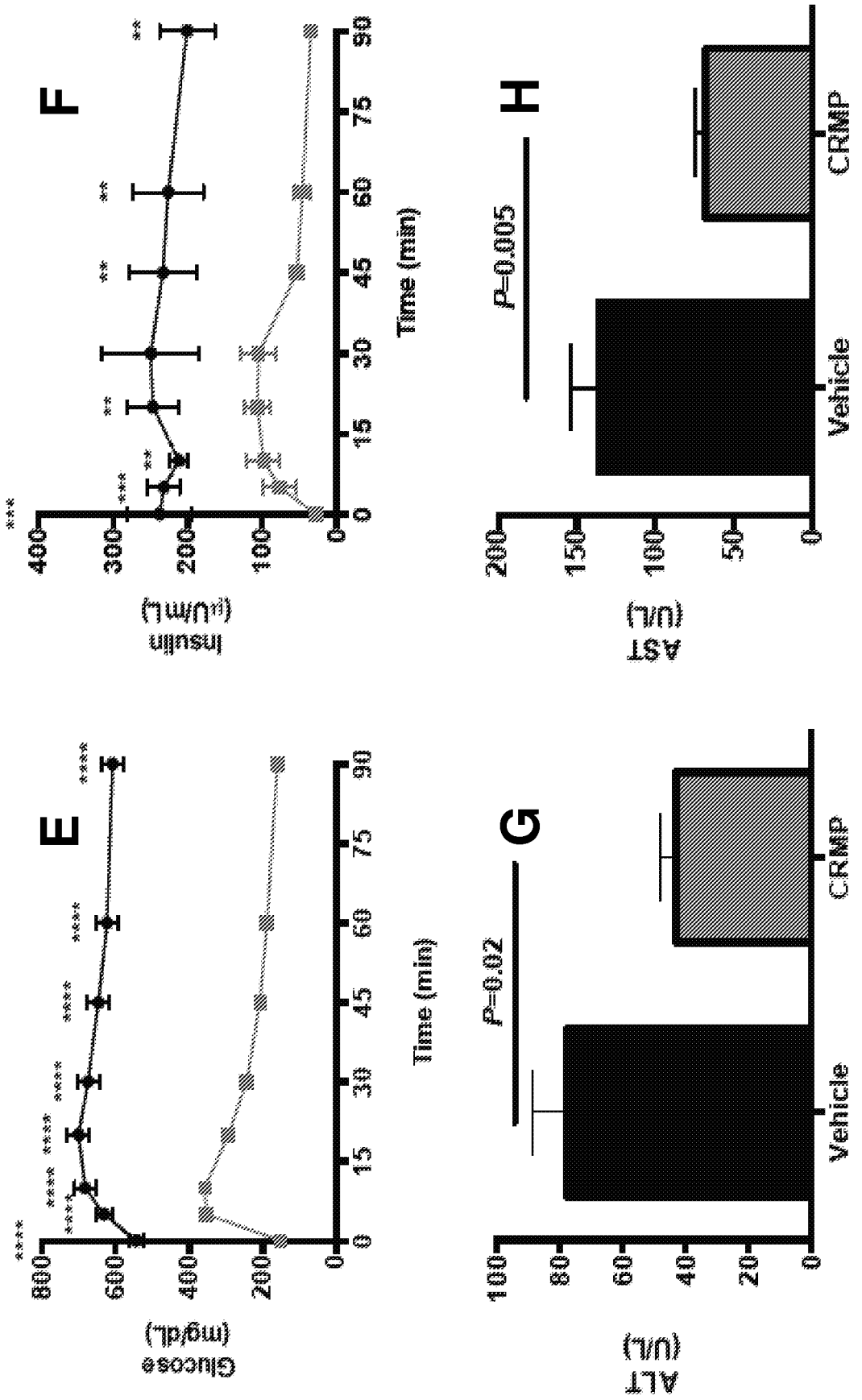
Figures 19A, 19B, 19C, 19D:
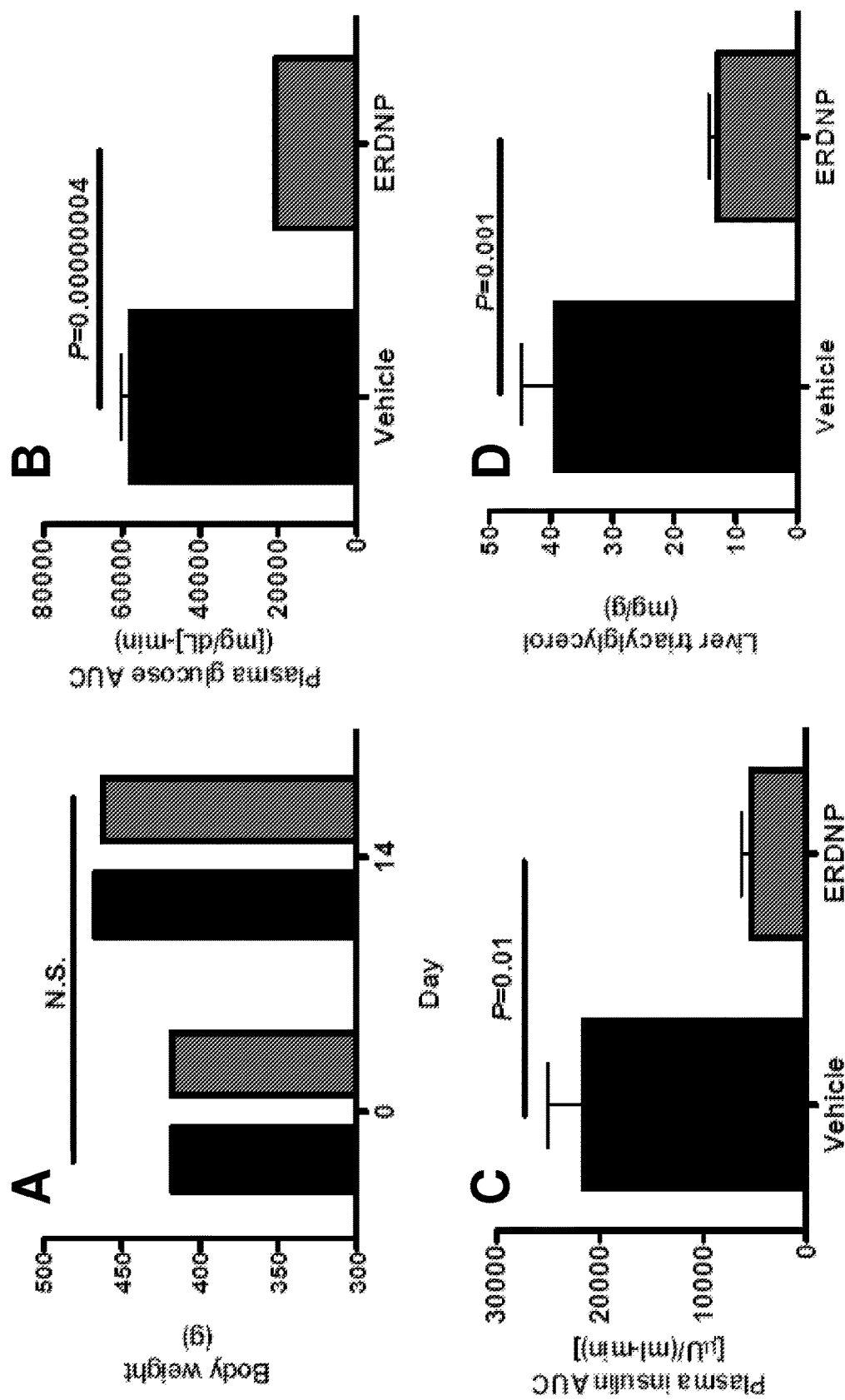
FIGS. 19A-19L, illustrates the finding that ERDNP (1 mg/kg per day for 14 days) reverses NAFLD and improves glucose tolerance in Zucker Diabetic Fatty rats.
Figures 19E, 19F, 19G, 19H:
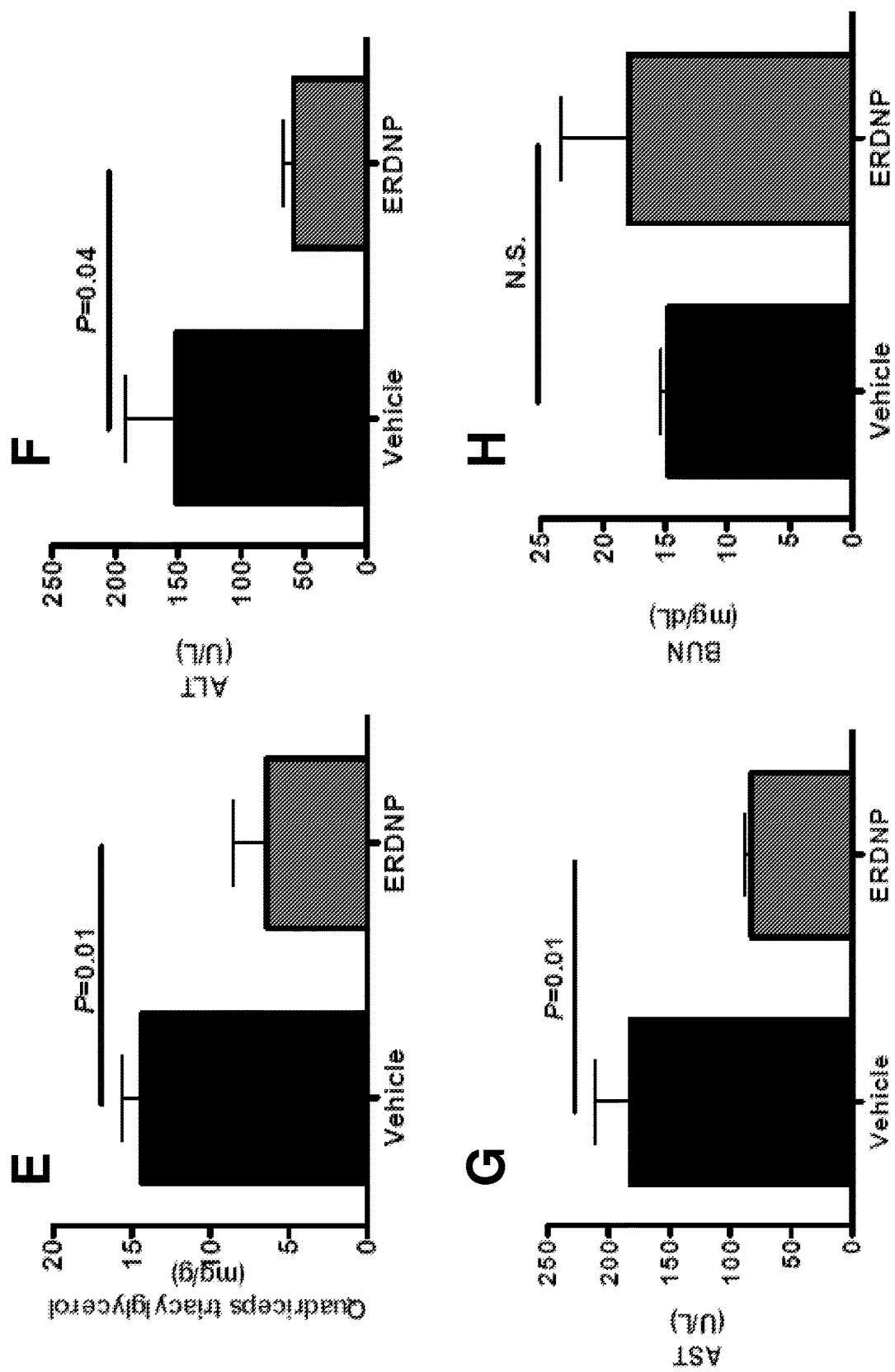
Figures 19I, 19J, 19K, 19L:
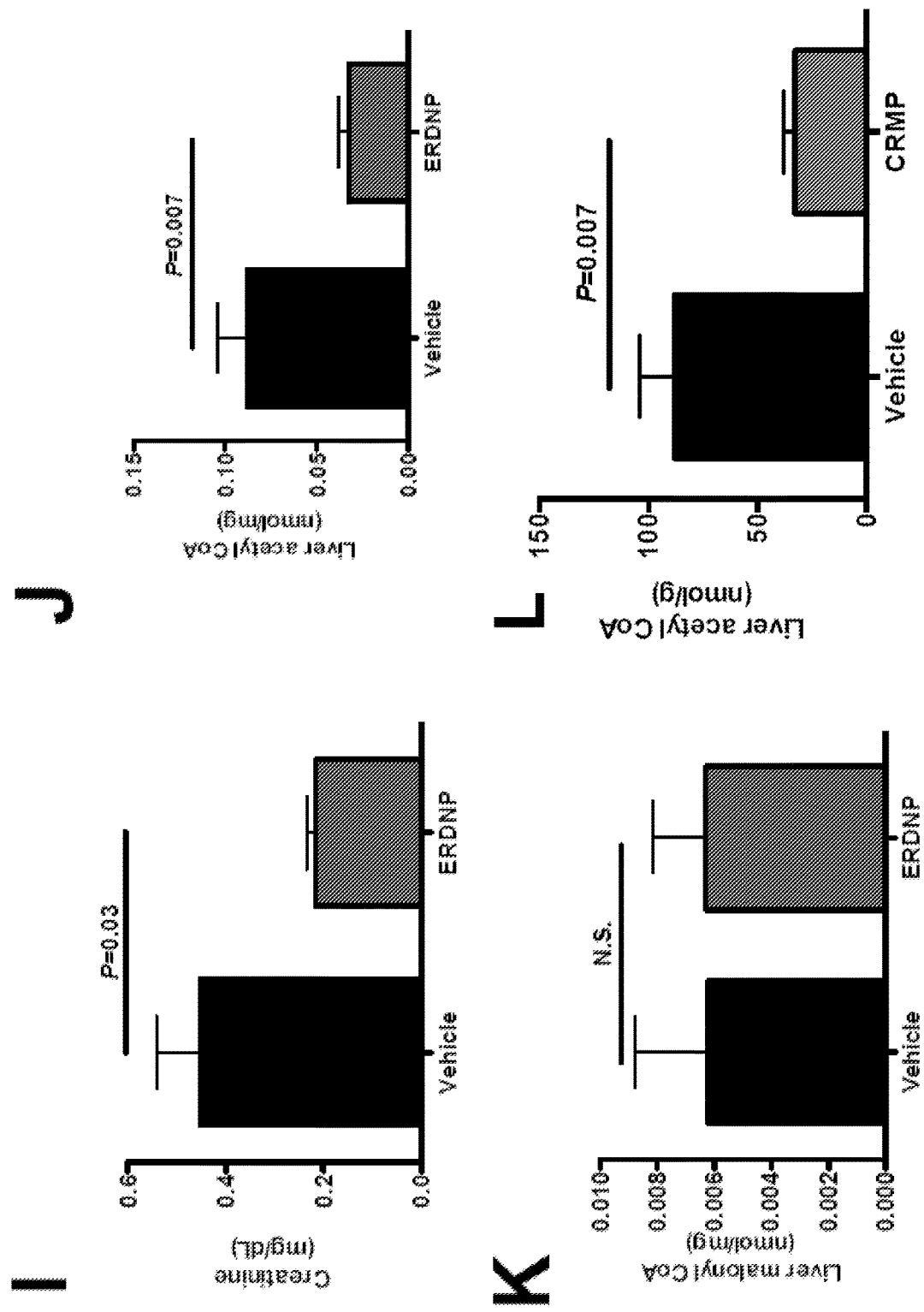

To this end, high fat fed ZDF rats were treated with ERDNP (1 mg/kg) daily for 14 days. ERDNP treatment was associated with a progressive reduction in plasma glucose concentrations and a 400 mg/dL decrease in fasting plasma glucose concentrations after two weeks of treatment along with an 80% decrease in fasting plasma insulin concentrations despite identical body weight before and after treatment (FIGS. 9A-9B, 19A). Consistent with improved insulin sensitivity, ZDF rats also had lower fasting plasma triglyceride concentrations after 14 days of ERDNP treatment (FIGS. 8C-8D). ERDNP-treated rats also displayed a 60% reduction in hepatic acetyl CoA content, which IS a key regulator of gluconeogenesis and glycemia in diabetic animals (FIG. 19L).

Figure 9I:
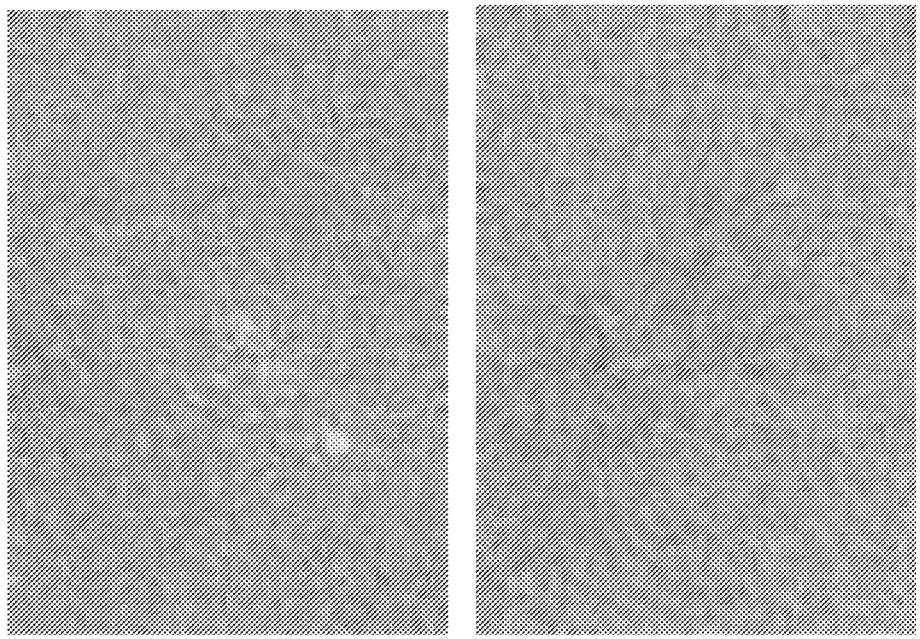
FIG. 9I: Liver histology (hematoxylin & eosin stain). In all panels, *P<0.05, P<0.01, *P<0.001, ****P<0.0001. n=6-7 per group.
Figure 10:
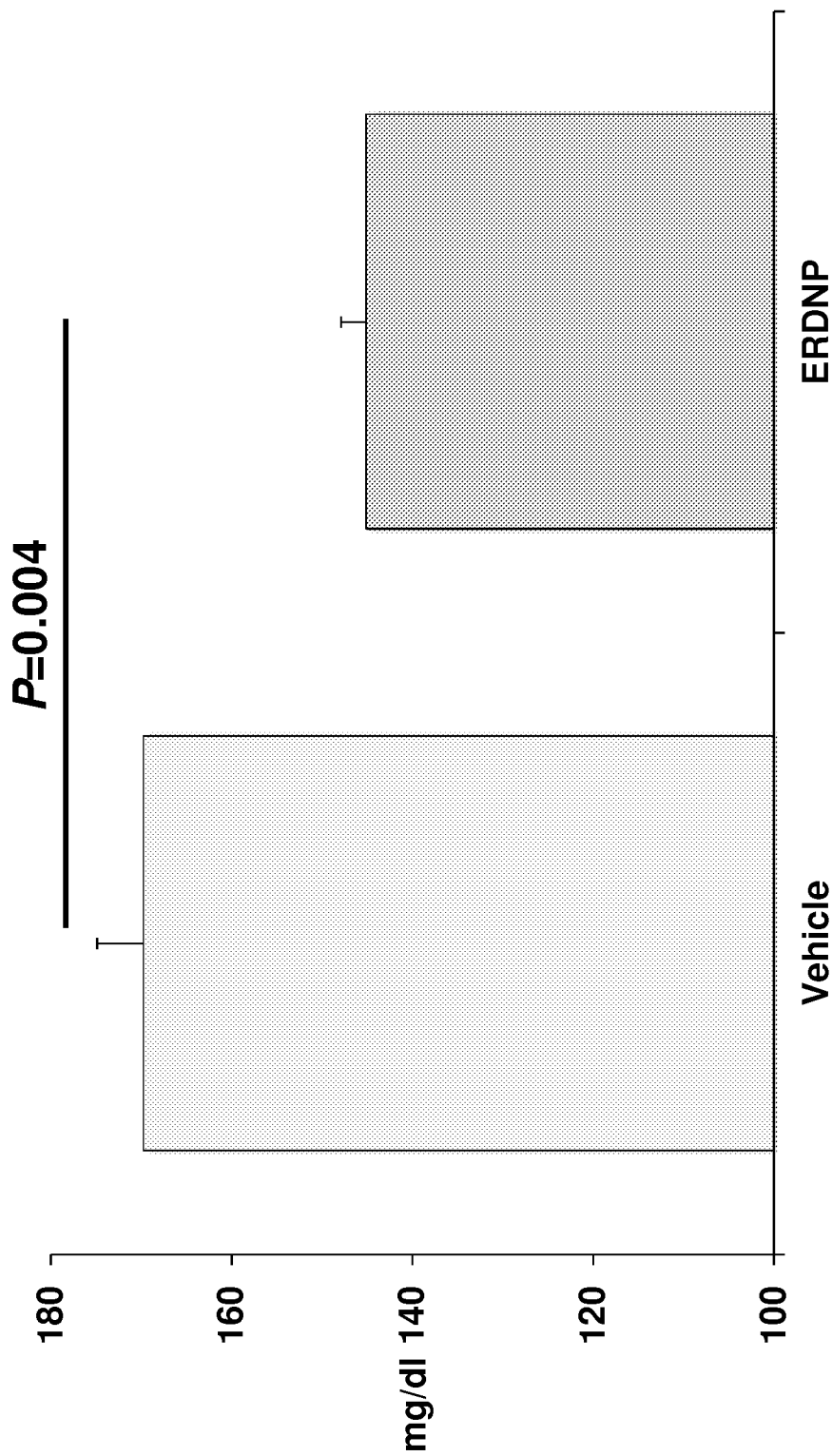
FIG. 10 is a graph illustrating fasting plasma glucose. Rats were fasted for 6 hours. ERDNP oral dosing (1 mg/kg every 12 hours) for 5 days results in significant reductions in fasting plasma glucose concentrations in a high fat fed rat model of insulin resistance and NAFLD.
Figures 11A, 11B:
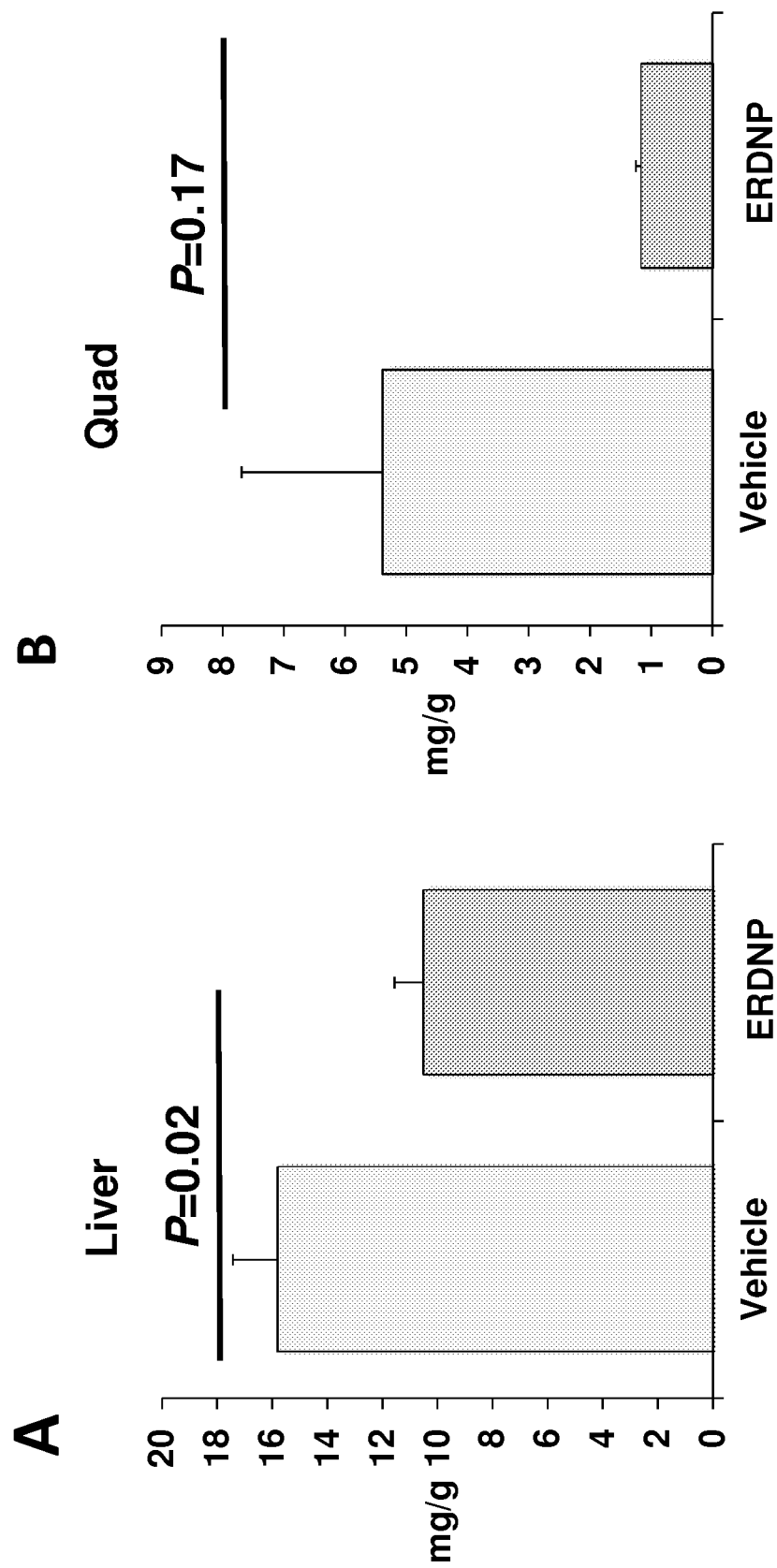
FIGS. 11A-11B, illustrates tissue TAG content after treatment with vehicle or ERDNP.
Figure 12:
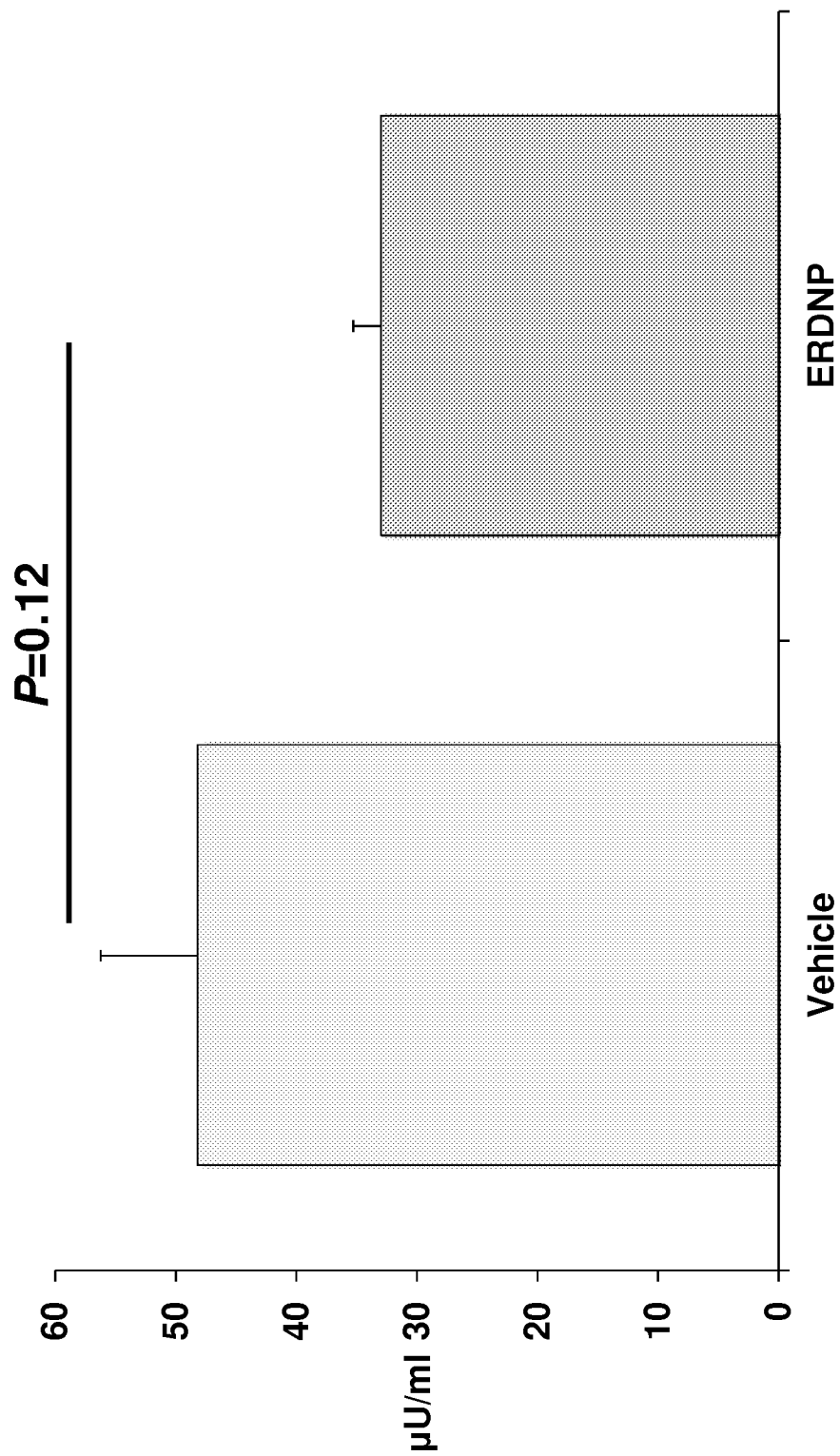
FIG. 12 is a graph illustrating how single day dosing of extended release DNP (ERDNP) for 5 days shows a strong tendency to reduce plasma insulin concentrations. Rats were treated once daily with 1 mg/kg ERDNP or vehicle for 5 days. Prior to sacrifice, rats were fasted for 6 hours.
Figure 13:
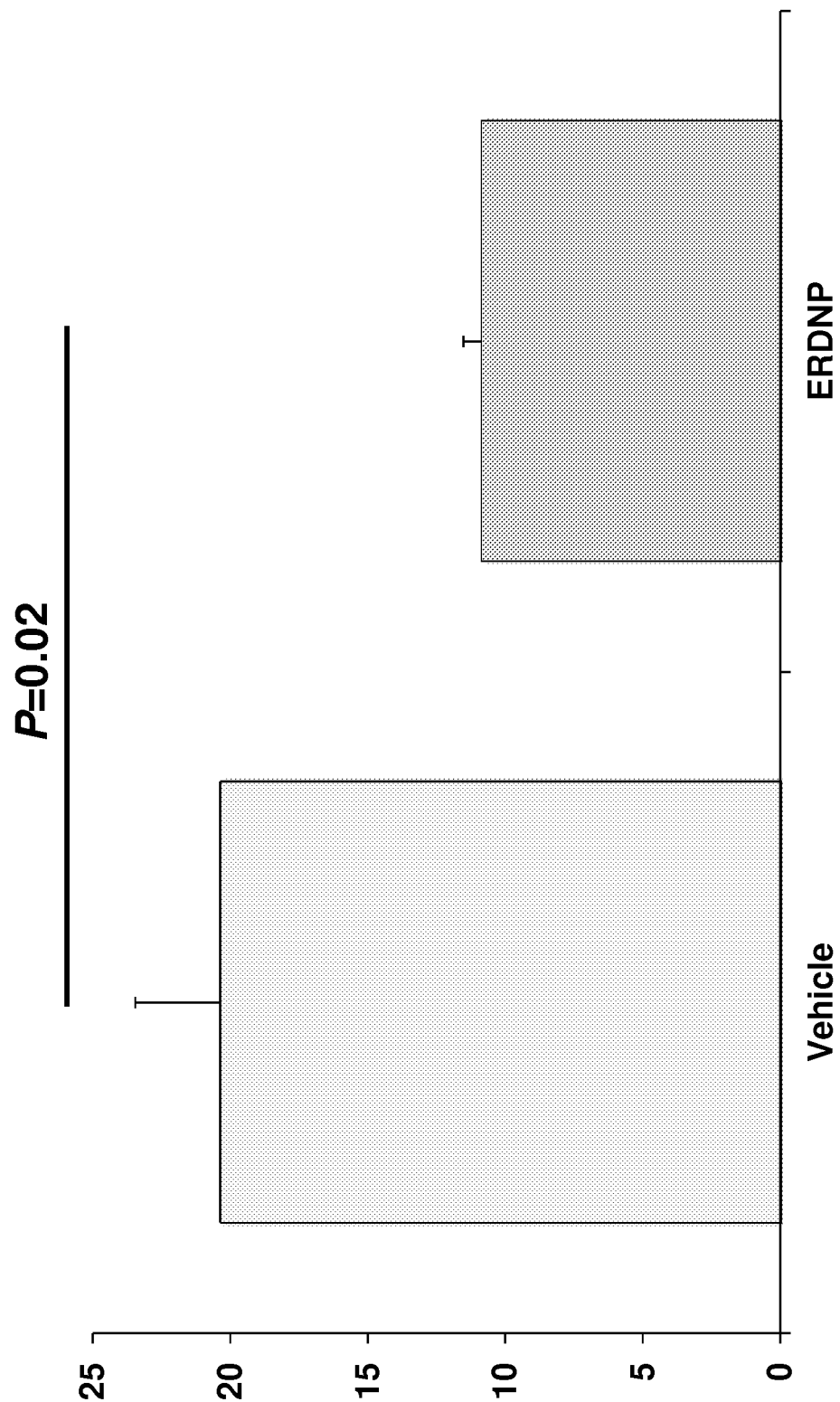
FIG. 13 is a graph illustrating how single day dosing of extended release DNP (ERDNP) for 5 days results in significant reductions in HOMA-IR. This reduction in HOMA-IR demonstrated that single day dosing of ERDNP reduced whole body insulin resistance in a high fat rodent model of insulin resistance.
Figures 14E, 14F, 14G, 14H:
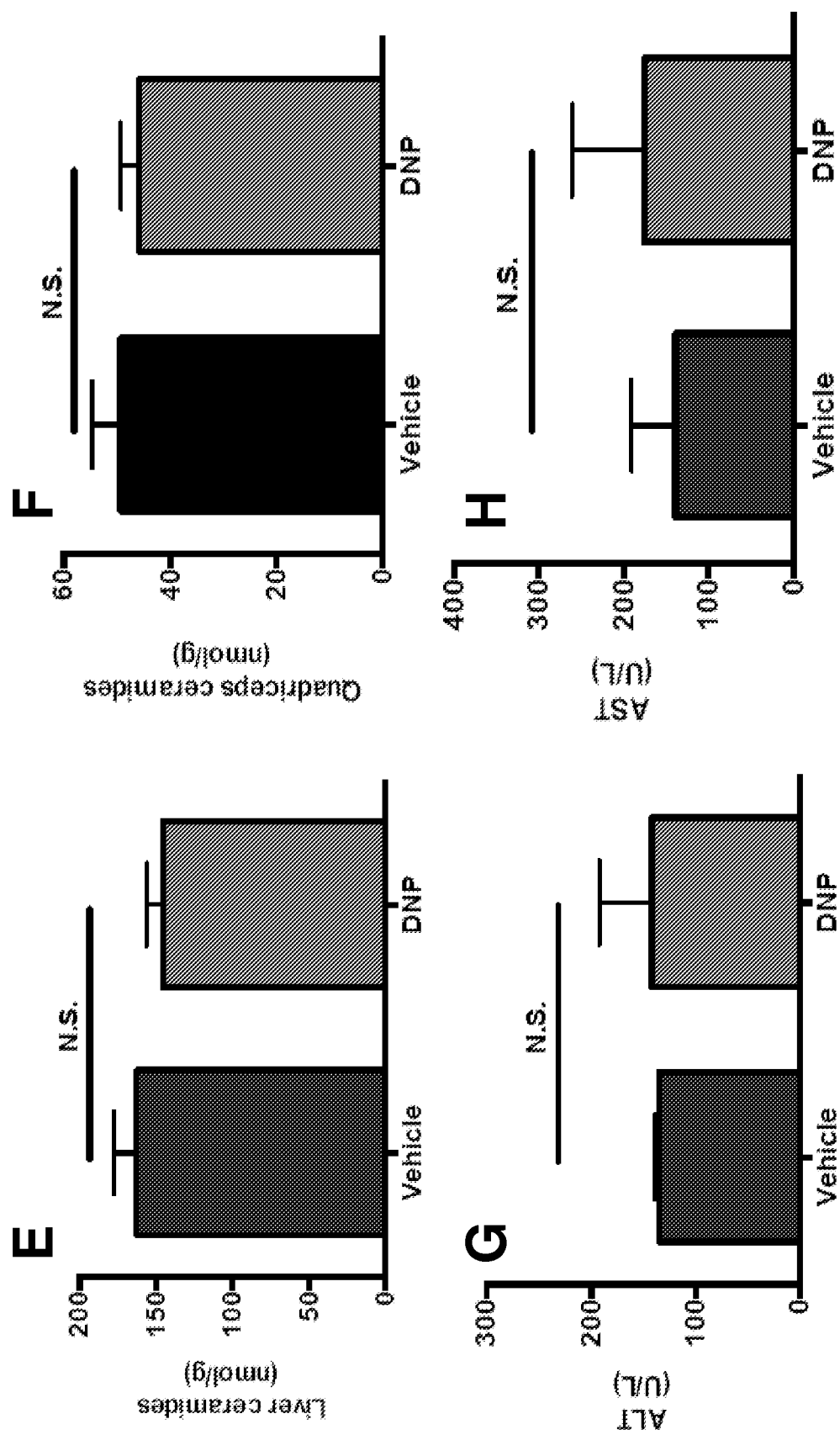
Figures 14I, 14J, 14K, 14L:
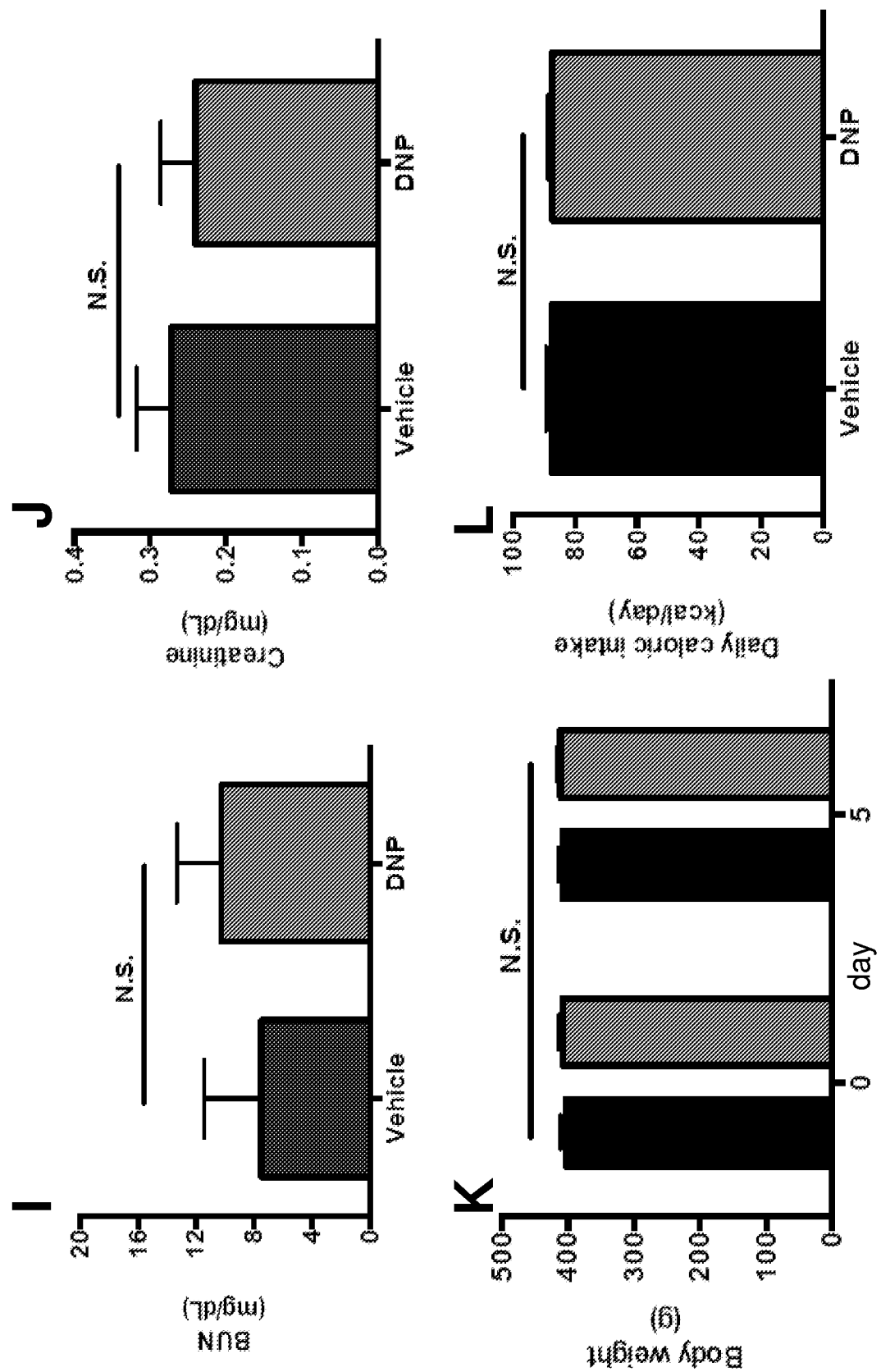
Figures 15A, 15B, 15C, 15D:
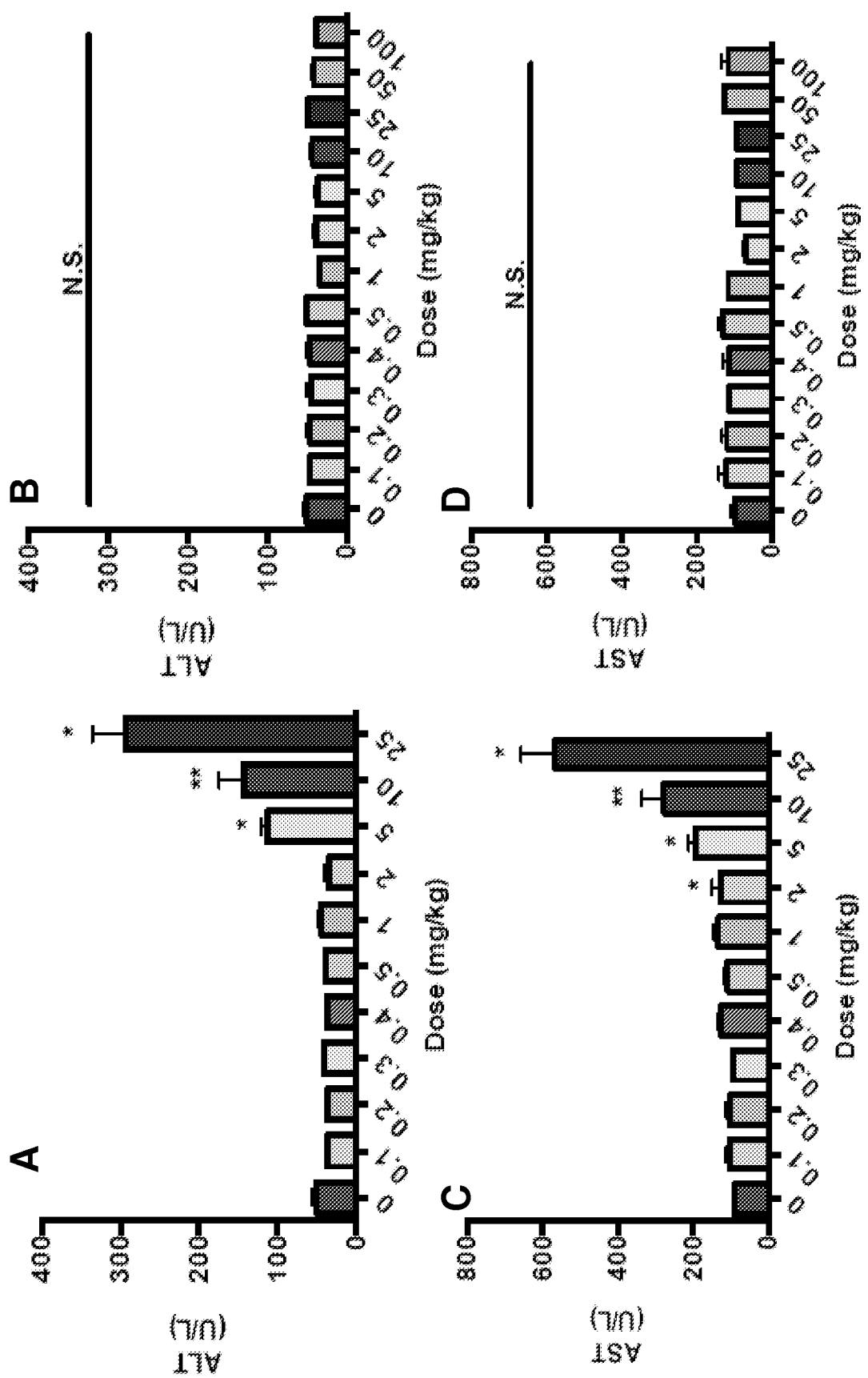
FIGS. 15A-15H, illustrates the finding that ERDNP has a 500-fold wider ratio of effective to safe dose than DNP.
Figures 15E, 15F, 15G, 15H:
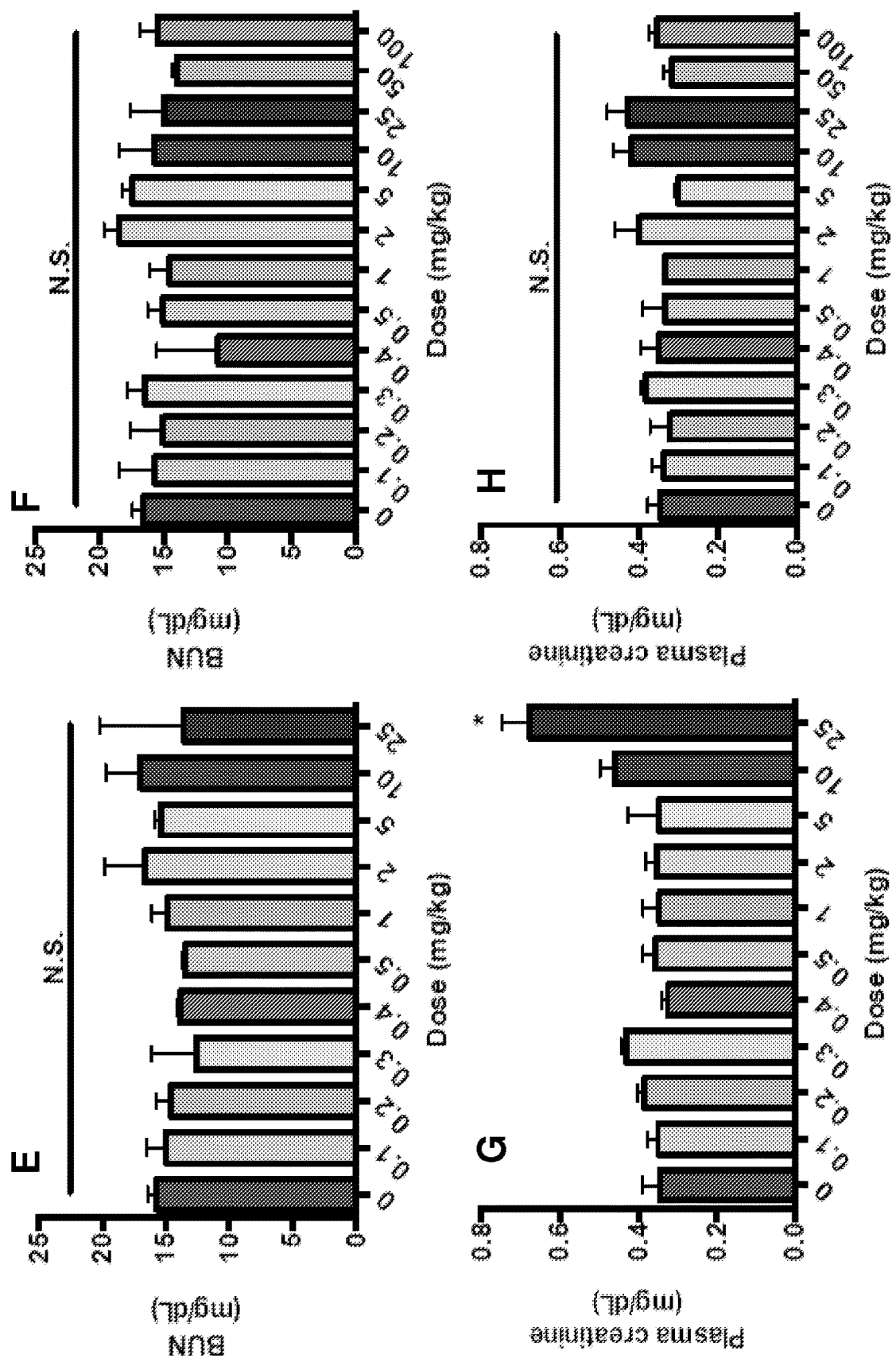
Figures 16A, 16B, 16C, 16D:
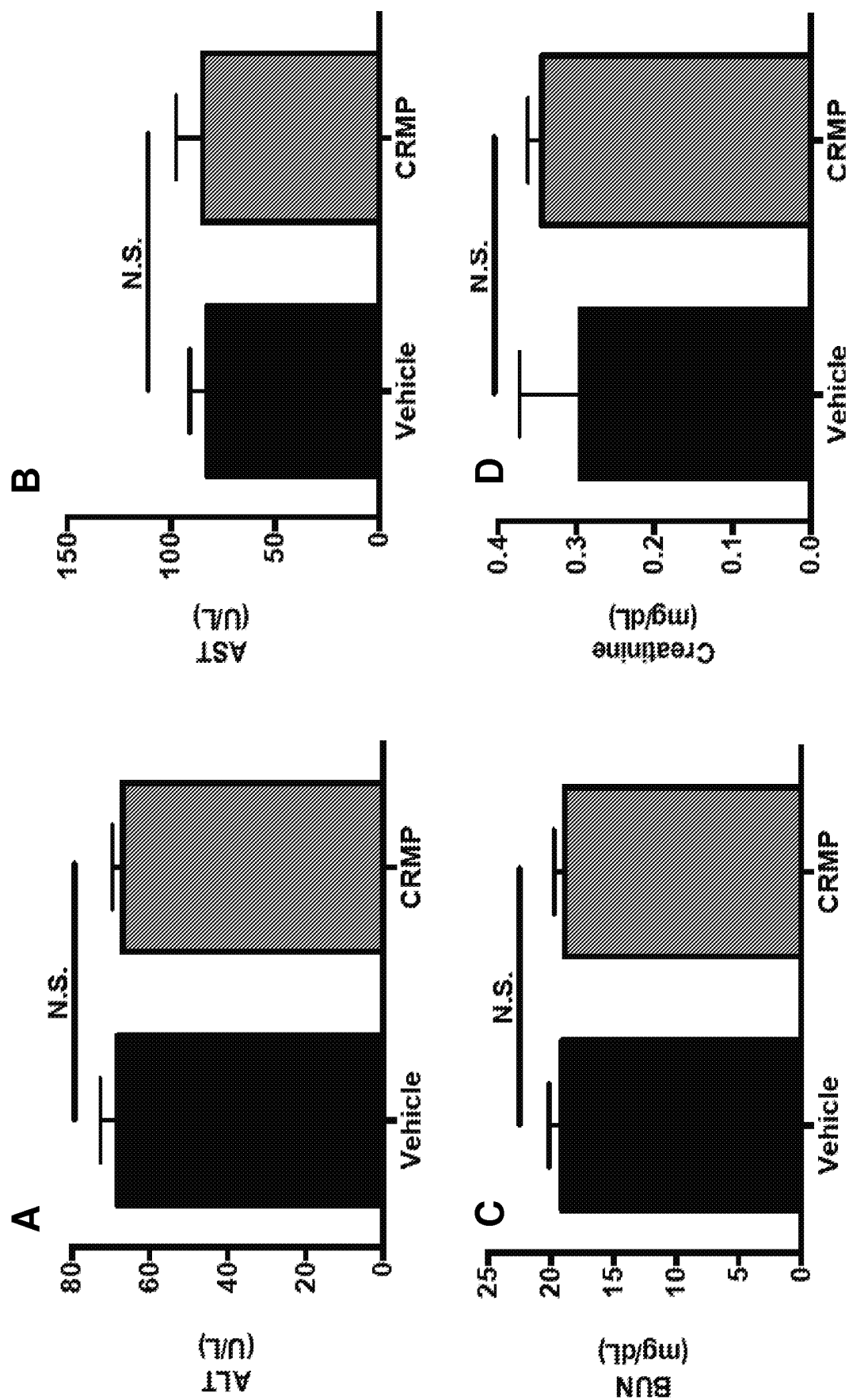

ERDNP-treated rats manifested improved glucose tolerance during the intraperitoneal glucose tolerance test, with 50-80% reductions in plasma glucose and insulin concentrations at each time point during the GTT, and 60-70% reductions in total glucose and insulin area under the curve in the ERDNP-treated group (FIGS. 9E-9F, 19B-19C). These improvements in insulin sensitivity and glucose tolerance were associated with 65% and 55% reductions in liver and quadriceps TAG concentration, respectively (FIGS. 19D-19E). There was no detectable renal toxicity with this two-week treatment as reflected by no changes in plasma BUN, and a modest reduction in creatinine concentrations (FIGS. 19F-19I). In contrast, liver enzymes (AST, ALT) and hepatic TAG content were increased in ZDF rats before treatment reflecting hepatic steatosis associated with liver inflammation in these poorly controlled diabetic animals; ERDNP treatment normalized these parameters reflecting reversal of hepatic steatosis and liver inflammation in this rat model of NASH and T2D with ERDNP treatment (FIGS. 19F-19I). Histologic analysis confirmed the resolution of NAFLD with ERDNP treatment in this poorly controlled diabetic model (FIG. 9I), highlighting the possibility that ERDNP is a therapeutic agent for NAFLD-associated liver disease.

Example 9

ERDNP Treats NAFLD-Induced NASH

Figure 20E:
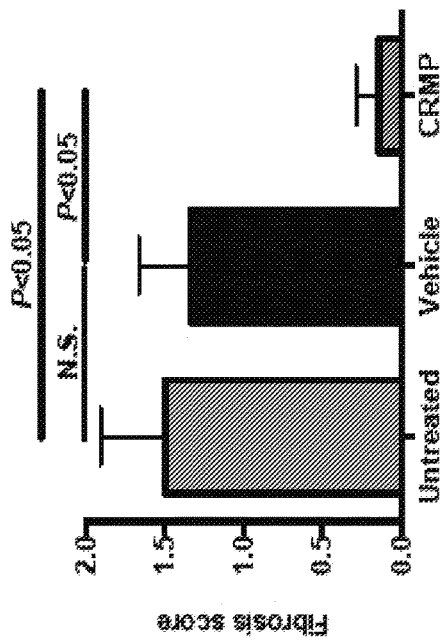
Figure 20F:
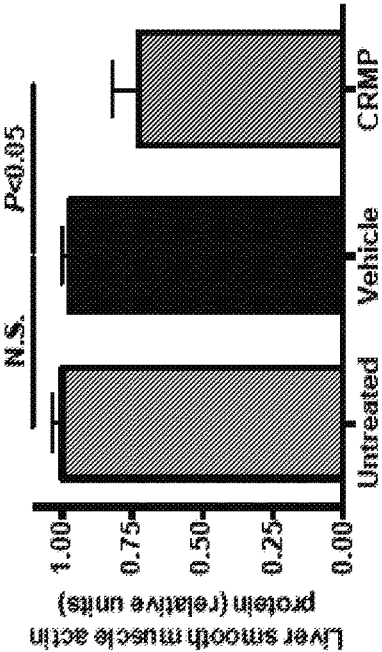
Figure 20G:
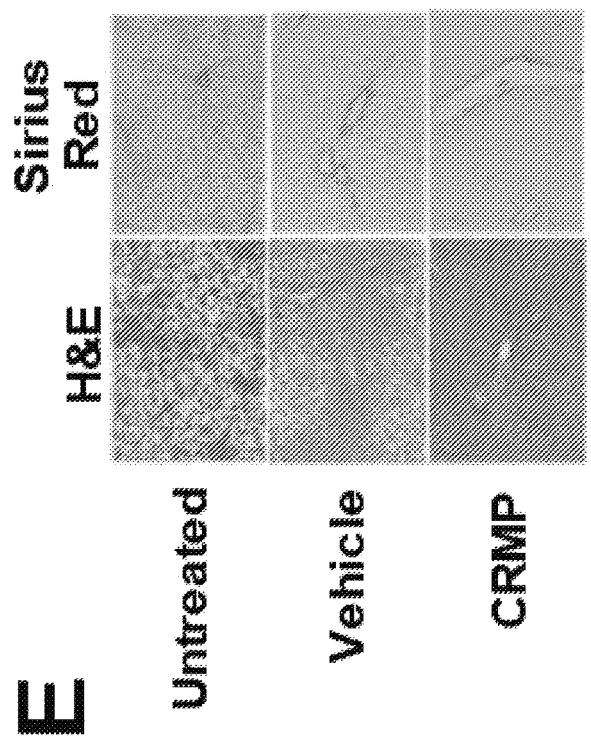
Figure 20H:
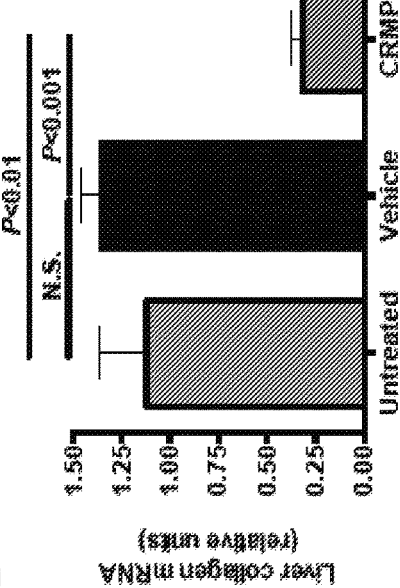
Figures 24A, 24B:
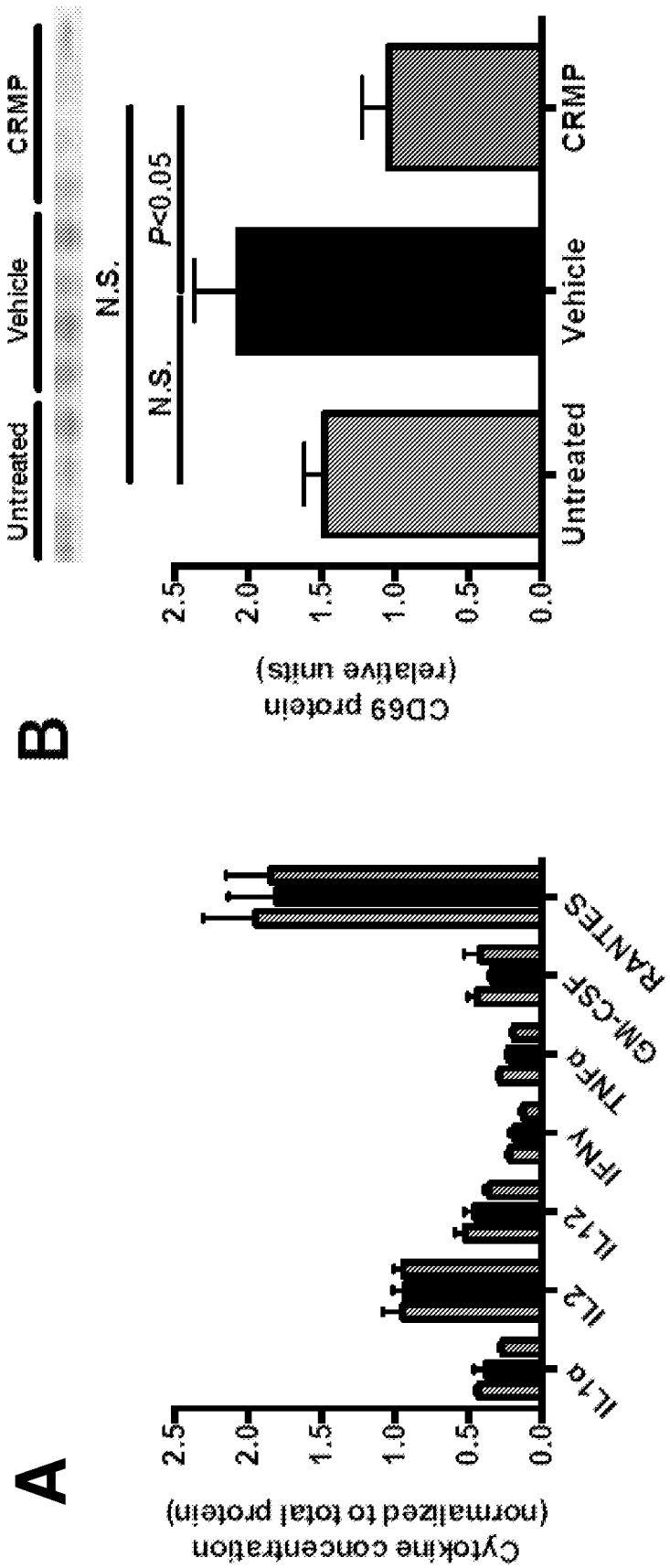

To investigate the possibility that ERDNP ameliorates or treats NAFLD-induced NASH, rats were fed a methionine/ choline deficient diet (MCD) for 8 weeks to induce NASH. Six weeks of ERDNP treatment reduced liver triglyceride concentrations by 90% and normalized plasma transaminase concentrations (FIGS. 20A-20C). Consistent with the reduction in liver inflammation indicated by the normalization of transaminase concentrations, ERDNP treated rats displayed lower concentrations of five inflammatory cytokines in the liver and reduced liver CD69 protein, a marker of activated T cells, in ERDNP treated rats relative to control rats (FIGS. 20D, 24A-24B). Histological analysis confirmed the resolution of NAFLD and liver fibrosis in ERDNP treated rat livers, with a 90% reduction in the liver fibrosis score and accompanying reductions in collagen mRNA, smooth muscle actin protein, and hydroxyproline concentrations (FIGS. 20E-20I). Rats treated with ERDNP also exhibited reductions in apoptosis, with lower caspase 3 and caspase 9 protein expression, but no detectable difference in TUNEL staining (FIGS. 20J-20K, 24C). Patients with hepatic cirrhosis manifest reduced postprandial hepatic glycogen synthesis, and thus hepatic glycogen content was measured in MCD fed rat livers. An 80% increase in hepatic glycogen synthesis was observed in ERDNP-treated rats associated with reversal of fasting hypoglycemia in these animals (FIG. 24D-24E). ERDNP improved liver synthetic function, as indicated by 20% increases in plasma albumin concentrations (FIG. 20L). These data demonstrate improvements in hepatic protein and carbohydrate synthetic function, in addition to reversal of liver fibrosis, in a NASH model and emphasize the efficacy of ERDNP as a therapeutic agent for NAFLD-associated NASH to prevent liver cirrhosis and potentially hepatocellular carcinoma.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a disease or disorder in a subject in need thereof, the method comprising orally administering to the subject a therapeutically effective amount of a pharmaceutical composition comprising:
   at least one pharmaceutically acceptable carrier and a therapeutically effective amount of 2,4-dinitrophenol (DNP) or a salt or solvate thereof;
   wherein the DNP or a salt or solvate thereof, is coated with an extended release coating comprising:
   i) at least one water soluble polymer; and
   ii) at least one water insoluble polymer,
   wherein the therapeutically effective amount of DNP is about 1 to about 10 mg/kg/day or about 1 to about 200 mg;
   wherein administration of the composition to a subject provides a steady state plasma concentration of DNP ranging from about 0.05 µM to about 200 µM in the subject, and wherein the composition does not cause significant systemic toxicity or significant increase in body temperature in the subject and,
   wherein the disease or disorder is at least one selected from the group consisting of nonalcoholic fatty liver disease (NAFLD), non-alcoholic steatohepatitis (NASH), hepatic steatosis, type 2 diabetes (T2D), acquired lipodystrophy, inherited lipodystrophy, partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma,
   whereby the disease or disorder in the subject is treated in the subject.

2. The method of claim 1, wherein the therapeutically effective dose of the DNP ranges from about 1 mg/kg/day to about 10 mg/kg/day.

3. The method of claim 1, wherein administration of the composition provides a steady state plasma concentration of the DNP ranging from about 0.5 µM to about 50 µM in the subject.

4. The method of claim 3, wherein administration of the composition provides a steady state plasma concentration of the DNP ranging from about 3 µM to about 5 µM in the subject.

5. The method of claim 2, wherein the steady state plasma concentration of the DNP in the subject is about 50 to about 100 times lower than the toxic concentration of the compound in the subject.

6. The method of claim 1, wherein administration of the composition provides therapeutically effective levels of the DNP in the subject for a period of time ranging from about 12 hours to about 24 hours.

7. The method of claim 1, wherein the composition is administered once, twice or three times a day to the subject.

8. The method of claim 1, wherein the significant systemic toxicity is indicated by increase in levels of liver enzymes, blood urea nitrogen or creatinine as compared to the corresponding levels in the subject in the absence of administration of the composition.

9. The method of claim 1, wherein the composition is formulated for oral administration.

10. The method of claim 1, further comprising administering to the subject at least one additional therapeutic agent.

11. The method of claim 10, wherein the composition and the at least one additional therapeutic agent are co-administered to the subject.

12. The method of claim 11, wherein the composition and the at least one additional therapeutic agent are co-formulated.

13. The method of claim 1, wherein the subject is a mammal.

14. The method of claim 13, wherein the mammal is human.

15. A method of increasing energy expenditure in a subject in need thereof, the method comprising orally administering to the subject a therapeutically effective amount of a pharmaceutical composition comprising;
   at least one pharmaceutically acceptable carrier and a therapeutically effective amount of 2,4-dinitrophenol (DNP) or a salt or solvate thereof;
   wherein the DNP or a salt or solvate thereof, is coated with an extended release coating comprising:
   i) at least one water soluble polymer: and
   ii) at least one water insoluble polymer,
   wherein the therapeutically effective amount of DNP is about 1 to about 10 mg/kg/day or about 1 to about 200 mg;
   wherein administration of the composition to a subject provides a steady state plasma concentration of DNP ranging from about 0.05 µM to about 200 µM in the subject, and wherein the composition does not cause significant systemic toxicity or significant increase in body temperature in the subject and, wherein the subject is afflicted with at least one disease or disorder selected from the group consisting of nonalcoholic fatty liver disease (NAFLD), non-alcoholic steatohepatitis (NASH), hepatic steatosis, type 2 diabetes (T2D), acquired lipodystrophy, inherited lipodystrophy, partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, insulin resistance, hepatic fibrosis, liver cirrhosis and hepatocellular carcinoma, whereby energy expenditure in the subject is increased.

16. The method of claim 15, wherein the therapeutically effective dose of the DNP ranges from about 1 mg/kg/day to about 10 mg/kg/day.

17. The method of claim 15, wherein administration of the composition provides a steady state plasma concentration of the DNP ranging from about 0.5 µM to about 50 µM in the subject.

18. The method of claim 17, wherein administration of the composition provides a steady state plasma concentration of the DNP ranging from about 3 µM to about 5 µM in the subject.

19. The method of claim 15, wherein administration of the composition provides therapeutically effective levels of the DNP in the subject for a period of time ranging from about 12 hours to about 24 hours.

20. The method of claim 15, wherein the composition is administered once, twice or three times a day to the subject.

21. The method of claim 15, wherein the significant systemic toxicity is indicated by increase in levels of liver enzymes, blood urea nitrogen or creatinine as compared to the corresponding levels in the subject in the absence of administration of the composition.

22. The method of claim 15, wherein the composition is formulated for oral administration.

23. The method of claim 15, further comprising administering to the subject at least one additional therapeutic agent.

24. The method of claim 15, wherein the subject is a mammal.

25. The method of claim 24, wherein the subject is a human.

26. An oral pharmaceutical composition comprising:
at least one pharmaceutically acceptable carrier and a therapeutically effective amount of 2,4-dinitrophenol (DNP), or a salt or solvate thereof;
wherein the DNP, or a salt or solvate thereof, is coated with an extended release coating comprising:
   i) at least one water soluble polymer; and
   ii) at least one water insoluble polymer,
wherein the therapeutically effective amount of DNP is about 1 to about 10 mg/kg/day or about 1 to about 200 mg;
wherein administration of the composition to a subject provides a steady state plasma concentration of DNP ranging from about 0.05 µM to about 200 µM in the subject, and
wherein the composition does not cause significant systemic toxicity or significant increase in body temperature in the subject.

27. The pharmaceutical composition of claim 26, wherein the composition does not change alanine aminotransferase (ALT) levels in the subject after administration.

28. The pharmaceutical composition of claim 26, wherein the composition does not change aspartate aminotransferase (AST) levels in the subject after administration.

29. The pharmaceutical composition of claim 26, wherein the steady state plasma concentration of the DNP in the subject is about 50 to about 100 times lower than the toxic concentration of the DNP in the subject.

30. The pharmaceutical composition of claim 26, wherein administration of the amount of the composition affords therapeutically effective levels of the DNP in the subject for a period of time ranging from about 12 hours to about 24 hours.

31. The pharmaceutical composition of claim 26, wherein the significant systemic toxicity is indicated by increase in levels of liver enzymes, blood urea nitrogen or creatinine, as compared to the corresponding levels in the subject in the absence of administration of the composition.

32. The pharmaceutical composition of claim 26, wherein the composition further comprises at least one additional therapeutic agent.

33. The pharmaceutical composition of claim 26, wherein the at least one water soluble polymer comprises hydroxypropylcellulose.

34. The pharmaceutical composition of claim 26, wherein the coated DNP is in a bead or sphere form.

35. The pharmaceutical composition of claim 26, wherein the at least one water insoluble polymer comprises ethylcellulose.

36. The pharmaceutical composition of claim 26, wherein the subject is a mammal.

37. The pharmaceutical composition of claim 36, wherein the mammal is human.

* * * * *